US012636395B2

(12) United States Patent
Simmons et al.

(10) Patent No.: US 12,636,395 B2
(45) Date of Patent: May 26, 2026

(54) OZONE-BASED DISINFECTION SYSTEM FOR REFRIGERATED STORAGE AND ICE-MAKING APPLICATIONS

(71) Applicant: BioSure North America LLC, Fair Oaks Ranch, TX (US)

(72) Inventors: Darren Simmons, Fair Oaks Ranch, TX (US); Gavin Hsu, New Taipei (TW); Maxwell Hsu, New Taipei (TW); Ivor J. J. Longo, Atlanta, GA (US); H. Brock Kolls, Alpharetta, GA (US)

(73) Assignee: BioSure North America LLC, Fair Oaks Ranch, TX (US)

( * ) Notice: Subject to any disclaimer, the term of this patent is extended or adjusted under 35 U.S.C. 154(b) by 0 days.

(21) Appl. No.: 19/223,513

(22) Filed: May 30, 2025

(65) Prior Publication Data

US 2025/0332311 A1 Oct. 30, 2025

Related U.S. Application Data

(63) Continuation-in-part of application No. 19/185,759, filed on Apr. 22, 2025, now Pat. No. 12,514,950, and
(Continued)

(51) Int. Cl.
A61L 9/015 (2006.01)
A61L 2/183 (2026.01)
(Continued)

(52) U.S. Cl.
CPC .............. A61L 9/015 (2013.01); A61L 2/183 (2013.01); B01D 53/8675 (2013.01);
(Continued)

(58) Field of Classification Search
CPC ..... A61L 9/015; A61L 2/183; B01D 53/8675; B01D 53/8696; B01D 53/885; C02F 1/78; C02F 1/46104; F25D 17/042
See application file for complete search history.

(56) References Cited

FOREIGN PATENT DOCUMENTS

| | | | | |
|---|---|---|---|---|
| CN | 1334784 A | * | 2/2002 | ............... C25B 9/19 |
| CN | 206304547 U | * | 7/2017 | |
| CN | 114087838 A | * | 2/2022 | ............. F25D 29/00 |

OTHER PUBLICATIONS

English machine translation of CN-206304547-U (Year: 2017).*
English translation of CN-114087838-A (Year: 2022).*
English translation of CN-1334784-A (Year: 2022).*

* cited by examiner

*Primary Examiner* — Sean E Conley
(74) *Attorney, Agent, or Firm* — H. Brock Kolls

(57) ABSTRACT

The present invention relates to a system and method for treating air and water in refrigerated spaces using ozone-based disinfection. The system includes an electrolytic ozone generator configured to produce gaseous ozone from water and an air circulation subsystem to create an oxidizing airflow within a housing. The airflow is directed across a titanium dioxide-coated surface to reduce ozone concentration before reentry into the refrigerated space. A controller manages disinfection and purification modes, enabling safe air treatment in environments such as ice machines, walk-in refrigerators, and consumer appliances. In some embodiments, aqueous ozone is also routed to ice makers or water dispensers for waterline disinfection. Optional features include manganese dioxide treatment modules for hydroxyl radical generation, automated door locking during disinfection, and ozone sensors for safety compliance. The invention enables programmable, sensor-driven, and safe disinfection cycles without requiring external ozone emission, supporting food safety and occupant protection.

24 Claims, 25 Drawing Sheets

Related U.S. Application Data a continuation-in-part of application No. 19/185,738, filed on Apr. 22, 2025, now Pat. No. 12,458,721, and a continuation-in-part of application No. 19/037,391, filed on Jan. 27, 2025, and a continuation-in-part of application No. 19/036,758, filed on Jan. 24, 2025, now Pat. No. 12,357,716, and a continuation-in-part of application No. 18/966,217, filed on Dec. 3, 2024, and a continuation-in-part of application No. 18/919, 605, filed on Oct. 18, 2024, now Pat. No. 12,520,855, and a continuation-in-part of application No. 18/646, 394, filed on Apr. 25, 2024.

(51) Int. Cl.

| | | |
|---|---|---|
| *B01D 53/86* | (2006.01) | |
| *B01D 53/88* | (2006.01) | |
| *B67D 1/07* | (2006.01) | |
| *C02F 1/461* | (2023.01) | |
| *C02F 1/78* | (2023.01) | |
| *F25D 17/04* | (2006.01) | |

(52) U.S. Cl.

CPC ....... *B01D 53/8696* (2013.01); *B01D 53/885* (2013.01); *C02F 1/46104* (2013.01); *C02F 1/78* (2013.01); *F25D 17/042* (2013.01); *A61L 2202/11* (2013.01); *A61L 2202/14* (2013.01); *A61L 2209/111* (2013.01); *A61L 2209/134* (2013.01); *A61L 2209/212* (2013.01); *A61L 2209/213* (2013.01); *B01D 2255/20707* (2013.01); *B01D 2257/106* (2013.01); *B01D 2257/91* (2013.01); *B67D 2001/075* (2013.01); *C02F 2201/005* (2013.01); *C02F 2201/4612* (2013.01); *C02F 2201/782* (2013.01); *C02F 2303/04* (2013.01); *C02F 2307/12* (2013.01); *F25C 2400/12* (2013.01); *F25D 2317/0416* (2013.01)

Ice Makers/
Refrigerators/Close
Musty Spaces/Other

Ⓐ

Air Purifiers
- Restroom Applications
- Room/Gym Deodorizing
- Hospitals/Offices/Other

Ⓑ

HVAC Air Handling

Ⓒ

**Kitchens/Quick Serve
Restaurants/ Other**

Ⓓ

Ⓔ Other Environments And Applications 218

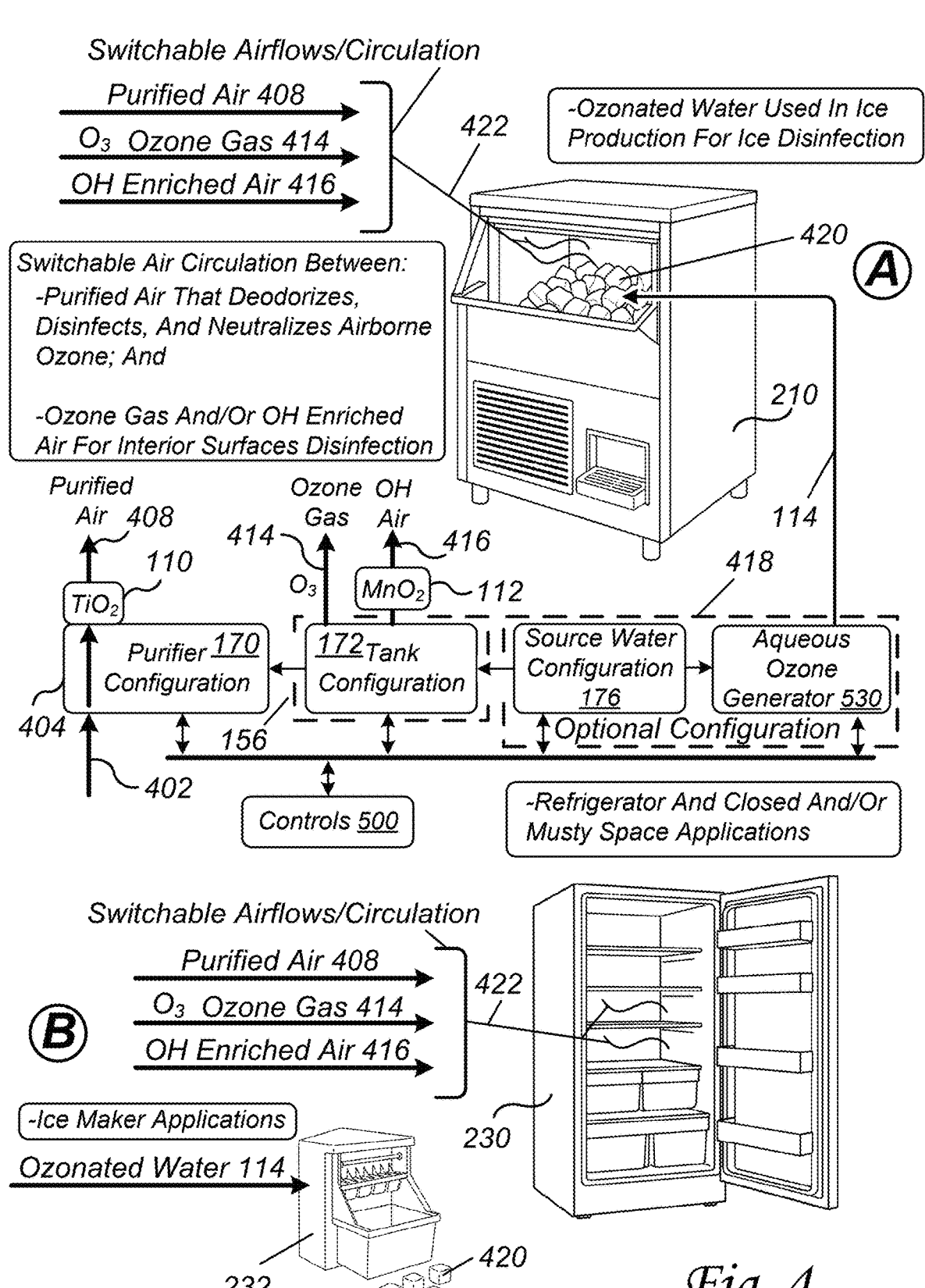

Switchable Airflows/Circulation

Purified Air 408

O₃ Ozone Gas 414

OH Enriched Air 416

422

-Ozonated Water Used In Ice Production For Ice Disinfection

420

Ⓐ

Switchable Air Circulation Between:
-Purified Air That Deodorizes, Disinfects, And Neutralizes Airborne Ozone; And -Ozone Gas And/Or OH Enriched Air For Interior Surfaces Disinfection

210

114

Purified Air 408

Ozone Gas 414

OH Air 416

110

O₃

$TiO_2$

404

402

$MnO_2$ ~112

Purifier 170 Configuration

172 Tank Configuration

156

Source Water Configuration 176

418

Aqueous Ozone Generator 530

Optional Configuration

Controls 500

-Refrigerator And Closed And/Or Musty Space Applications

Switchable Airflows/Circulation

Ⓑ

Purified Air 408

O₃ Ozone Gas 414

OH Enriched Air 416

422

230

-Ice Maker Applications

Ozonated Water 114

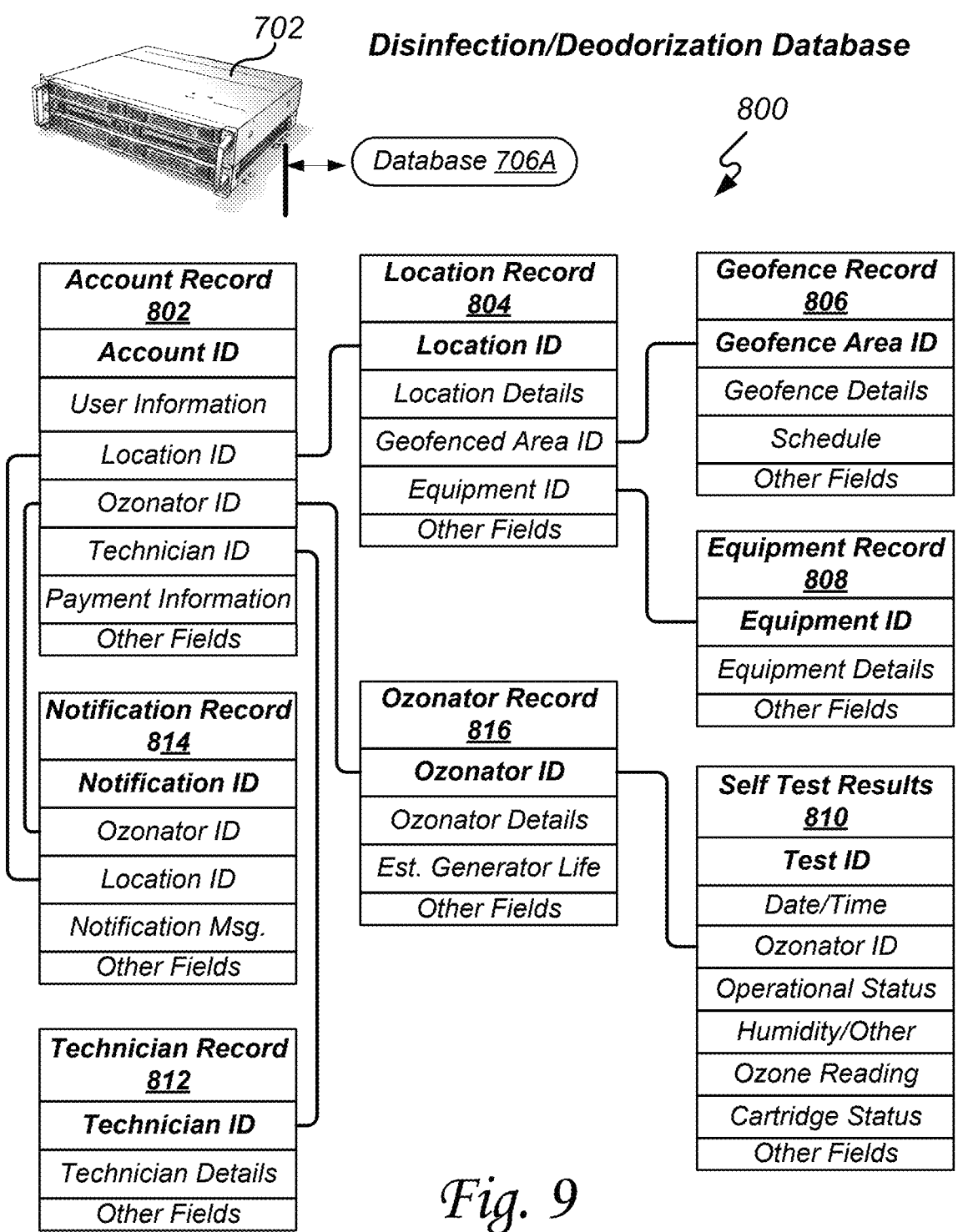

702

Disinfection/Deodorization Database

Database 706A

800

Account Record
802

Account ID

User Information

Location ID

Ozonator ID

Technician ID

Payment Information

Other Fields

Location Record
804

Location ID

Location Details

Geofenced Area ID

Equipment ID

Other Fields

Geofence Record
806

Geofence Area ID

Geofence Details

Schedule

Other Fields

Equipment Record
808

Equipment ID

Equipment Details

Other Fields

Notification Record
814

Notification ID

Ozonator ID

Location ID

Notification Msg.

Other Fields

Ozonator Record
816

Ozonator ID

Ozonator Details

Est. Generator Life

Other Fields

Self Test Results
810

Test ID

Date/Time

Ozonator ID

Operational Status

Humidity/Other

Ozone Reading

Cartridge Status

Other Fields

Technician Record
812

Technician ID

Technician Details

Other Fields

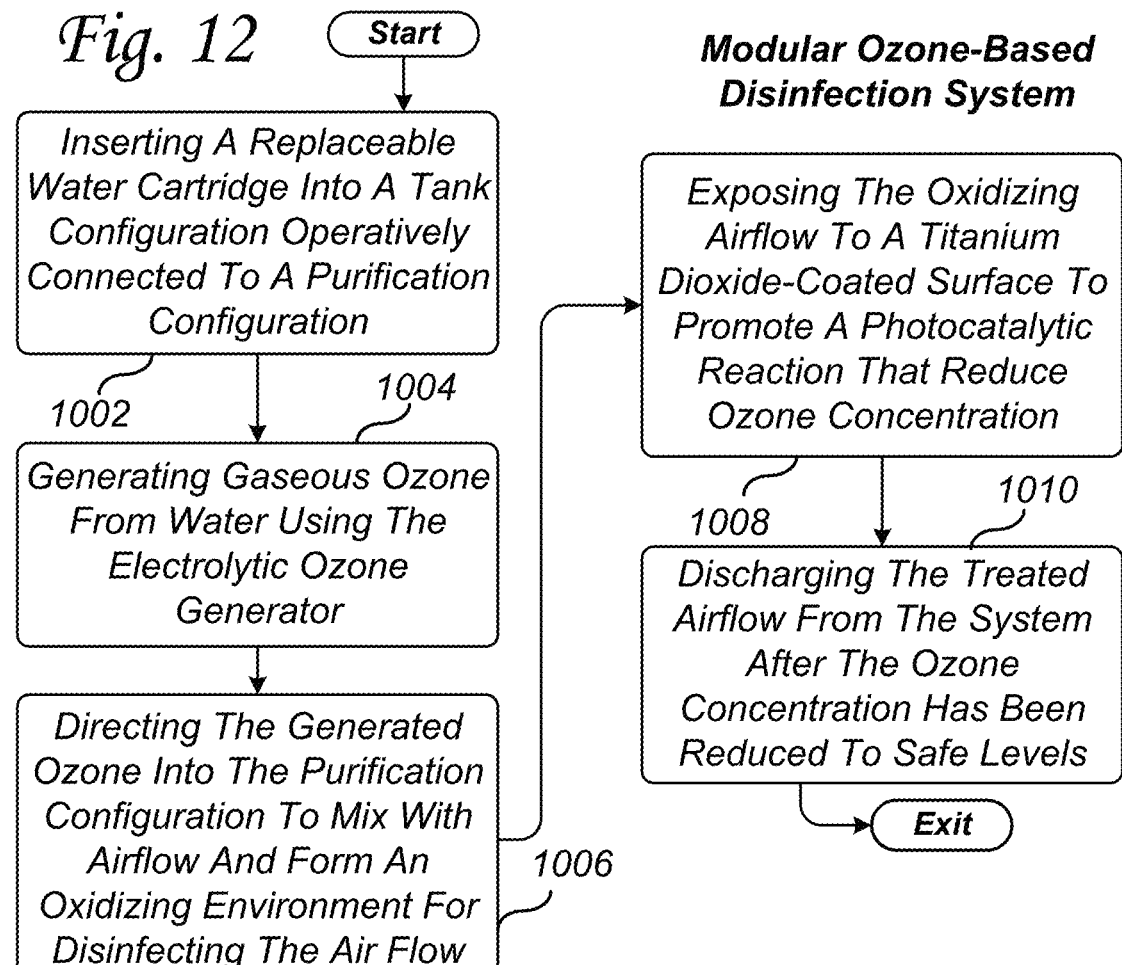

*Fig. 12*

Start

Modular Ozone-Based Disinfection System

Inserting A Replaceable Water Cartridge Into A Tank Configuration Operatively Connected To A Purification Configuration 1002    1004

Generating Gaseous Ozone From Water Using The Electrolytic Ozone Generator

Directing The Generated Ozone Into The Purification Configuration To Mix With Airflow And Form An Oxidizing Environment For Disinfecting The Air Flow

1006

Exposing The Oxidizing Airflow To A Titanium Dioxide-Coated Surface To Promote A Photocatalytic Reaction That Reduce Ozone Concentration 1008    1010

Discharging The Treated Airflow From The System After The Ozone Concentration Has Been Reduced To Safe Levels Exit

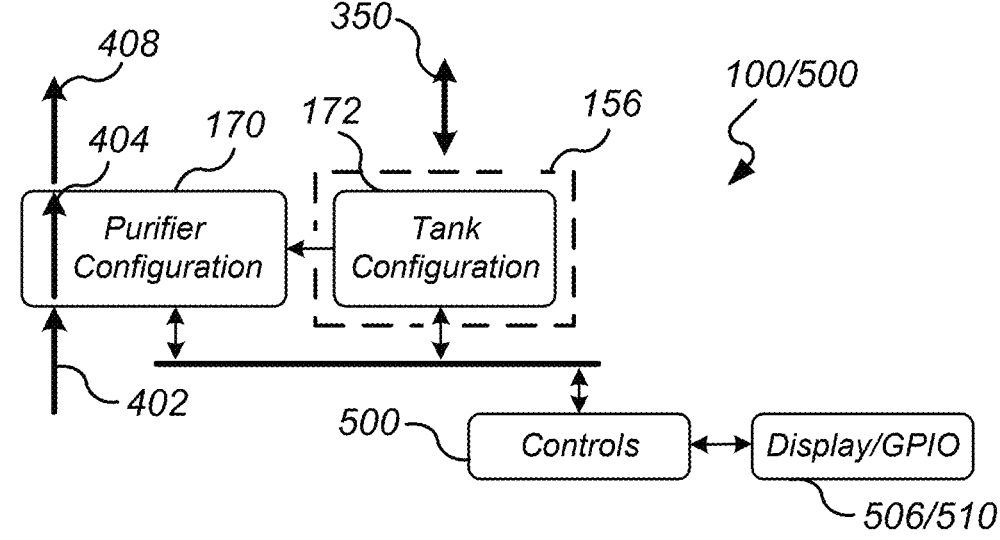

408

350

100/500

404    170    172    156

Purifier Configuration ← Tank Configuration

402

500

Controls ↔ Display/GPIO

506/510

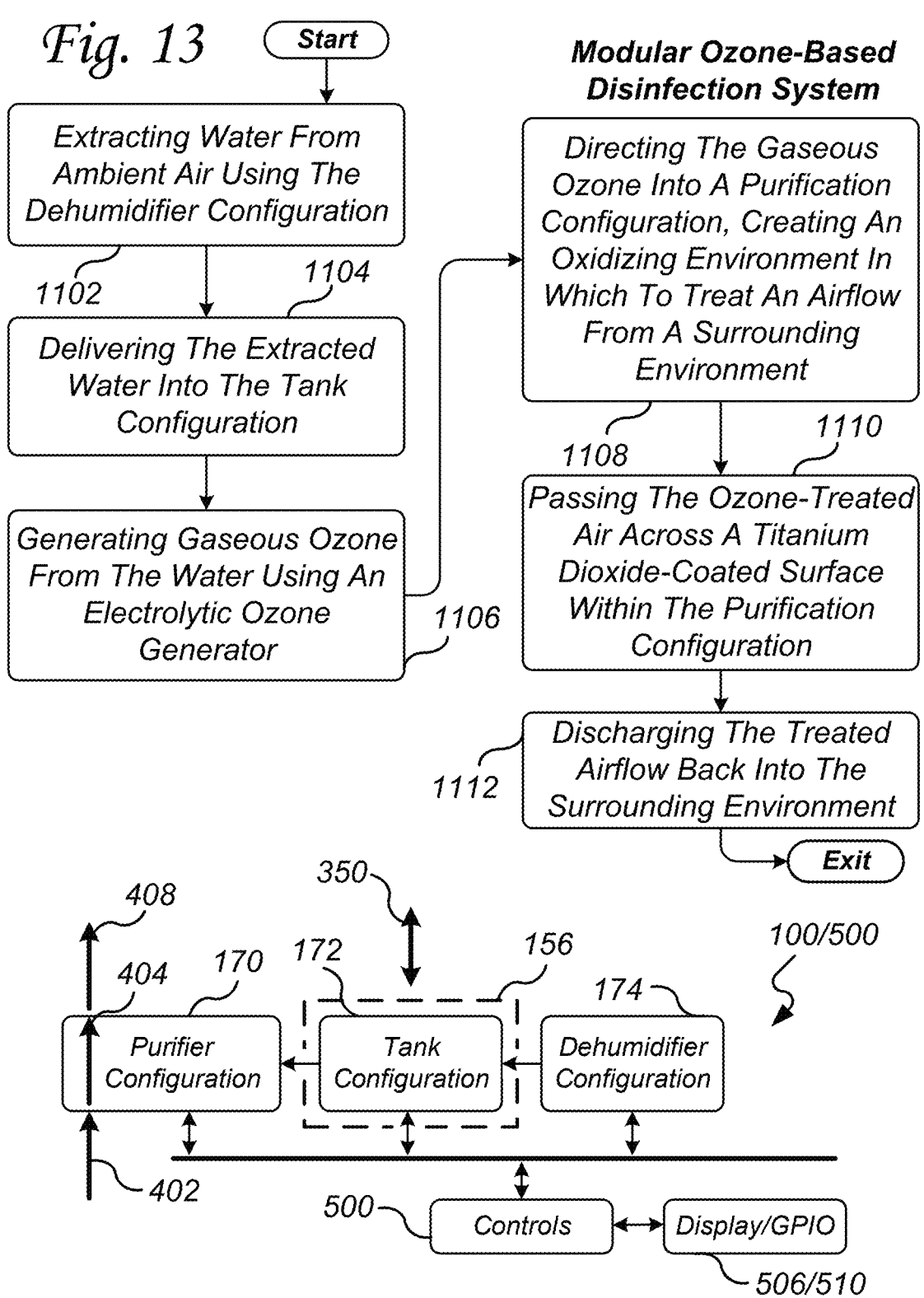

*Fig. 13*

Start

Modular Ozone-Based Disinfection System

Extracting Water From Ambient Air Using The Dehumidifier Configuration

1102

1104

Delivering The Extracted Water Into The Tank Configuration

Generating Gaseous Ozone From The Water Using An Electrolytic Ozone Generator

1106

Directing The Gaseous Ozone Into A Purification Configuration, Creating An Oxidizing Environment In Which To Treat An Airflow From A Surrounding Environment

1108

1110

Passing The Ozone-Treated Air Across A Titanium Dioxide-Coated Surface Within The Purification Configuration Discharging The Treated Airflow Back Into The Surrounding Environment

1112

Exit

408

350

100/500

404

170

172

156

174

Purifier Configuration

Tank Configuration

Dehumidifier Configuration

402

500

Controls

Display/GPIO

506/510

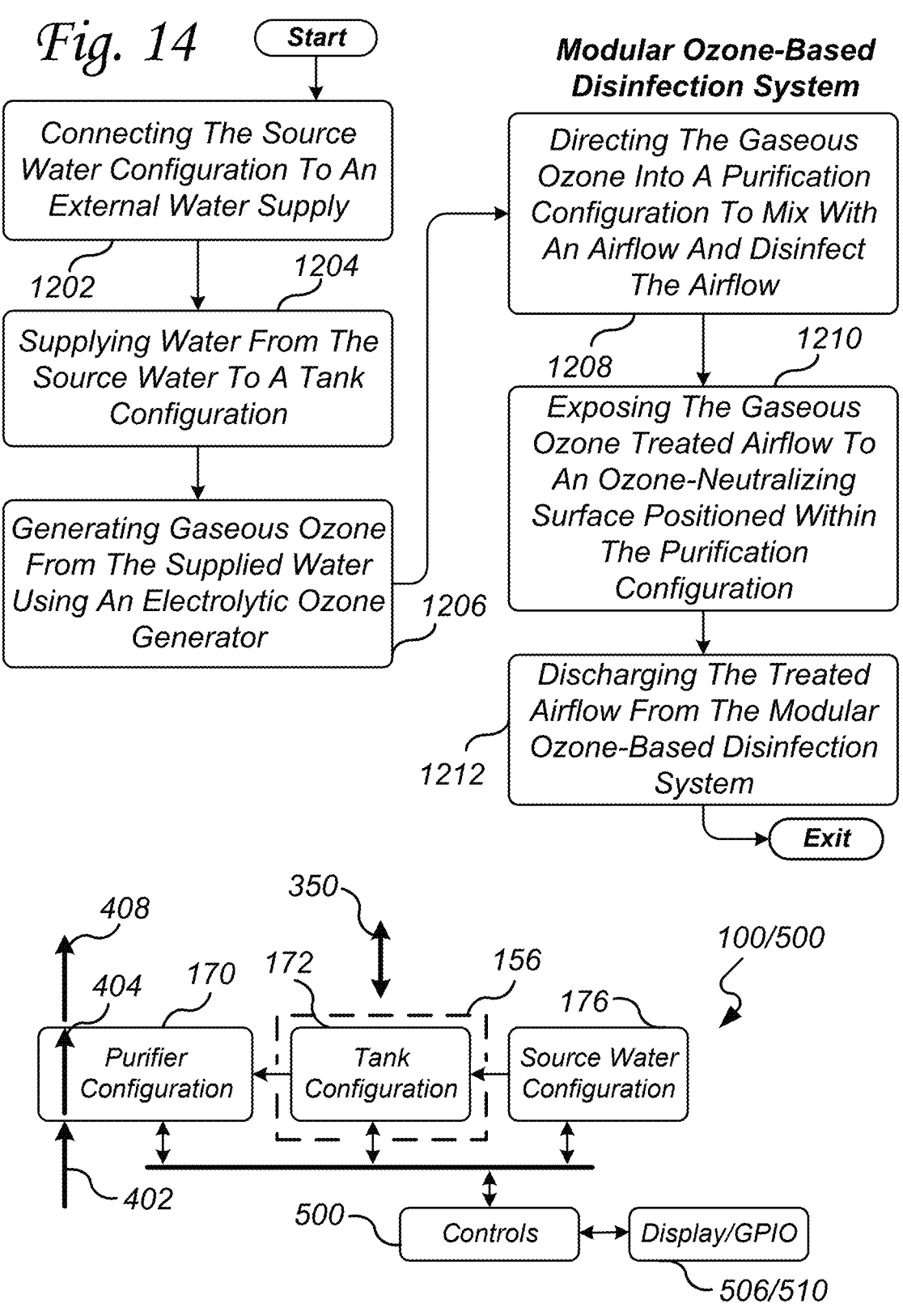

*Fig. 14*

Start

Modular Ozone-Based Disinfection System

Connecting The Source Water Configuration To An External Water Supply

1202

1204

Supplying Water From The Source Water To A Tank Configuration

Generating Gaseous Ozone From The Supplied Water Using An Electrolytic Ozone Generator

1206

Directing The Gaseous Ozone Into A Purification Configuration To Mix With An Airflow And Disinfect The Airflow

1208

1210

Exposing The Gaseous Ozone Treated Airflow To An Ozone-Neutralizing Surface Positioned Within The Purification Configuration Discharging The Treated Airflow From The Modular Ozone-Based Disinfection System

1212

Exit 408
404  170  172  156
350
176
100/500

402

Purifier Configuration

Tank Configuration

Source Water Configuration

500

Controls

Display/GPIO

506/510

Figure 15:
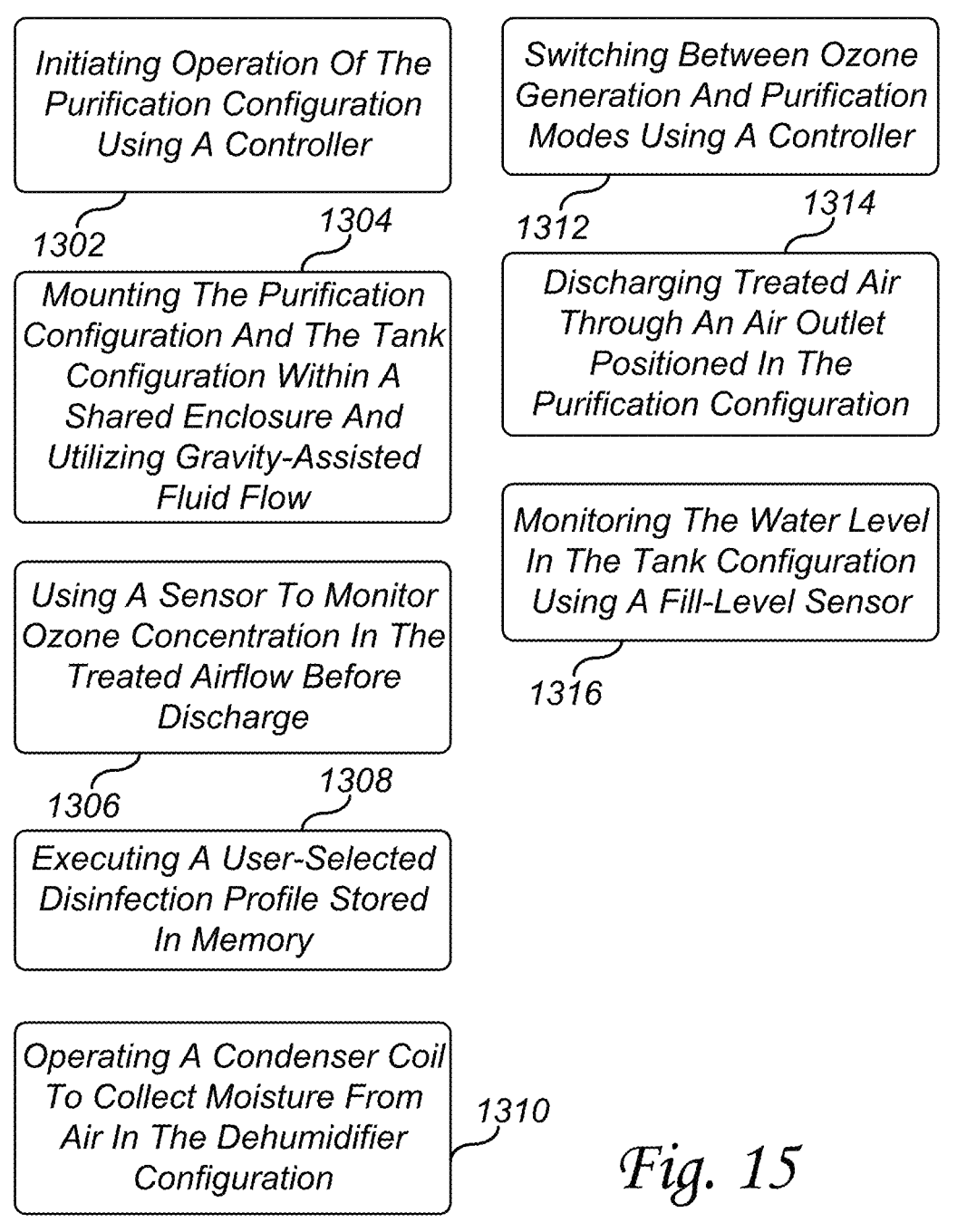

Initiating Operation Of The Purification Configuration Using A Controller

1302

Mounting The Purification Configuration And The Tank Configuration Within A Shared Enclosure And Utilizing Gravity-Assisted Fluid Flow

1304

Using A Sensor To Monitor Ozone Concentration In The Treated Airflow Before Discharge

1306

Executing A User-Selected Disinfection Profile Stored In Memory

1308

Operating A Condenser Coil To Collect Moisture From Air In The Dehumidifier Configuration

1310

Switching Between Ozone Generation And Purification Modes Using A Controller

1312

Discharging Treated Air Through An Air Outlet Positioned In The Purification Configuration

1314

Monitoring The Water Level In The Tank Configuration Using A Fill-Level Sensor

*Fig. 16*   ( Start )                    *Refrigerated Spaces*
                                         *Application*

Operating A Controller To
Initiate Purification Mode By
Activating An Electrolytic
Ozone Generator And An
Air Circulation Subsystem

*1402*          *1404*

Generating Gaseous Ozone
From Water Using The
Electrolytic Ozone
Generator

Mixing The Gaseous Ozone
With Airflow In A Housing
To Create An Oxidizing
Environment For
Disinfecting The Airflow

*1406*

Directing The Oxidizing
Airflow Across A Titanium
Dioxide-Coated Surface

*1408*          *1410*

Returning The Treated
Airflow Into The
Refrigerated Space ( Exit )

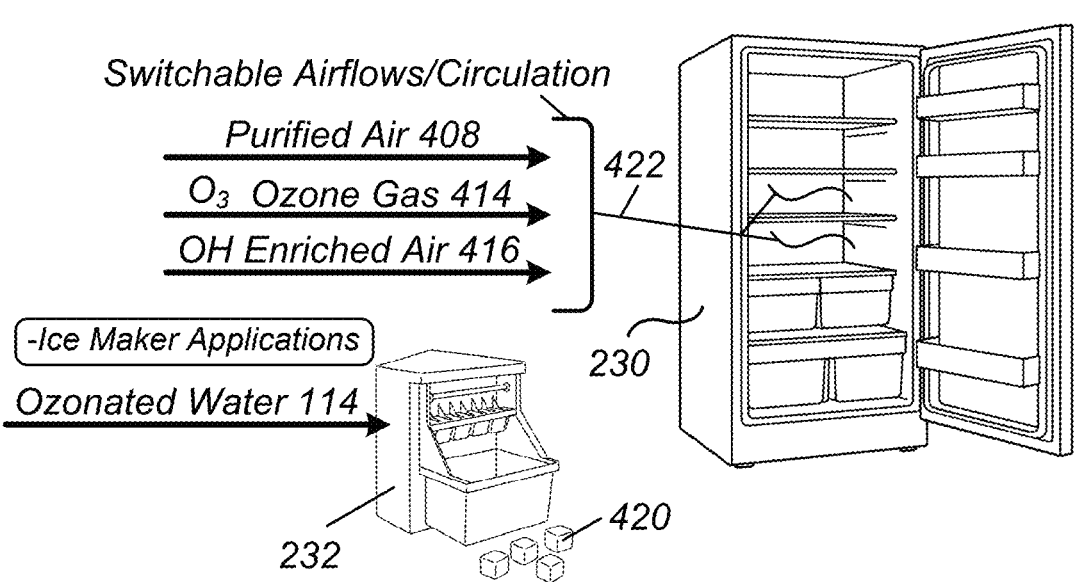

*Switchable Airflows/Circulation*

Purified Air 408

O₃  Ozone Gas 414

OH Enriched Air 416

*422*

-Ice Maker Applications

Ozonated Water 114

*230*

*232*        *420*

*Fig. 17*   ( Start )

Refrigerated Spaces Application

Operating An Ozone-Based Disinfection System In A Disinfection Mode
*1502*

Directing The Gaseous Ozone Into The Refrigerated Space For A Fixed Disinfection Period
*1504*

Transitioning The Ozone-Based Disinfection System Into A Purification Mode Using A Controller
*1506*

Recirculating Air From The Refrigerated Space Through A Purification Configuration
*1508*

Reducing The Ozone Concentration To A Level Suitable To A Refrigerated Space
*1510*

( Exit )

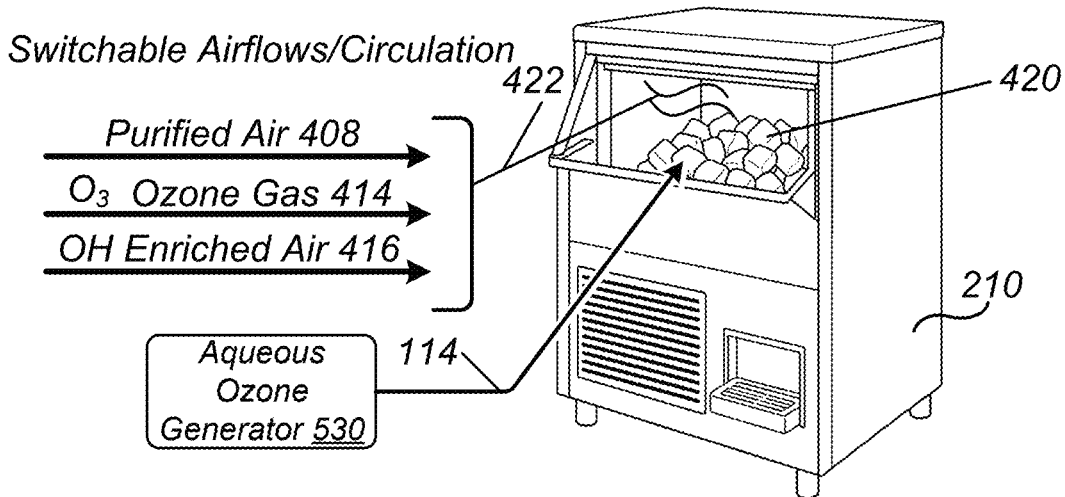

Switchable Airflows/Circulation

Purified Air 408

O₃  Ozone Gas 414

OH Enriched Air 416

Aqueous Ozone Generator 530

114

422

420

210

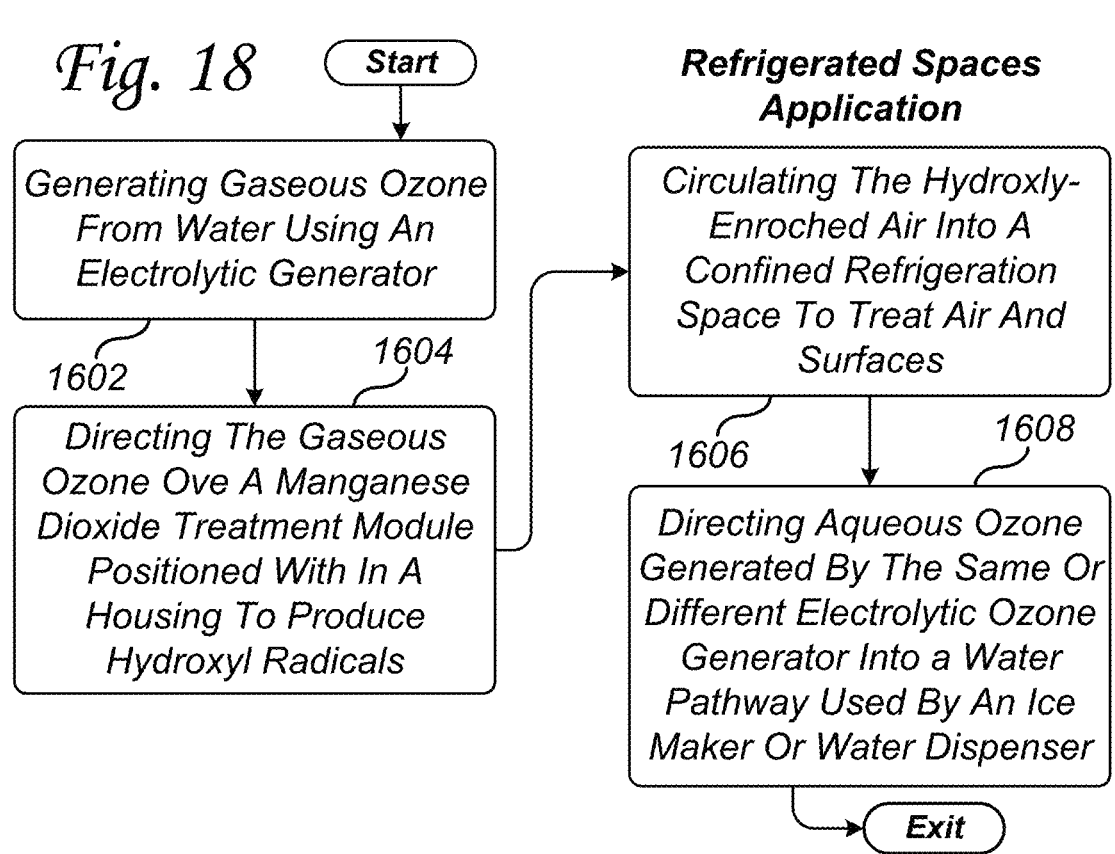

*Fig. 18*

Start

Generating Gaseous Ozone From Water Using An Electrolytic Generator

*1602*

*1604*

Directing The Gaseous Ozone Ove A Manganese Dioxide Treatment Module Positioned With In A Housing To Produce Hydroxyl Radicals

Refrigerated Spaces Application

Circulating The Hydroxly-Enriched Air Into A Confined Refrigeration Space To Treat Air And Surfaces

*1606*

*1608*

Directing Aqueous Ozone Generated By The Same Or Different Electrolytic Ozone Generator Into a Water Pathway Used By An Ice Maker Or Water Dispenser

Exit

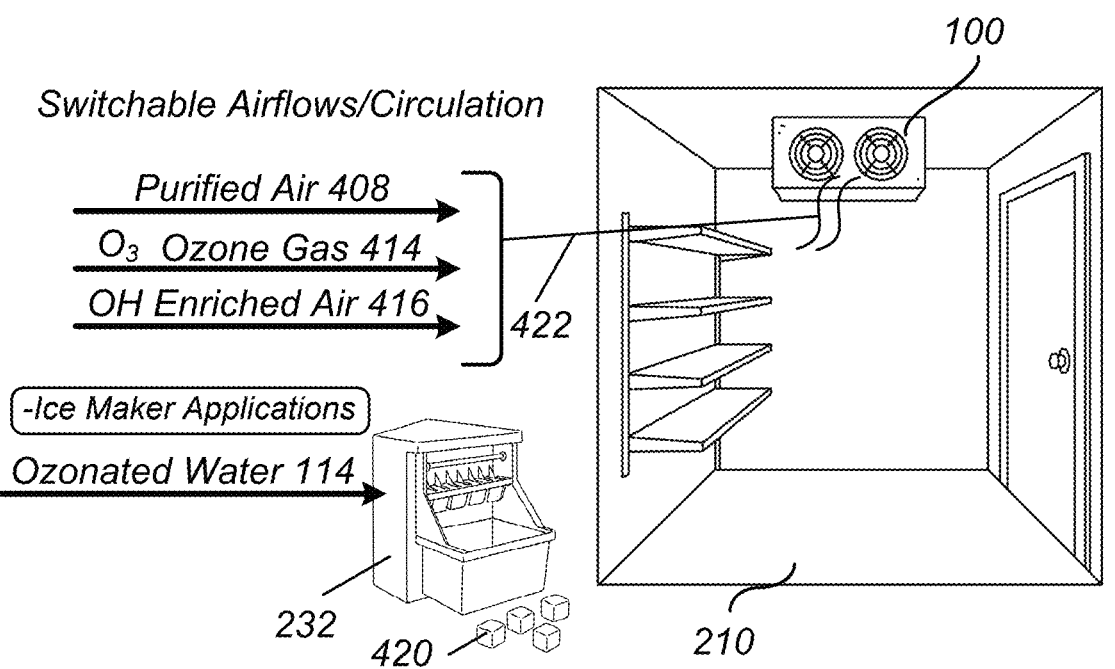

*Switchable Airflows/Circulation*

Purified Air 408

O₃ Ozone Gas 414

OH Enriched Air 416

422

-Ice Maker Applications

Ozonated Water 114

100

232

420

210

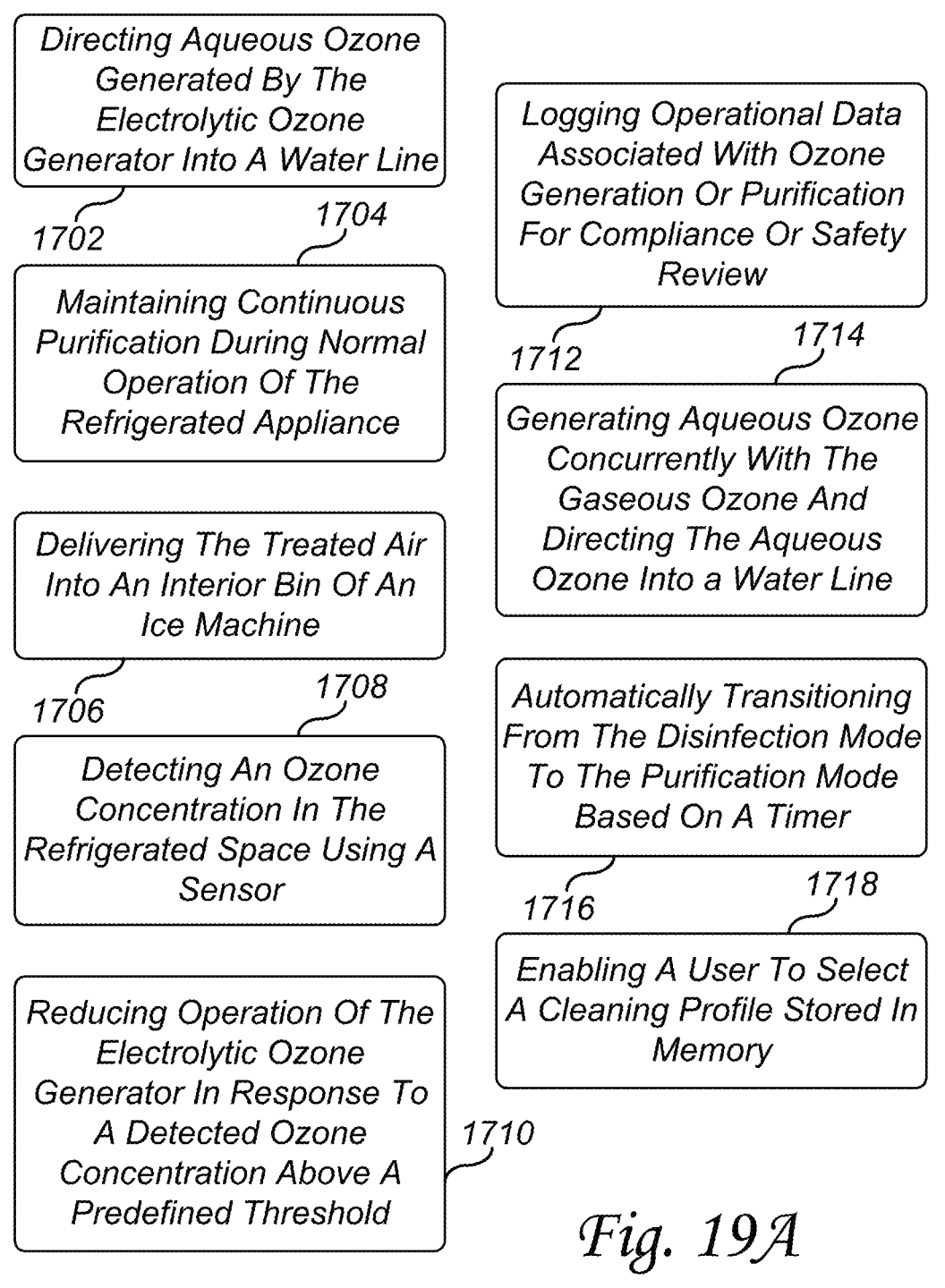

Directing Aqueous Ozone Generated By The Electrolytic Ozone Generator Into A Water Line

1702

1704

Maintaining Continuous Purification During Normal Operation Of The Refrigerated Appliance Delivering The Treated Air Into An Interior Bin Of An Ice Machine

1706

1708

Detecting An Ozone Concentration In The Refrigerated Space Using A Sensor

Reducing Operation Of The Electrolytic Ozone Generator In Response To A Detected Ozone Concentration Above A Predefined Threshold

1710

Logging Operational Data Associated With Ozone Generation Or Purification For Compliance Or Safety Review

1712

1714

Generating Aqueous Ozone Concurrently With The Gaseous Ozone And Directing The Aqueous Ozone Into a Water Line Automatically Transitioning From The Disinfection Mode To The Purification Mode Based On A Timer

1716

1718

Enabling A User To Select A Cleaning Profile Stored In Memory

*Fig. 19A*

Directing Recirculated Air Across A Titanium Dioxide-Coated Surface 1720                    1722

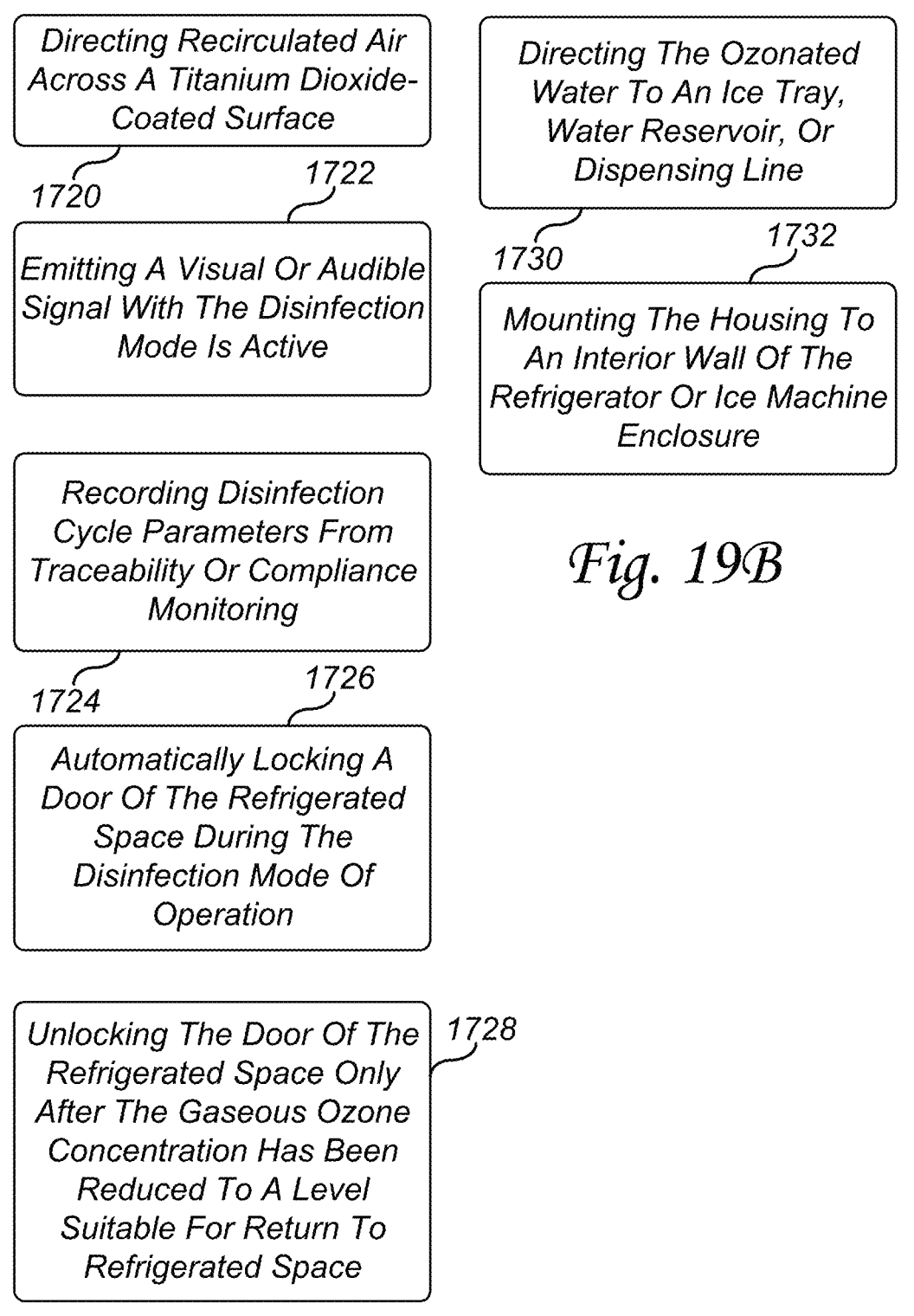

Emitting A Visual Or Audible Signal With The Disinfection Mode Is Active

Recording Disinfection Cycle Parameters From Traceability Or Compliance Monitoring 1724                    1726

Automatically Locking A Door Of The Refrigerated Space During The Disinfection Mode Of Operation Unlocking The Door Of The Refrigerated Space Only After The Gaseous Ozone Concentration Has Been Reduced To A Level Suitable For Return To Refrigerated Space

1728

Directing The Ozonated Water To An Ice Tray, Water Reservoir, Or Dispensing Line 1730                    1732

Mounting The Housing To An Interior Wall Of The Refrigerator Or Ice Machine Enclosure

*Fig. 19B*

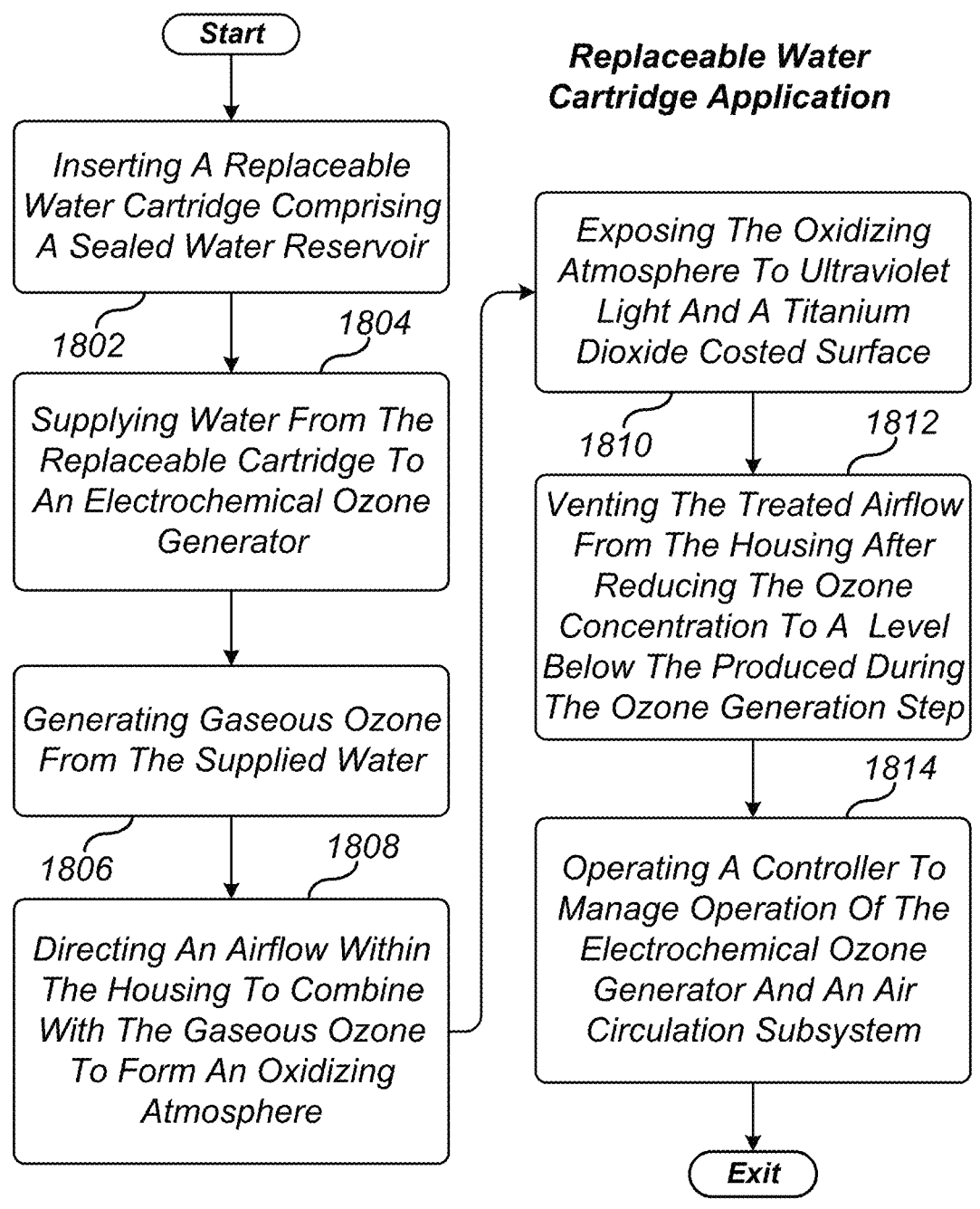

Start

Inserting A Replaceable Water Cartridge Comprising A Sealed Water Reservoir

*1802*                              *1804*

Supplying Water From The Replaceable Cartridge To An Electrochemical Ozone Generator Generating Gaseous Ozone From The Supplied Water

*1806*                              *1808*

Directing An Airflow Within The Housing To Combine With The Gaseous Ozone To Form An Oxidizing Atmosphere

Replaceable Water Cartridge Application

Exposing The Oxidizing Atmosphere To Ultraviolet Light And A Titanium Dioxide Costed Surface

*1810*                              *1812*

Venting The Treated Airflow From The Housing After Reducing The Ozone Concentration To A  Level Below The Produced During The Ozone Generation Step

*1814*

Operating A Controller To Manage Operation Of The Electrochemical Ozone Generator And An Air Circulation Subsystem

Exit

*Fig. 20*

Replaceable Water Cartridge Application

Figure 22:
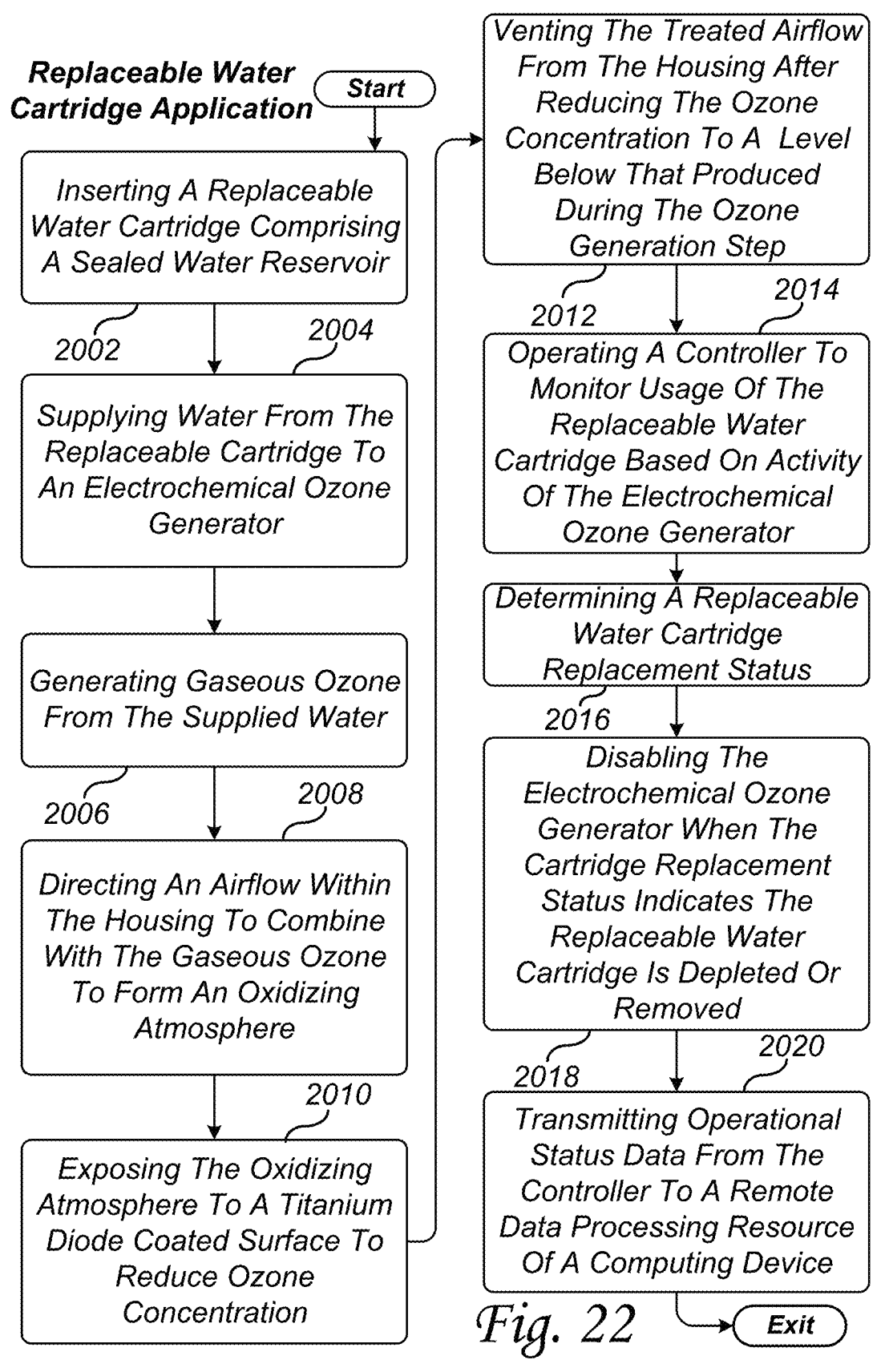

Replaceable Water Cartridge Application ( Start )

Inserting A Replaceable Water Cartridge Comprising A Sealed Water Reservoir

*2002*     *2004*

Supplying Water From The Replaceable Cartridge To An Electrochemical Ozone Generator Generating Gaseous Ozone From The Supplied Water

*2006*     *2008*

Directing An Airflow Within The Housing To Combine With The Gaseous Ozone To Form An Oxidizing Atmosphere

*2010*

Exposing The Oxidizing Atmosphere To A Titanium Diode Coated Surface To Reduce Ozone Concentration Venting The Treated Airflow From The Housing After Reducing The Ozone Concentration To A Level Below That Produced During The Ozone Generation Step

*2012*     *2014*

Operating A Controller To Monitor Usage Of The Replaceable Water Cartridge Based On Activity Of The Electrochemical Ozone Generator Determining A Replaceable Water Cartridge Replacement Status

*2016*

Disabling The Electrochemical Ozone Generator When The Cartridge Replacement Status Indicates The Replaceable Water Cartridge Is Depleted Or Removed

*2018*     *2020*

Transmitting Operational Status Data From The Controller To A Remote Data Processing Resource Of A Computing Device

*Fig. 22*     ( Exit )

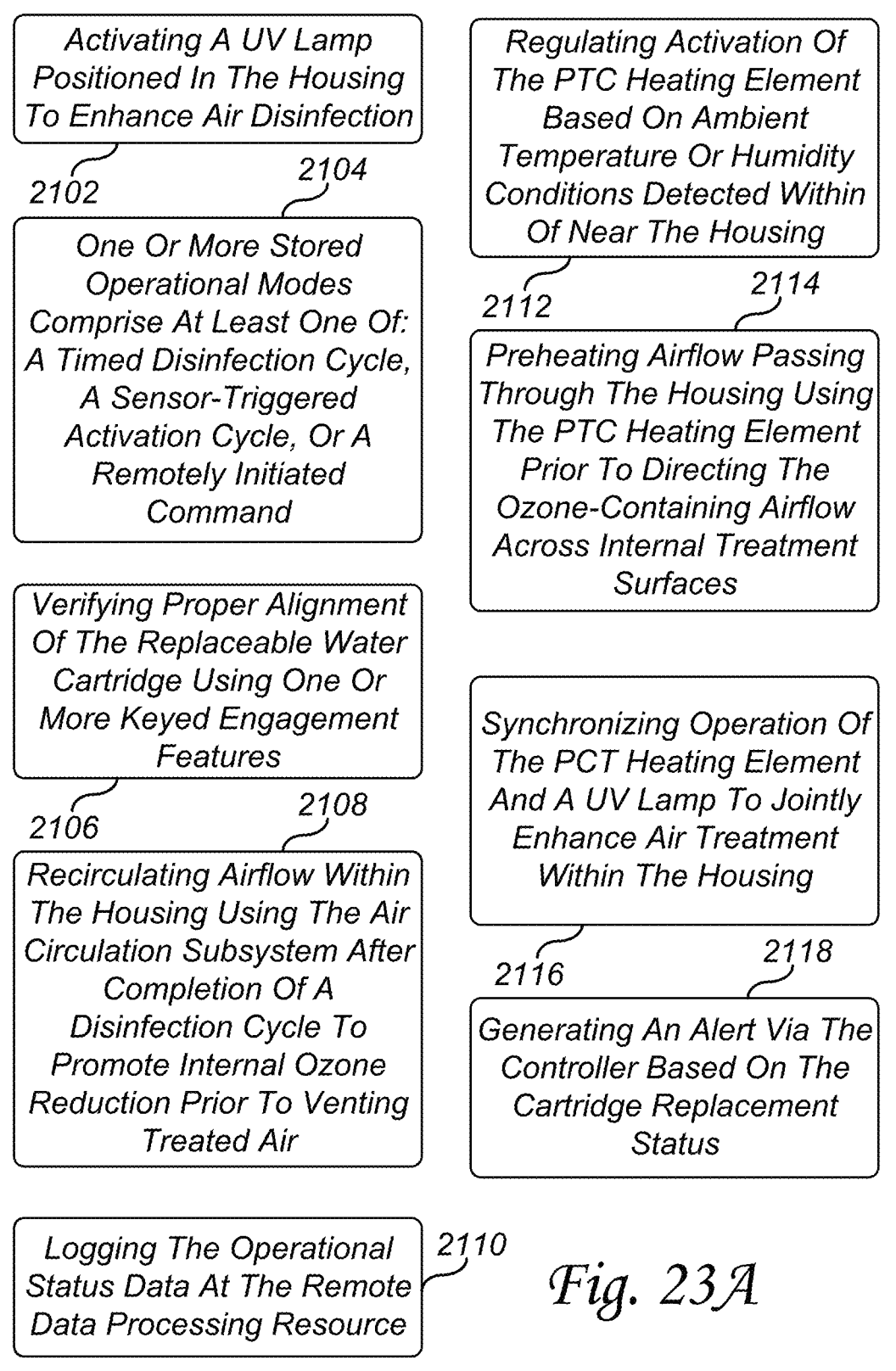

Activating A UV Lamp Positioned In The Housing To Enhance Air Disinfection 2102     2104

One Or More Stored Operational Modes Comprise At Least One Of: A Timed Disinfection Cycle, A Sensor-Triggered Activation Cycle, Or A Remotely Initiated Command Verifying Proper Alignment Of The Replaceable Water Cartridge Using One Or More Keyed Engagement Features 2106     2108

Recirculating Airflow Within The Housing Using The Air Circulation Subsystem After Completion Of A Disinfection Cycle To Promote Internal Ozone Reduction Prior To Venting Treated Air Logging The Operational Status Data At The Remote Data Processing Resource

2110

Regulating Activation Of The PTC Heating Element Based On Ambient Temperature Or Humidity Conditions Detected Within Of Near The Housing 2112     2114

Preheating Airflow Passing Through The Housing Using The PTC Heating Element Prior To Directing The Ozone-Containing Airflow Across Internal Treatment Surfaces Synchronizing Operation Of The PCT Heating Element And A UV Lamp To Jointly Enhance Air Treatment Within The Housing 2116     2118

Generating An Alert Via The Controller Based On The Cartridge Replacement Status

*Fig. 23A*

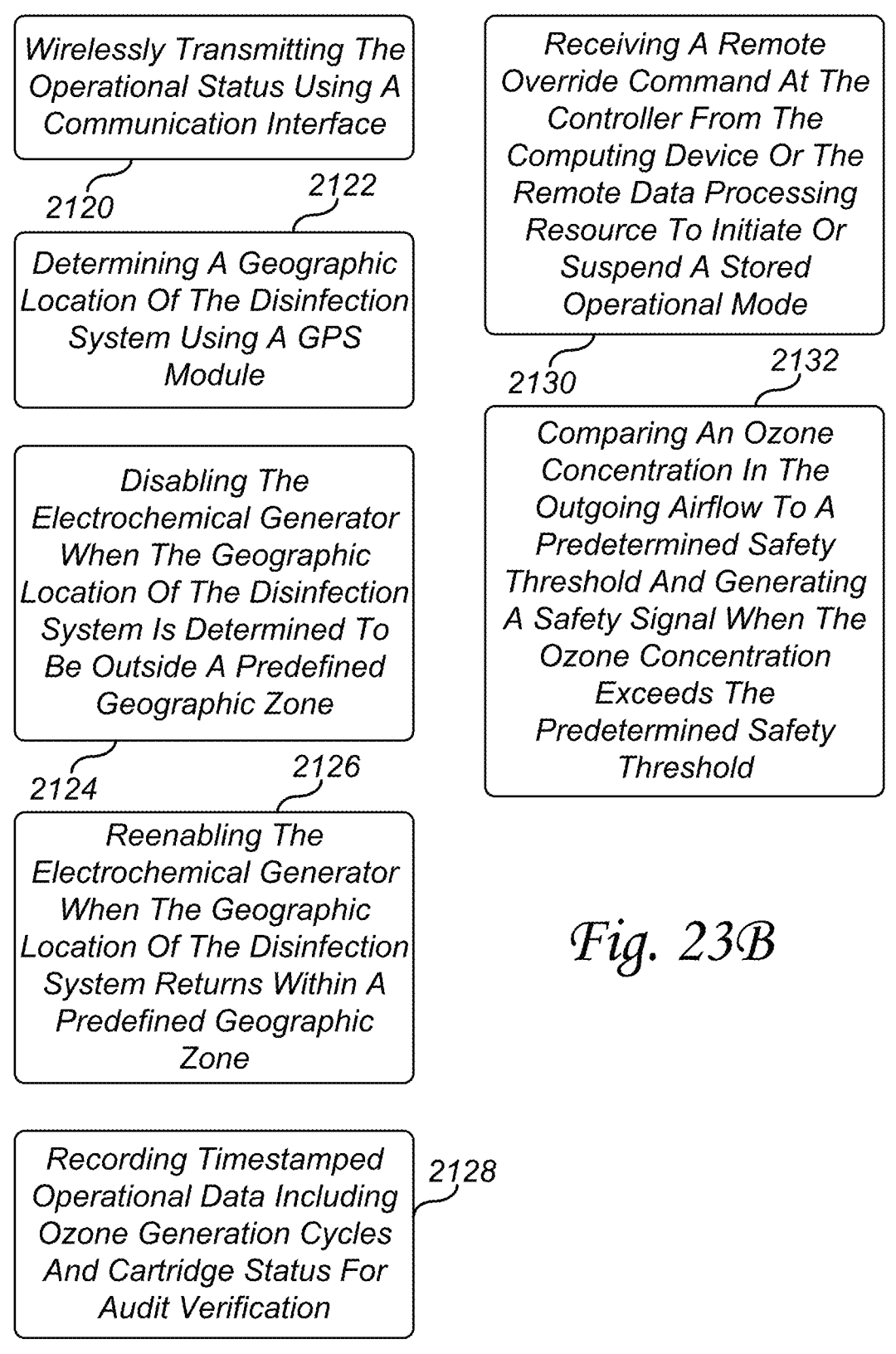

Wirelessly Transmitting The Operational Status Using A Communication Interface

2120

2122

Determining A Geographic Location Of The Disinfection System Using A GPS Module

Disabling The Electrochemical Generator When The Geographic Location Of The Disinfection System Is Determined To Be Outside A Predefined Geographic Zone

2124

2126

Reenabling The Electrochemical Generator When The Geographic Location Of The Disinfection System Returns Within A Predefined Geographic Zone Recording Timestamped Operational Data Including Ozone Generation Cycles And Cartridge Status For Audit Verification

2128

Receiving A Remote Override Command At The Controller From The Computing Device Or The Remote Data Processing Resource To Initiate Or Suspend A Stored Operational Mode

2130

2132

Comparing An Ozone Concentration In The Outgoing Airflow To A Predetermined Safety Threshold And Generating A Safety Signal When The Ozone Concentration Exceeds The Predetermined Safety Threshold

*Fig. 23B*

OZONE-BASED DISINFECTION SYSTEM FOR REFRIGERATED STORAGE AND ICE-MAKING APPLICATIONS

CROSS-REFERENCE TO RELATED APPLICATIONS

This application contains subject matter which is related to the subject matter of the following co-pending applications. Each of the below-listed applications is hereby incorporated herein by reference in its entirety:

This U.S. non-provisional application is a continuation in part of the following:

U.S. non-provisional application Ser. No. 19/185,738, inventor Darren Simmons et al. et al., entitled "INTERCHANGEABLE MODULAR DISINFECTION PLATFORM USING ELECTROCHEMICAL OZONE GENERATION AND CATALYTIC AIR PURIFICATION", filed Apr. 22, 2025; and U.S. non-provisional application Ser. No. 19/185,759, inventor Darren Simmons et al., entitled "INTERCHANGEABLE MODULAR DISINFECTION PLATFORM USING ELECTROCHEMICAL OZONE GENERATION AND CATALYTIC AIR PURIFICATION", filed Apr. 22, 2025;

U.S. non-provisional application Ser. No. 19/036,758, inventor Gavin Hsu et al., entitled "AQUA-OZONE HYGIENIZATION", filed Jan. 24, 2025; and U.S. non-provisional application Ser. No. 19/037,391, inventor Gavin Hsu et al., entitled "AQUA-OZONE HYGIENIZATION", filed Jan. 27, 2025;

U.S. non-provisional application Ser. No. 18/966,217, inventor Gavin Hsu et al., entitled "AIR DEODORIZING SYSTEM AND METHOD UTILIZING AQUEOUS OZONE AND CATALYTIC COMPONENTS FOR ENHANCED AIR QUALITY", filed Dec. 3, 2024;

U.S. non-provisional application Ser. No. 18/919,605, inventor Darren Simmons et al., entitled "IMMERSION CONTAINER FOR TREATING PRODUCE WITH AN OZONATED CONCENTRATE LIQUID", filed Oct. 18, 2024;

U.S. non-provisional application Ser. No. 18/646,394, inventor Darren Simmons et al., entitled "AQUEOUS OZONE FLOOR DISINFECTION SYSTEM", filed Apr. 25, 2024; and U.S. non-provisional application Ser. No. 19/052,935, inventor Darren Simmons et al., entitled "HYGIENIZATION GENERATOR FOR INTEGRATED AQUEOUS OZONE AND ALKALINE WATER PRODUCTION", filed Feb. 13, 2025; and U.S. non-provisional application Ser. No. 19/052,951, inventor Darren Simmons et al., entitled "HYGIENIZATION GENERATOR FOR INTEGRATED AQUEOUS OZONE AND ALKALINE WATER PRODUCTION", filed Feb. 13, 2025.

TECHNICAL FIELD OF THE INVENTION

This invention relates to ozone-based disinfection systems for refrigerated environments, and more specifically to systems and methods for purifying air and disinfecting water pathways within ice machines, refrigerators, and other cold storage enclosures. The invention includes an electrolytic ozone generator configured to produce gaseous and aqueous ozone from water, an air circulation subsystem to deliver oxidizing airflow within a refrigerated space, and a titanium dioxide-coated surface to reduce residual ozone concentration to levels compliant with human exposure safety limits. The invention also relates to methods for operating the system in disinfection and purification modes, optionally including automated door locking, sensor-based safety control, and waterline treatment for ice or water dispensers. The system is adaptable for integration into commercial, residential, and industrial refrigeration applications requiring improved hygiene, microbial control, and compliance with food safety and indoor air quality standards.

BACKGROUND OF THE INVENTION

Before our invention, disinfection systems designed for air treatment, refrigerated spaces, and aqueous ozone delivery suffered from a variety of functional and practical shortcomings that limited their effectiveness, adaptability, and ease of use.

In the context of general-purpose air disinfection, conventional systems were often built as closed, non-modular units with fixed configurations. These systems lacked the flexibility to accommodate varying installation environments or operational requirements. Many prior designs could not be easily adapted for use in different physical spaces or integrated with additional disinfection capabilities such as water treatment or humidity control. As a result, users were forced to install multiple specialized devices to achieve comprehensive sanitation coverage, which increased complexity, maintenance burden, and cost. Further, many air treatment systems operated with little regard for human safety—either generating ozone without a reliable mechanism to reduce residual concentrations or failing to regulate airflow treatment zones effectively. These issues were particularly problematic in environments where safe reentry timing and real-time ozone level reduction were critical.

In refrigerated spaces such as walk-in refrigerators, commercial freezers, and consumer-grade appliances, disinfection systems presented additional challenges. Some earlier systems attempted to use ozone as a disinfectant within refrigerated compartments, but often did so in an uncontrolled or continuous manner, leading to accumulation of ozone to unsafe levels for humans or for food preservation. There was typically no mechanism for transitioning between a high-ozone disinfection mode and a low-ozone purification mode. This lack of dynamic control raised safety and regulatory concerns, especially in environments subject to Occupational Safety and Health Administration (OSHA) or food safety standards. Furthermore, earlier systems generally did not include features such as door-locking mechanisms, ozone degradation pathways, or integration with ozone sensors, making them difficult to operate safely in occupied or intermittently accessed refrigerated environments. These systems also commonly overlooked the need to disinfect associated water systems, such as those used in ice makers and water dispensers, resulting in incomplete sanitization.

With respect to water supply for ozone generation, existing systems relied heavily on permanent plumbing connections, pressure-driven refill systems, or open reservoirs that were prone to contamination. Such solutions posed clear limitations in portable or mobile use cases, or in installations where plumbed water was not readily available. Manual refill methods were often cumbersome, introducing risk of user error or microbial contamination. Sealed, disposable water cartridges, if used at all, lacked intelligent tracking or system interlocks to prevent ozone generation in the absence of a valid water source. Many systems offered no way to detect when a cartridge was empty, misaligned, or improperly installed, which could compromise both safety and disinfection efficacy. These limitations significantly reduced the practicality of earlier ozone systems for non-industrial users, mobile service environments, or low-maintenance applications.

Prior systems also typically failed to incorporate smart control technologies capable of monitoring operational metrics, transmitting data, or responding to real-time feedback. There was little support for remote monitoring, geolocation, compliance logging, or centralized system management—capabilities now expected in modern, connected disinfection platforms. Without these features, maintenance scheduling, regulatory reporting, and system diagnostics were left to manual inspection or guesswork, reducing reliability and increasing the burden on technicians and users.

The cumulative effect of these shortcomings—rigid architecture, limited safety control, poor adaptability, and lack of user-friendly maintenance—meant that prior disinfection systems were often underutilized or avoided entirely in environments where they could have provided meaningful health and sanitation benefits. These gaps, particularly in high-risk or dynamic use environments, created a long-standing and unmet need for a versatile, intelligent, and modular approach to ozone-based air and water disinfection.

For these reasons and shortcomings, as well as other reasons and shortcomings not addressed by prior approaches, there is a long-felt need that gives rise to the present invention.

SUMMARY OF THE INVENTION

The shortcomings of the prior art are overcome and additional advantages are provided through the provision of a refrigerated space ozone-based disinfection system configured to purify air, disinfect surfaces, and treat water pathways using both gaseous and aqueous ozone. In one embodiment, the system comprises a purification configuration having an air circulation subsystem and a titanium dioxide-coated surface. The system also includes an electrolytic ozone generator that produces gaseous ozone from water, mixes the ozone with air from the refrigerated space to create an oxidizing environment, and then neutralizes excess ozone before returning air to the space. This architecture enables dynamic operation between disinfection and purification modes while maintaining ozone concentration at human-safe levels.

In another embodiment, the system includes sensor-controlled airflow recirculation and ozone degradation pathways, enabling the system to transition between disinfection and purification cycles under the control of a programmable controller. This enables safe operation within intermittently occupied environments like walk-in coolers or consumer refrigerators.

In a further embodiment, the system is configured to route ozonated water to internal plumbing components of an ice maker or water dispenser within the refrigerated appliance. By delivering aqueous ozone to these lines and combining it with air disinfection, the system ensures a comprehensive hygiene profile throughout the refrigerated environment. These improvements overcome prior limitations by supporting air, surface, and waterline sanitation within a confined and temperature-controlled enclosure.

Additional shortcomings of the prior art are overcome and additional advantages are provided through the provision of a refrigerated space ozone-based disinfection system configured to purify air, disinfect surfaces, and treat water pathways using both gaseous and aqueous ozone. In one embodiment, the system comprises a purification configuration having an air circulation subsystem and a titanium dioxide-coated surface. The system also includes an electrolytic ozone generator that produces gaseous ozone from water, mixes the ozone with air from the refrigerated space to create an oxidizing environment, and then neutralizes excess ozone before returning air to the space. This architecture enables dynamic operation between disinfection and purification modes while maintaining ozone concentration at human-safe levels.

In another embodiment, the system includes sensor-controlled airflow recirculation and ozone degradation pathways, enabling the system to transition between disinfection and purification cycles under the control of a programmable controller. This enables safe operation within intermittently occupied environments like walk-in coolers or consumer refrigerators.

In a further embodiment, the system is configured to route ozonated water to internal plumbing components of an ice maker or water dispenser within the refrigerated appliance. By delivering aqueous ozone to these lines and combining it with air disinfection, the system ensures a comprehensive hygiene profile throughout the refrigerated environment. These improvements overcome prior limitations by supporting air, surface, and waterline sanitation within a confined and temperature-controlled enclosure.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 4 illustrates one example of a modular ozone-based disinfection system configured to purify air, disinfect surfaces, and optionally disinfect water lines of an ice maker or refrigerator water dispenser;

FIG. 9 illustrates one example of an ozone disinfection database structure;

FIG. 12-14 illustrate examples of a method of performing disinfection using a modular ozone-based disinfection system;

FIG. 15 illustrate exemplary embodiments of a method of performing disinfection using a modular ozone-based disinfection system that can be interchangeable with the methods of the present invention;

FIGS. 16-18 illustrate examples of a method of purifying air in a refrigerated space using an ozone-based disinfection system;

FIGS. 19A-19B illustrate exemplary embodiments of a method of purifying air in a refrigerated space using an ozone-based disinfection system that can be interchangeable with the methods of the present invention;

FIG. 20-22 illustrate examples of a method of performing disinfection using a modular ozone-based disinfection system having a replaceable water cartridge; and FIGS. 23A-23B illustrate exemplary embodiments of a method of performing disinfection using a modular ozone-based disinfection system having a replaceable water cartridge that can be interchangeable with the methods of the present invention.

Figure 1:
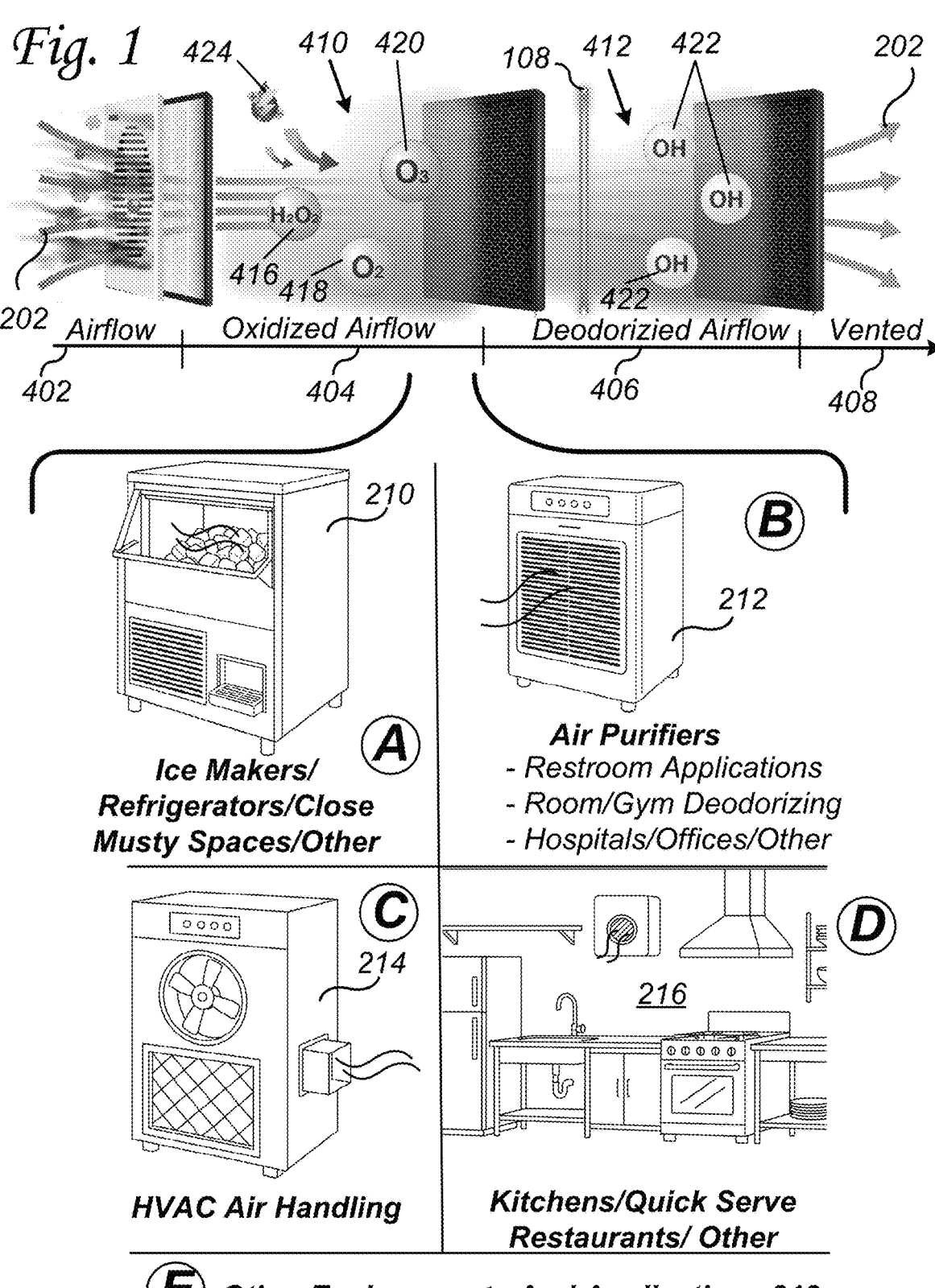
FIG. 1 illustrates examples of applications of a modular ozone-based disinfection system.

The detailed description explains the preferred embodiments of the invention, together with advantages and features, by way of example with reference to the drawings.

DETAILED DESCRIPTION OF THE INVENTION

The following detailed description is provided to convey an understanding of the present invention by illustrating various non-limiting examples and embodiments. While specific configurations and functional arrangements are described to facilitate clarity, the present invention is not limited to the exact forms disclosed, and may be implemented in various alternative or equivalent ways depending on the application context and system requirements.

The present disclosure introduces an integrated ozone-based disinfection and purification system, adaptable across a range of environments. These include, but are not limited to, modular installations (such as portable or standalone systems), confined refrigerated spaces (such as ice machines and refrigerator enclosures), and compact implementations using sealed, replaceable cartridges for convenience and safety.

Conventional air purification and disinfection systems often rely on single-mode chemical treatments, passive filtration, or limited ultraviolet exposure techniques. Such systems frequently fall short in environments requiring dynamic cycling between disinfection and safe air return, particularly in compact or human-occupied spaces where residual chemical agents like ozone must be safely neutralized before reentry.

In the present invention, the term "modular ozone-based disinfection system" is intended to mean a system comprising at least a purification configuration and one or more of a tank configuration, dehumidifier configuration, and/or source water configuration, wherein the components are structurally or functionally interchangeable or operatively connectable to create ozone from water for air and/or surface disinfection, optionally with catalytic ozone neutralization.

In the present invention, the term "purification configuration" is intended to mean a configuration comprising an air circulation subsystem and one or more ozone treatment components, including at least a titanium dioxide-coated surface, configured to receive airflow, expose the airflow to an oxidizing environment including ozone, and reduce residual ozone to a level compliant with applicable human exposure safety limits.

In the present invention, the term "tank configuration" is intended to mean a water storage system for delivering water to an ozone generation subsystem, and can include a fixed tank or a housing configured to receive a replaceable water cartridge.

In the present invention, the term "dehumidifier configuration" is intended to mean a subsystem operatively connected to the tank configuration and configured to extract water from ambient air using components such as a condenser coil, fan, and collection reservoir.

In the present invention, the term "source water configuration" is intended to mean a water input subsystem configured to connect to an external pressurized or non-pressurized water line and supply water to the system through a fluid inlet, optionally including pressure regulation or backflow prevention.

In the present invention, the term "replaceable water cartridge" is intended to mean a sealed, removable container of water configured to deliver water to the ozone generation subsystem, and optionally configured with alignment features, usage tracking, and interlocks to prevent operation when depleted or improperly installed.

In the present invention, the term "replaceable water cartridge status" is intended to mean an indicator or condition derived from usage tracking, alignment verification, or water volume remaining, which determines whether the cartridge is suitable for continued use, replacement, or system disabling.

In the present invention, the term "electrolytic ozone generator" is intended to mean an electrochemical component configured to generate ozone gas and/or aqueous ozone from water using an electrolysis reaction, optionally incorporating ion exchange material to enhance ozone production efficiency or purity.

In the present invention, the term "ozonated concentrate liquid" is intended to mean an aqueous solution of water and dissolved ozone generated by the system, which may be used for disinfection of water lines, ice machines, or dispensing systems.

In the present invention, the term "titanium dioxide-coated surface" is intended to mean a surface or substrate coated with $TiO_2$ or a photocatalytic variant thereof, configured to promote decomposition of ozone or other oxidants in the presence of light or airflow, thereby reducing airborne ozone levels through photocatalytic oxidation.

In the present invention, the term "manganese dioxide treatment module" is intended to mean a component comprising manganese dioxide ($MnO_2$) configured to react with ozone to produce hydroxyl radicals ($\cdot OH$), enhancing oxidation and disinfection within the airflow path.

In the present invention, the term "controller" is intended to mean an electronic control system comprising a microcontroller, memory, and communication interface, configured to regulate operation of the system based on sensor feedback, stored profiles, remote commands, or preprogrammed disinfection modes.

In the present invention, the term "occupied environment" is intended to mean any space in which a person may be physically present during or after a treatment cycle, including but not limited to residential rooms, commercial kitchens, refrigerated compartments, walk-in coolers, offices, or vehicle interiors.

In the present invention, the term "disinfection mode" is intended to refer to a mode of system operation wherein ozone concentrations are elevated to actively disinfect air, surfaces, or water pathways, whereas "purification mode" refers to an operational state where residual ozone is neutralized or reduced before air is discharged to ensure safety for reentry into the treated environment.

In the present invention, the term "ozone concentration has been reduced to a level compliant with applicable human exposure safety limits" is used in a non-limiting sense to refer to any ozone concentration in air that falls at or below recognized safety thresholds for human exposure as defined by applicable regulatory, occupational, or environmental health standards. These thresholds can include, for example, the Occupational Safety and Health Administration (OSHA) permissible exposure limit (PEL) of 0.1 parts per million (ppm) averaged over an 8-hour work shift, or the American Conference of Governmental Industrial Hygienists (ACGIH) threshold limit value (TLV) of 0.05-0.1 ppm depending on the application. The system may monitor and reduce ozone concentrations to well below these values prior to discharging treated air into occupied spaces, ensuring safety in a wide range of use environments including healthcare, food service, and public-facing facilities.

In some embodiments, the ozone concentration may be measured using an internal ozone sensor in coordination with the titanium dioxide-coated surface or other ozone-neutralizing components. In other embodiments, the system may rely on fixed dwell times, airflow treatment rates, or calibrated degradation curves to passively or actively reduce ozone levels prior to venting. The language is intended to encompass all such implementations in which the residual ozone in the discharged air has been mitigated to a level that conforms with applicable safety standards for human exposure.

Moreover, traditional systems often lack flexible modularity, resulting in designs that are bulky, difficult to service, or incompatible with alternative water sources such as atmospheric condensate or line-fed water. These limitations can restrict deployment across various industries, including food service, healthcare, and residential or commercial heating, ventilation, and air conditioning (HVAC).

To address these challenges, the present invention introduces a versatile, multi-configuration disinfection system that leverages the oxidative power of ozone in conjunction with advanced catalytic reduction materials. The system comprises at least one purification configuration (responsible for airflow treatment), coupled with one or more of the following:

A tank configuration for storing water used to generate ozone,

A dehumidifier configuration for extracting water from ambient air, and

A source water configuration for receiving water from an external line.

This modular framework supports scalable design across different environments. Each configuration is designed to be integrated, stacked, or operationally linked depending on space, usage frequency, and water availability. Ozone may be delivered in both gaseous form for air treatment and aqueous form for surface and waterline disinfection.

Ozone Interaction with Catalytic Surfaces

A core scientific principle of the present invention is the conversion of ozone ($O_3$) into safer or more reactive species via interaction with catalytic materials.

Titanium Dioxide ($TiO_2$): When ozone-laden air is directed across a titanium dioxide-coated surface, particularly under conditions of UV exposure or high airflow activation energy, photocatalytic oxidation occurs. This reaction breaks down residual ozone into oxygen ($O_2$) while simultaneously oxidizing organic and microbial contaminants in the air. This mechanism enables the system to maintain high disinfection efficiency during ozone generation, followed by rapid ozone neutralization to support safe reentry or continuous operation in occupied environments.

Manganese Dioxide ($MnO_2$): In certain configurations, gaseous ozone may be routed across a manganese dioxide treatment module. $MnO_2$ catalyzes a reaction that converts ozone into hydroxyl radicals ($\cdot OH$), which exhibit broad-spectrum antimicrobial activity. This conversion amplifies the disinfection capability while minimizing excess ozone. Hydroxyl radicals rapidly react with airborne organic compounds, biofilms, and pathogens, making this approach highly effective in confined or hard-to-clean spaces.

Modular System Configuration

In the first embodiment, the system is implemented using modular components that can be mixed and matched to suit installation requirements. At a minimum, the purification configuration is included to receive airflow, generate oxidizing treatment conditions using gaseous ozone, and subsequently neutralize residual ozone using a titanium dioxide-coated surface. Depending on the selected form, the tank configuration may include a fixed reservoir or a replaceable water cartridge, each capable of delivering water to the electrolytic ozone generator.

When atmospheric water is available, a dehumidifier configuration may be coupled to the tank configuration to autonomously extract and deliver water. In environments with a pressurized supply, a source water configuration may be added, enabling the system to operate in continuous ozone generation and purification modes. Any or all of these modules may be combined depending on the target application and may be housed in vertically stacked or adjacent arrangements.

Refrigerated Space Configuration

In a second embodiment, the system is adapted for use in refrigerated environments, such as ice machines or food storage compartments. A key advantage of the present invention is its ability to disinfect enclosed spaces using ozone, then internally neutralize residual ozone prior to releasing air back into the refrigerated area.

In this configuration, the controller coordinates between two operational modes:

A disinfection mode, where ozone is directed into the refrigerated space to raise the ambient ozone concentration for a defined period; and A purification mode, where the air is recirculated through the system, passed across a titanium dioxide surface, and returned after the ozone concentration is reduced to levels compliant with human exposure guidelines.

Additionally, aqueous ozone may be dispensed into ice-making water lines or drinking water dispensers for internal sanitization. Optional components include a manganese dioxide treatment module for producing hydroxyl radicals and an electronically controlled locking mechanism that prevents user access during disinfection cycles.

Replacement Cartridge Configuration

In a third embodiment, the system utilizes a sealed, replaceable water cartridge as the sole or primary water source. This version is particularly suitable for consumer, healthcare, and field applications where system portability is desired and/or manual refilling or plumbing access is not feasible. The purification configuration operates as in the prior embodiments, directing ozone-treated air through titanium dioxide and safely discharging the air after ozone levels are reduced.

Cartridge usage may be monitored via a microcontroller and sensor system, with alerts transmitted to a remote processing resource or displayed on a local interface. This ensures predictable operation and supports regulatory compliance in critical environments.

Turning now to the drawings in greater detail, it will be seen that in FIG. 1 there is illustrated examples of applications of a modular ozone-based disinfection system 100 configured for flexible deployment across multiple disinfection and purification environments. In an exemplary embodiment, system 100 is shown installed in various use cases, including applications involving refrigerated equipment 210, HVAC air handlers 214, commercial kitchens 216, public restrooms/gyms/hospitals/offices/other 212, and other environment and applications 218.

The figure illustrates the adaptability of the modular ozone-based disinfection system 100 for various operational environments while maintaining a consistent core treatment mechanism built around ozone-based disinfection and catalytic purification. The system's ability to integrate with different air and water sources, control architectures, and communication platforms allows it to scale from standalone units to distributed enterprise deployments.

In this regard, the modular ozone-based disinfection system 100 can be positioned adjacent to or within the target treatment environment. For example, in the case of refrigerated equipment 210 such as walk-in coolers or ice machines, the modular ozone-based disinfection system 100 may be installed in the upper corner of the enclosure or externally ducted to circulate air through the internal space. Similarly, the modular ozone-based disinfection system 100 can be ducted into or embedded within a centralized HVAC air handler 214, thereby allowing oxidizing treatment of recirculated airflow while maintaining ozone concentrations at or below regulatory thresholds.

In commercial kitchen applications 218, public restroom installations 212, and other similar applications, the modular ozone-based disinfection system 100 provides continuous or programmable disinfection, optionally integrated with ambient air sensors 512, door-activated triggers, or idle-time ozone boost cycles. In healthcare settings such as hospital patient rooms 212, and other similar applications, the modular ozone-based disinfection system 100 can be configured to operate in coordination with external monitoring devices, such as a remote data processing resource 702 or a computing device 732, which can receive status updates, cycle logs, or cartridge replacement alerts.

Each instance of the modular ozone-based disinfection system 100 includes at least a purification configuration 170, which houses an air circulation subsystem 104 and an ozone treatment module. Depending on the embodiment, a tank configuration 172 may also be included and may take the form of either a fixed water tank or a replaceable water cartridge 126. These configurations are fluidly coupled to an electrolytic ozone generator 516, which generates gaseous ozone from water.

The generated gaseous ozone can be directed through the airflow path of purification configuration 170 to form an oxidizing treatment environment that disinfects the airflow. The airflow is then exposed to a titanium dioxide-coated surface 110, which promotes the decomposition of residual gaseous ozone through photocatalytic oxidation, to a level compliant with applicable human exposure safety limits before discharge. In certain embodiments, the modular ozone-based disinfection system 100 can also include a manganese dioxide treatment module 112 that reacts with gaseous ozone to form hydroxyl OH radicals for enhanced chemical disinfection. This dual-stage approach allows the modular ozone-based disinfection system 100 to deliver high-efficacy treatment during active disinfection while ensuring safe air output suitable for return to occupied environments.

The modular design enables flexible assembly depending on the site-specific requirements, application, location, equipment cost budget, and other factors. As shown in the various illustrated applications, the system may further include:

A dehumidifier configuration 174 that extracts water from ambient air and delivers it to the tank configuration 172.

A source water configuration 176 for continuous supply from a pressurized or non-pressurized external water line.

A controller 500, which comprises a microcontroller 502, a memory 504, and a communication interface 508. The controller 500 can be programmed to implement various modes of operation and treatment cycles by coordinating system modes, monitoring environmental and internal conditions via sensors 512, optionally communicating with external resources 702/732/and others over wireless, local area networks (LAN), wide area networks (WAN), global networks 700, and other communication methods. The Internet can be a global network 700.

In some applications, particularly in healthcare, food service, and other suitable installations, the modular ozone-based disinfection system 100 can record disinfection activity, ozone levels, or cartridge usage data in a database 800, which may store notification records 814, geofencing records 806, and technician service logs for maintenance and compliance.

Figure 2:
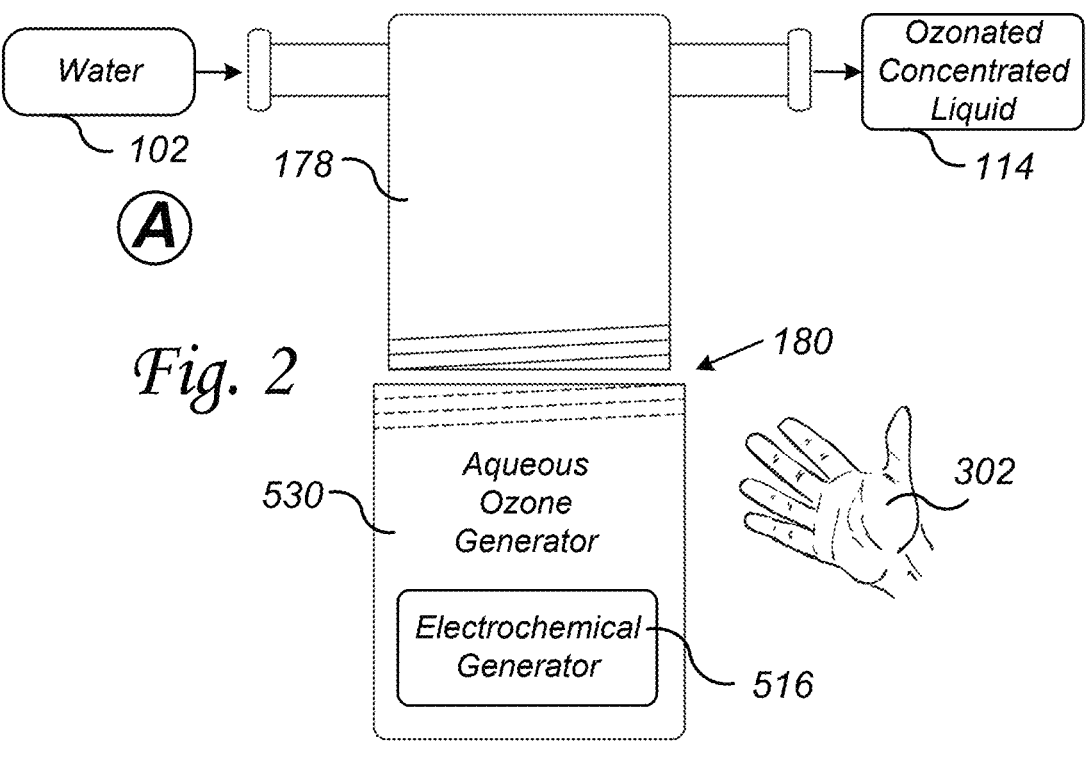
FIG. 2 illustrates one example of an aqueous ozone generator connected in a removable manner to a plumbed housing.

Referring to FIG. 2, there is illustrated one example of an aqueous ozone generator 530 connected, in a removable manner, to a plumbed housing 150 of the modular ozone-based disinfection system 100. In an exemplary embodiment, the aqueous ozone generator 530 can be removably installed within or adjacent to the plumbed housing 150 using a modular interface or quick-connect system that enables cartridge exchange, system upgrades, or technician access.

The modular ozone-based disinfection system's 100 ability to modularly integrate aqueous and gaseous ozone production from the same base unit allows a single device to deliver water treatment, surface disinfection, and air purification depending on installation context and operational programming. As shown in the figure, the modular ozone-based disinfection system 100 supports flexible maintenance without disrupting connected fluid circuits, offering clear advantages in reliability, safety, and total cost of ownership.

The aqueous ozone generator 530 can comprise an electrolytic ozone generator 516, which utilizes an ion exchange material 534 to generate ozone through electrolysis. This configuration allows the system to produce both ozonated concentrate liquid 114 and gaseous ozone from water. The ozonated concentrate liquid 114 can be routed through internal or external water lines for disinfection of refrigerator water dispensers, ice maker supplies, and other hygienically sensitive plumbing.

The plumbed housing 150 is configured to remain fixed within the system's fluid flow circuit, allowing consistent routing of water to and from the aqueous ozone generator 530 while providing a service access point for ozone-generation components. Plumbed housing 150 includes a serviceable interface 180 that permits the replacement of consumable components such as the electrolytic ozone generator 516 and the ion exchange material 534, which can degrade over time or with extensive use. These consumables are secured in place using a fastener 108, which can be a threaded fastener, snap-lock mechanism, twist-lock collar, or other suitable retaining device.

This arrangement allows technician 302 to safely and efficiently service the equipment without disrupting or compromising the core plumbing infrastructure of the system. The fixed plumbed housing 150 ensures fluid tightness and pressure integrity, while still supporting routine maintenance, field replacement, or part upgrades.

Sensors such as sensor 512 can be used to monitor ozone output, fluid pressure, or conductivity, and report data to a microcontroller 502. The microcontroller 502 can adjust operational parameters or issue alerts to a computing device 732 or remote data processing resource 702. System location and service logs can optionally be tracked using a GPS module 514, facilitating automated technician dispatch or geofencing of sensitive deployment zones.

Figure 3A:
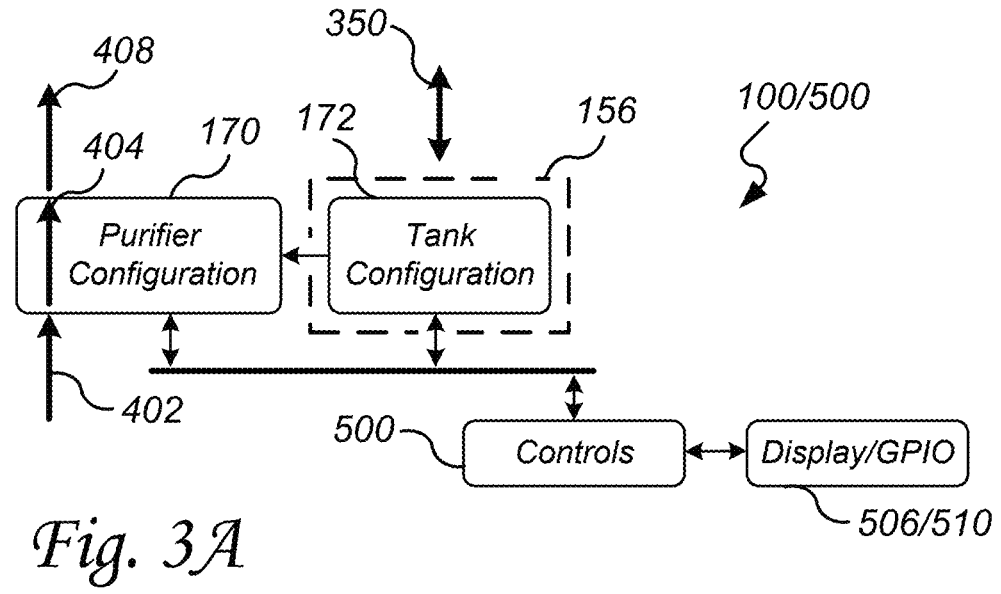
FIG. 3A illustrates one example of a modular ozone-based disinfection system which comprises a purification configuration and a tank configuration.

Referring to FIG. 3A, there is illustrated one example of a modular ozone-based disinfection system 100 comprising a purification configuration 170 operatively connected to a tank configuration 172. In an exemplary embodiment, this configuration represents a base modular arrangement for treating air using ozone generated from a water-based source.

The figure illustrates a foundational embodiment of the modular ozone-based disinfection system 100, providing effective and adaptable air purification while supporting both fixed and replaceable water sources in a highly serviceable form factor.

The purification configuration 170 includes an air circulation subsystem 104, such as one or more fans, configured to pull ambient air through the housing, mix the air with gaseous ozone generated within the system, and direct the air across a titanium dioxide-coated surface 110 to reduce residual ozone before discharge. This arrangement creates an oxidizing environment within the airflow path, enabling disinfection of airborne pathogens, volatile organic compounds (VOCs), and malodors while ensuring that the air released from the system is within acceptable safety limits for reentry into shared or enclosed environments.

In an exemplary embodiment of the modular ozone-based disinfection system 100, airflow enters the system through an inlet 402, where it is pulled into the housing by the air circulation subsystem 104, which can include one or more fans. The incoming air then proceeds along an airflow pathway 404, which is defined within the purification configuration 170. As the air travels through pathway 404, it is exposed to gaseous ozone injected or generated internally by the electrolytic ozone generator 516, creating an oxidizing environment for airborne contaminant reduction. The oxidizing airflow continues through the treatment chamber where it is directed across a titanium dioxide-coated surface 110 positioned within the airflow path. As the air passes this surface, a catalytic reaction occurs that decomposes residual ozone and other volatile organic compounds (VOCs), reducing the ozone to levels suitable for reentry into human-occupied environments. The purified and treated air is then expelled through the air outlet 408, completing the controlled flow loop. The overall architecture of the airflow pathway ensures that disinfection occurs in a contained, sequential manner, with treatment zones logically positioned between the inlet and outlet to optimize both ozone efficacy and post-treatment safety.

The tank configuration 172 supplies water to an electrolytic ozone generator 516, which utilizes an ion exchange material 534 to convert water into both gaseous ozone and ozonated concentrate liquid 114. In some embodiments, the tank configuration 172 comprises a fixed internal water reservoir. In other embodiments, it includes a housing configured to receive a replaceable water cartridge 126. The use of the cartridge 126 allows for sealed, pre-filled water supplies to be swapped in without manual refilling or plumbing, simplifying maintenance and improving hygiene—particularly in environments like clinics, office spaces, or residential use cases where trained service personnel may not be available.

This base modular configuration can be deployed in a variety of exemplary embodiments, including:

A portable room disinfection unit suitable for dormitories, conference rooms, or hotel applications;

A relocatable freestanding unit for use in healthcare waiting areas or public-facing lobbies;

A desktop or under-desk air treatment appliance in shared office environments or call centers;

A countertop appliance for use in food prep areas, nail salons, or personal care rooms;

A compact embedded module for appliance manufacturers seeking to integrate ozone disinfection in ice makers, beverage dispensers, or under-sink filtration systems and Numerous other environment, setting, and applications.

Compared to prior approaches, this purification configuration plus the tank configuration offers distinct advantages. Conventional systems often require direct plumbing, permanent reservoirs, or single-function filter media. In contrast, the present invention enables:

Flexible water sourcing, via either a fixed tank or sealed cartridge;

Modular servicing, where individual modules can be replaced or upgraded without disassembling the whole system;

Dual-mode ozone delivery, with aqueous or gaseous ozone available depending on operational requirements;

Integrated ozone neutralization, using a titanium dioxide-coated surface to break down excess ozone before air is returned to the treated environment; and Other features and benefits.

The use of a replaceable water cartridge 126 in particular allows for controlled dosing, eliminates user contact with raw water, and supports highly portable system designs—enabling reliable deployment in rental properties, mobile environments, or consumer markets.

The modular ozone-based disinfection system 100 operations can be monitored and controlled via a controller 500 which comprises a microcontroller 502, which coordinates fan cycles, ozone generation timing, and safety interlocks among other things. Real-time feedback can be provided by sensors 512, and data can be relayed to a remote data processing resource 702 or computing device 732 for maintenance logging or regulatory compliance. Optional integration with GPS module 514 and cloud services enables location tracking, technician dispatch, geofencing capabilities in enterprise deployments, or other applications.

Figure 3B:
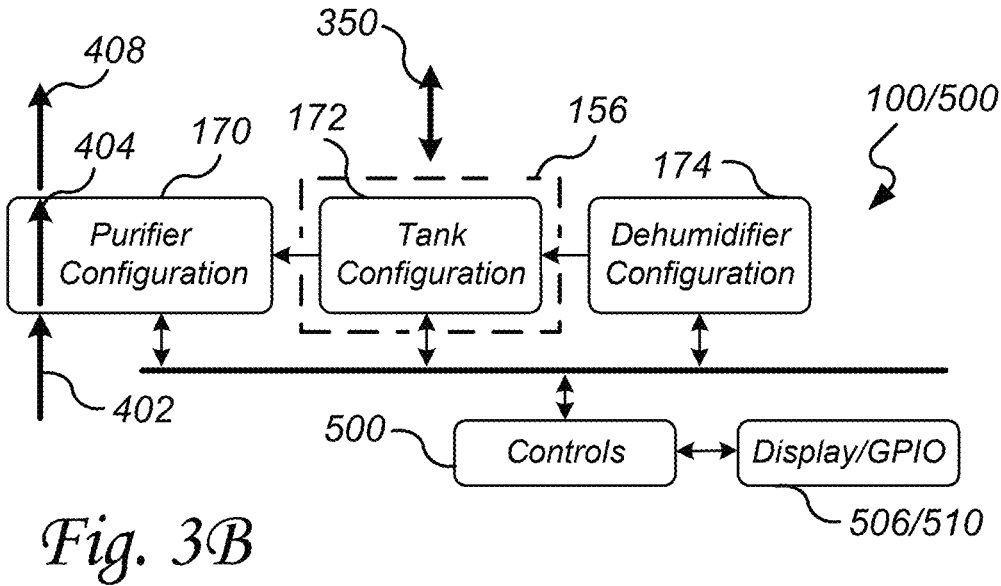
FIG. 3B illustrates one example of a modular ozone-based disinfection system which comprises a purification configuration, a tank configuration, and a dehumidifier configuration.

Referring to FIG. 3B, there is illustrated one example of a modular ozone-based disinfection system 100 which comprises a purification configuration 170, a tank configuration 172, and a dehumidifier configuration 174. This embodiment expands on the configuration shown in FIG. 3A by incorporating an autonomous water sourcing module, enabling continuous or replenishable ozone generation without requiring plumbing or manual refilling.

The figure illustrates an advanced embodiment of the modular ozone-based disinfection system 100, wherein the integration of the dehumidifier configuration 174 enables water-independent, autonomous disinfection cycles, significantly enhancing system deployability in settings where water access or maintenance availability is limited In an exemplary embodiment, purification configuration 170 is configured to receive ambient air, mix the air with gaseous ozone produced by the system, and pass the oxidizing airflow across a titanium dioxide-coated surface 110 for catalytic decomposition of excess ozone. The air circulation subsystem 104 includes one or more fans that pull air into the system and discharge treated air with ozone concentrations reduced to levels suitable for reentry into an occupied environment. The air purification process supports both continuous operation and programmable disinfection cycles, controlled by a microcontroller 502 and informed by environmental inputs from one or more sensors 512.

The tank configuration 172 is positioned beneath or adjacent to the purification configuration 170 and serves as the primary water supply for an electrolytic ozone generator 516. The ozone generator 516 uses ion exchange material 534 to convert water into gaseous ozone and/or ozonated concentrate liquid 114. In this embodiment, the tank configuration 172 can either contain a fixed reservoir or be configured to receive a replaceable water cartridge 126, depending on servicing preferences and system portability requirements.

The addition of the dehumidifier configuration 174 enables the system to autonomously extract water from ambient air and deliver it to the tank configuration 172. In one embodiment, the dehumidifier configuration 174 includes a condenser coil 124, fan assembly 104, and collection reservoir 108, which work together to condense moisture from air drawn through the system and redirect the collected water into the tank 126 for ozone generation. This arrangement eliminates the need for manual water refills or plumbed water lines, making the system ideal for installation in remote, mobile, or infrastructure-limited environments.

Exemplary applications of this embodiment include:

Portable or relocatable disinfection units for emergency shelters, clean rooms, or field hospitals;

Public transit or fleet vehicle air treatment systems, where external plumbing is not practical;

Smart residential appliances that autonomously maintain water levels and disinfection capacity;

Industrial safety-critical locations, where maintenance-free operation is required over extended periods; and Numerous other application The combined modular architecture allows each of the purification configuration 170, tank configuration 172, and dehumidifier configuration 174 to be assembled in a stacked or side-by-side enclosure, as appropriate for the installation footprint. Fluid interconnections between modules can be made via quick-connect fittings or internal channels, and electrical signals can be routed through a unified harness to controller 500. The controller is configured to regulate ozone generation, initiate dehumidification based on tank water level, and coordinate fan speed or cycle duration according to programmed operational profiles.

An optional global positioning system (GPS) module 514 can support geofenced deployment, service technician 302 routing, or regional compliance tracking. Status reports, alerts, and maintenance data can be transmitted via network communication to a computing device 732 or remote data processing resource 702.

Figure 3C:
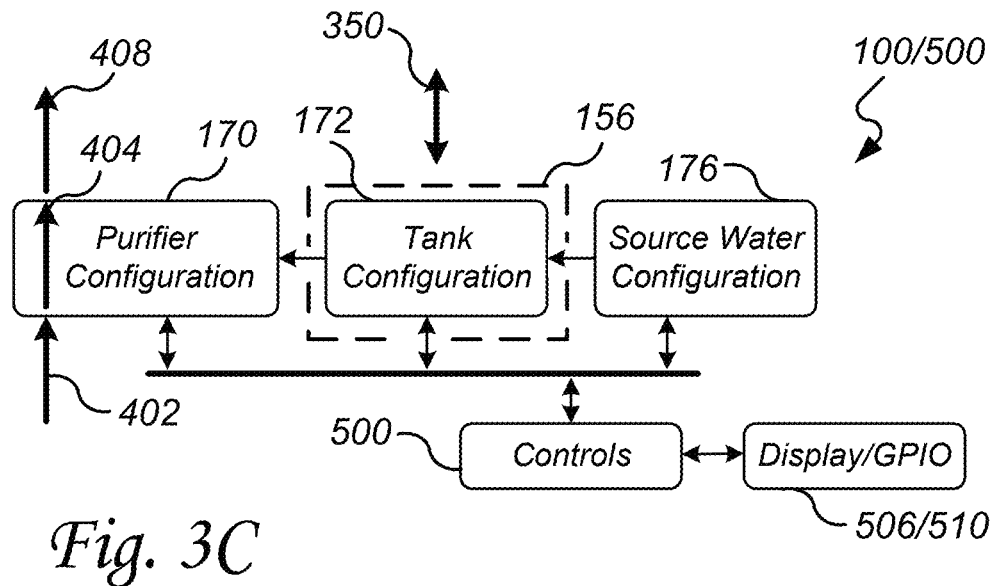
FIG. 3C illustrates one example of a modular ozone-based disinfection system which comprises a purification configuration, a tank configuration, and a source water configuration.

Referring to FIG. 3C, there is illustrated one example of a modular ozone-based disinfection system 100 comprising a purification configuration 170, a tank configuration 172, and a source water configuration 176. This embodiment demonstrates how the system can be modularly configured to draw water from a continuous external supply that is pressurized or non-pressurized, eliminating the need for onboard water storage or atmospheric water extraction.

The figure highlights how the modular ozone-based disinfection system 100 can be adapted for continuous operation in fixed installations where utility connections are available, offering a scalable disinfection solution that reduces consumables while maintaining flexible deployment options.

In an exemplary embodiment, the source water configuration 176 includes a fluid inlet 182 and connection assembly configured to couple to an external water line. The inlet can include components such as a pressure regulator, flow control valve, and backflow prevention mechanism, ensuring water is safely delivered to the tank configuration 172 without introducing contamination or pressure instability. The collection reservoir 108 in this embodiment functions as a buffer reservoir that receives water from the source water configuration 176 and supplies it to the tank configuration 172 which in turn supplies it to the electrolytic ozone generator 516, which uses ion exchange material 534 to generate gaseous ozone and/or aqueous ozonated concentrate liquid 114.

The generated gaseous ozone is introduced into the purification configuration 170, where it is mixed with incoming air along an internal airflow path. Air enters the system through an inlet 402, drawn in by a fan assembly 104 that forms part of the air circulation subsystem. From the inlet, the air proceeds along an airflow path 404, where it is combined with ozone to create an oxidizing treatment zone. This airflow path can include an ozone injection chamber or passage area where ozone concentration and contact time are controlled. Downstream, the oxidizing air is directed across a titanium dioxide-coated surface 110, where photocatalytic oxidation reactions reduce the ozone concentration and neutralize volatile organic compounds (VOCs), bacteria, and odors.

The treated airflow is then discharged from the system through air outlet 408, completing the disinfection cycle. The air discharged through outlet 408 is purified and has a significantly reduced ozone concentration-suitable for release into an occupied or enclosed environment such as a refrigerated space, food preparation area, clean rooms, and other areas.

This embodiment is especially well-suited for environments where a dedicated plumbing line is available, such as:

Commercial kitchens or foodservice areas, where disinfection and continuous operation are critical;

Medical cold storage such as drug or vaccine refrigeration units, where microbial control must be maintained with minimal manual intervention;

HVAC-integrated installations, where a reliable water line is available and frequent servicing is not feasible; or Numerous other applications.

The use of the source water configuration 176 provides long-term operational autonomy by removing reliance on water cartridges or dehumidification, while still allowing ozone generation to be precisely managed by the controller 500. The controller 500 can dynamically control fan speed, ozone dosage, and purification cycle timing, and may interface with sensors 512, remote data processing resource 702, and computing device 732 for real-time feedback and remote servicing. Optional GPS module 514 can be included for geofencing, asset tracking, and regional compliance reporting.

Figure 3D:
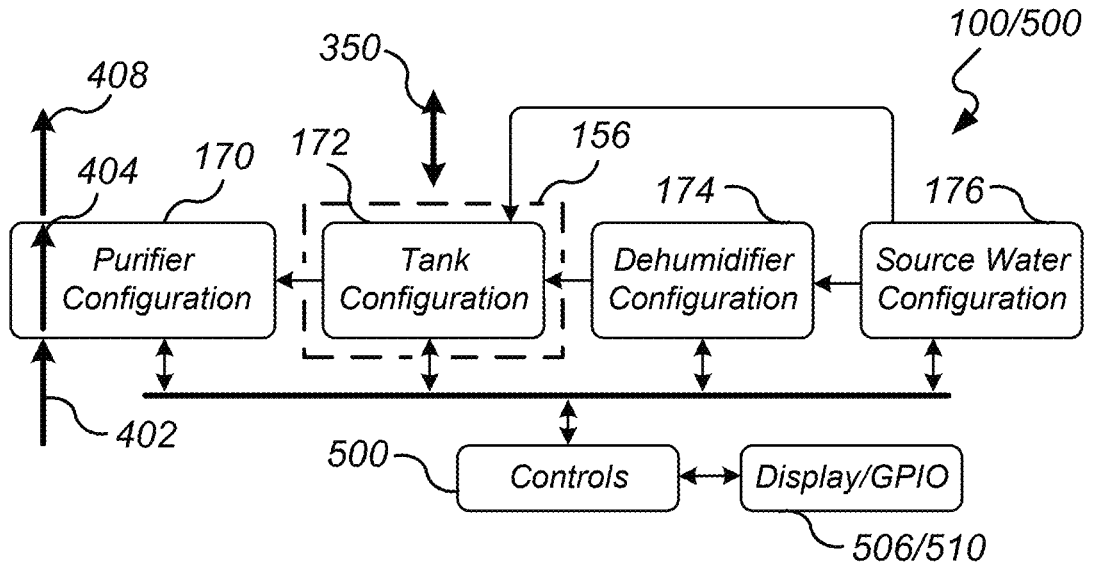
FIG. 3D illustrates one example of a modular ozone-based disinfection system which comprises a purification configuration, a tank configuration, a dehumidifier configuration, and a source water configuration.

Referring to FIG. 3D, there is illustrated one example of a fully integrated embodiment of a modular ozone-based disinfection system 100, comprising a purification configuration 170, a tank configuration 172, a dehumidifier configuration 174, and a source water configuration 176. This embodiment demonstrates the complete modular architecture of the system, combining multiple water-sourcing options to maximize flexibility, autonomy, and resilience in various operational environments.

The figure exemplifies how the modular ozone-based disinfection system 100 can be tailored to meet diverse needs using interchangeable or cooperative water-sourcing modules while maintaining a unified purification function. Each configuration module operates independently but is integrated through intelligent control, providing both reliability and adaptability in a wide range of deployment scenarios.

In this embodiment, ambient air is drawn into the purification configuration 170 through an air inlet 402 via the action of the air circulation subsystem 104, which can include a fan or blower. The incoming air is directed along an internal airflow path 404, where it is mixed with gaseous ozone generated within the system to form an oxidizing environment for disinfection. The oxidizing airflow is then directed across a titanium dioxide-coated surface 110, positioned within the airflow path, which serves to reduce residual ozone and break down volatile organic compounds (VOCs) or airborne contaminants through photocatalytic oxidation. Treated air is then discharged through an air outlet 408, with the ozone concentration reduced to a level suitable for reentry into a human-occupied or otherwise enclosed environment.

The electrolytic ozone generator 516, which includes or is in fluid communication with ion exchange material 534, receives water from tank configuration 172 and uses electrochemical reactions to produce both gaseous ozone and ozonated concentrate liquid 114. The tank configuration 172 can comprise either a fixed reservoir tank 184 or a water source housing 156 adapted to receive a replaceable water cartridge 126.

Water is delivered to the tank configuration 172 through two potential sources:

A replaceable water cartridge 126;

A dehumidifier configuration 174, which includes a condenser coil 124, fan assembly 104, and collection reservoir 108, extracts moisture from ambient air and collects it for system use;

A source water configuration 176, which includes a fluid inlet system 182, allows water from an external continuous supply (e.g., plumbed utility line) to be introduced into the system. The source water configuration 176 can be fluidly connected to either the collection reservoir 108 or directly to the tank configuration 172. This dual-routing capability enables dynamic control over which water source is used based on environmental conditions, availability, or system preferences.

In operation, the collection reservoir 108 functions as an intermediate buffer, collecting water from the dehumidifier and optionally receiving supplemental water from the source water configuration 176. Collection reservoir 108 then supplies water to tank configuration 172, which provides it to the electrolytic ozone generator 516. Alternatively, the source water configuration 176 can directly feed tank 126 or fixed reservoir tank 184, bypassing the dehumidifier when needed.

A controller 500 orchestrates the operation of each configuration module, including ozone generation timing, fan speed, water source prioritization, and safety interlocks. It may execute preprogrammed disinfection profiles, respond to sensor input (e.g., from sensors 512, ozone sensor 522, humidity sensor 518, liquid level sensors 552, temperature sensors 556, or other system sensors), and communicate data to a remote data processing resource 702 or computing device 732. Integration of a GPS module 514 allows for location-based monitoring, technician tracking, and regulatory compliance enforcement.

This embodiment offers the highest level of autonomy and operational versatility. It is especially suited for long-term deployment in environments where service access is limited or where water conditions may vary. Example applications include:

Critical HVAC and hospital room integration with automated refill and air purification;

Walk-in refrigerated spaces or commercial ice machines that require multiple disinfection modes;

Transportable disinfection kiosks or freestanding air treatment towers with hands-off maintenance;

Remote field operations, where humidity and utility water access may fluctuate; and Numerous other applications.

Referring to FIG. 4, there is illustrated one example of a modular ozone-based disinfection system 100 configured to operate within or adjacent to refrigerated equipment 210, such as an ice machine, refrigerator, freezer, or other enclosed cold storage unit. In an exemplary embodiment, the modular ozone-based disinfection modular ozone-based disinfection system 100, in refrigerated equipment disinfection applications, uses intelligent airflow management (i.e. switchable purified air 408, gaseous ozone 414, and optionally OH hydroxyl radical enriched air 416), catalytic ozone decomposition, and optional aqueous circuit 418, to deliver a comprehensive and programmable solution for maintaining hygiene in refrigerated environments, far beyond the capabilities of filter-only or static ozone systems.

The present invention is designed to perform three complementary disinfection functions:

Air purification using gaseous ozone;

Surface disinfection using oxidizing airflow; and

Water line and ice bin disinfection using aqueous ozone.

The purification configuration 170 houses an internal air circulation subsystem 104, which draws ambient air from the refrigerated space into the system via an air inlet 402, propelling it along an airflow path 404. Within this pathway, the air is exposed to gaseous ozone 414 generated by the electrolytic ozone generator 516, forming an oxidizing treatment environment capable of neutralizing airborne pathogens, fungi, and odors. The treated air is then directed across a titanium dioxide-coated surface 110, where photocatalytic oxidation occurs to safely degrade residual ozone and volatile compounds. The air exits the system through an air outlet 408 as purified airflow 408 suitable for return to the refrigerated compartment.

In an exemplary embodiment, the modular ozone-based disinfection system 100 is configured to produce not just one, but multiple airflow types 422, including:

Purified air 408 (ozone-reduced air for continuous recirculation),

Ozone-rich air 414 (for short-term disinfection cycles), and

Hydroxyl-enriched air 416 (generated by passing ozone over a manganese dioxide treatment module 112, producing hydroxyl radicals).

The ability to switch between airflow types 422 gives the system a key advantage: it can cycle between oxidizing disinfection modes and safe purification modes, creating programmable treatment cycles that maximize efficacy while preserving air quality. For example, the system can elevate ozone levels during idle times for deep surface disinfection, then automatically transition to purified air recirculation before user access.

In addition to air treatment, the system includes an aqueous ozone circuit 418, fluidly coupled to the electrolytic ozone generator 516, which also uses ion exchange material 534 to generate ozonated concentrate liquid 114. The aqueous ozone circuit 418 is configured to route this ozonated water into one or more water lines 240 used by an ice maker or refrigerator water dispenser. This enables the system to sanitize internal tubing, valves, and dispensing nozzles, providing protection against biofilm, microbial buildup, and mold—common failure modes in high-use beverage or ice dispensing systems.

As shown in the figure, the ice bin or dispenser produces ice cubes 420, which can be exposed to either purified air or ozone-rich air, depending on system mode. The controller 500 manages transitions between operating states, water line flushing, ozone generation, and cycle timing, using feedback from sensors 512 and external scheduling logic. Alerts or maintenance logs can be transmitted to a remote data processing resource 702 or computing device 732, and GPS positioning via GPS module 514 can be used for asset tracking or geofenced regulatory compliance.

Advantages over conventional approaches can include:

Traditional systems lack the ability to dynamically switch between air treatment modes—the present invention can do so using internal catalytic components and intelligent control;

Prior air purifiers typically emit ozone without controlling residual levels—this invention includes titanium dioxide oxidation to ensure compliance with air quality limits;

Most commercial ice and water dispensers rely on filter-only approaches that do not effectively treat biofilms or interior surfaces—this system uses both gaseous and aqueous ozone to sanitize both air and water pathways;

The modular architecture allows the system to be customized for any installation: plumbed, dehumidified, or cartridge-based—with full water and air cycle control; and Other advantages.

Use Case 1: Hotel-Style or Quick-Serve Restaurant (QSR) Ice Machines

Installed in a countertop or freestanding hotel-style, QSR. Or other similar ice machines, the modular ozone-based disinfection system 100 operates in cycles. During idle hours, the system enters disinfection mode, delivering ozone-rich air 414 to sanitize interior walls and bin surfaces. It then switches to purified airflow 408 for guest-facing hours. Simultaneously, aqueous ozone 114 is flushed through the water line 240 to disinfect the inlet and ice tray before the next freeze cycle. Controller 500 ensures safe operation and automatic door locking can prevent opening during ozone cycles.

Use Case 2: Compact Refrigerators, Dorm room, Recreational Vehicle 9RV), Boat or Marine, or Breakroom Units For small, under-counter or residential-style refrigerators 230, the system can be integrated into the rear compartment or wall. The system continuously purifies the interior air using purified air 408, while periodically flushing ozone-treated water into the water line 240. A replaceable water cartridge 126 makes this configuration low-maintenance and suitable for consumer use. Integration with cloud-based alerts allows service technicians to monitor filter and cartridge life remotely.

Use Case 3: Walk-in Refrigerators or Freezers

In commercial walk-in cold storage rooms 210, the system can be wall-mounted and connected to a source water configuration 176 or a dehumidifier configuration 174. During scheduled downtime, it enters disinfection mode using ozone gas 414 or hydroxyl-enriched air 416, disinfection shelving, walls, and airflow ducts. Before reopening, the system transitions to purification mode, returning air quality to safe levels. Logs can be stored to the database 800 and accessed for health inspection compliance.

In certain embodiments, the modular ozone-based disinfection system 100 can further comprise a door-locking mechanism operatively connected to the controller 500 and configured to secure the access door of the refrigerated equipment 210. This safety feature is particularly important when the system is executing a disinfection mode that elevates the ozone concentration within the compartment using ozone-rich air 414 or hydroxyl-enriched air 416. During these cycles, the controller 500 can engage the lock at the start of the treatment to prevent accidental human access. A sensor 512 continuously monitors the internal ozone concentration, and once the level has been reduced—by operation of the titanium dioxide-coated surface 110 in the purification configuration 170, to a safe predefined threshold, the controller 500 automatically disengages the lock, allowing the door to open safely.

This behavior ensures not only occupant safety but also regulatory compliance in commercial environments such as healthcare, hospitality, and food storage, where ozone exposure limits are strictly controlled.

In another exemplary operational scenario, modular ozone-based disinfection system 100 supports interrupt-driven safety handling. If the disinfection cycle is interrupted—due to a door ajar event, door opening, emergency signal, power fluctuation, or sensor trigger—the controller 500 can immediately transition the system from disinfection mode to purification mode. In this fallback state, ozone generation is halted, and the air circulation subsystem 104 actively recirculates internal air across the titanium dioxide-coated surface 110, accelerating the reduction of ozone to safe levels. This ensures that unanticipated interruptions do not result in prolonged elevated ozone exposure or service downtime.

Figures 2, 5:
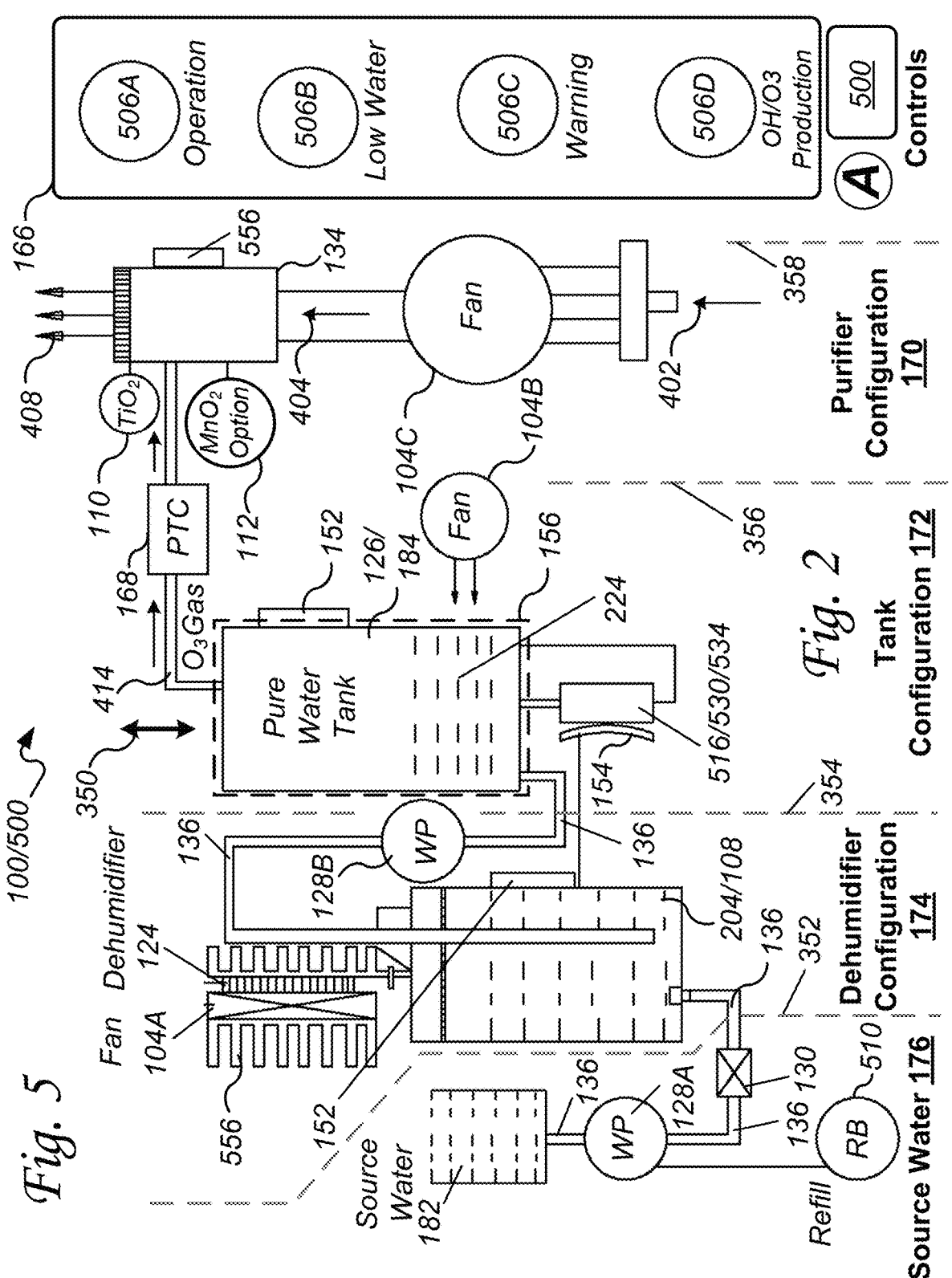
FIG. 5 illustrates one example of a modular ozone-based disinfection system block diagram.

Referring to FIG. 5, there is illustrated one example of a modular ozone-based disinfection system 100 shown in block diagram format. This system is modularly subdivided into key configurations that support flexible disinfection and purification across diverse environments. These include: a purification configuration 170, tank configuration 172, dehumidifier configuration 174, and source water configuration 176, each operatively linked to support combined or standalone functionality. Vertical dashed lines illustrate subsystem groupings, demarcated as the source water boundary 352, dehumidifier boundary 354, tank configuration boundary 356, and purification controls boundary 358.

The figure illustrates the modular, serviceable, and intelligent nature of the modular ozone-based disinfection system 100, contrasting sharply with prior ozone purifiers, which typically lack programmable modes, multi-source water integration, residual ozone mitigation, and intelligent control interfaces. This architecture supports both standalone and enterprise-wide deployment across highly regulated and safety-sensitive spaces The system includes a purification configuration 170, which begins with air inlet 402, where ambient air is drawn into the system via fan assembly 104. The air travels along an airflow path 404, where it is mixed with gaseous ozone 414 generated by the electrolytic ozone generator 516. This creates an oxidizing environment for airborne disinfection. The oxidized airflow is then passed across a titanium dioxide-coated surface 110, reducing residual ozone through photocatalytic oxidation. In some embodiments, a manganese dioxide surface 112 is positioned downstream to further convert ozone into hydroxyl radicals, producing hydroxyl-enriched air 416. The system can selectively operate in modes that deliver ozone-rich air 414, hydroxyl-enriched air 416, or purified air 408 back through air outlet 408 into the treated space.

Water required for ozone generation is supplied by the tank configuration 172, which can include either a fixed tank or a housing for a replaceable water cartridge 126, positioned within a cartridge housing 156. A water pump 128A, check valve 130, and piping 136 form the fluid connection to the electrolytic ozone generator 516, which utilizes an ion exchange material 534 to generate gaseous ozone and/or ozonated concentrate liquid 114. The fluid volume is monitored by an upper level sensor 152 and lower level sensor 154.

To increase autonomy, a dehumidifier configuration 174 may be included. This configuration comprises a condenser coil 124, a dedicated fan assembly 104, and a collection reservoir 108, into which ambient water vapor is condensed and stored. The dehumidified water can then be transferred to the tank or cartridge using interconnecting fluid lines and valves. Water extraction from the dehumidifier is regulated by a dehumidifier control module 524, which may receive commands from the system controller and respond to humidity or temperature thresholds.

The system may also include a source water configuration 176, which connects to an external continuous water supply via a fluid inlet system 182. Water from this source can be routed directly to either the collection reservoir 108 or the tank configuration 172, depending on the installation mode and demand. The source water flow is optionally pressure-regulated and may include a backflow prevention mechanism to ensure fluid isolation and safety.

All configurations are orchestrated by the controller 500, which comprises a microcontroller 502, memory 504, display 506, communication interface 508, and general-purpose input/output (GPIO) 510. The controller manages fan operations (via fan controller 528), pump and valve sequencing (pump and valve controller 520), and ozone generation profiles. It also collects input from sensor 512, which may include ozone concentration, water level, humidity, temperature 556, or system diagnostics.

An important component of the system is the dashboard or control interface, reference 'A', which can include a touchscreen, control panel, or display module mounted on the exterior of the system or connected remotely. Through this interface, a technician or user can observe real-time status indicators, which can include:

Operation;

Low Water;

Warning or Error;

OH Production Active;

Ozone Generation Active;

Purification Mode Engaged;

Disinfection Cycle Timing; or

Other Status, Indicators, or Functions.

In addition to providing feedback, a control interface, reference 'A', also enables mode selection, parameter programming, and execution of predefined disinfection profiles. This allows facility managers, technicians, or automated controllers to tailor operations to specific environments such as refrigerated compartments, HVAC ducting, or food service spaces.

Remote control and data logging can be performed through a communication interface 508, with cloud-based access supported by a remote data processing resource 702, computing device 732, or mobile dashboard. The system also includes a GPS module 514 for geolocation tracking, geofencing, and service coordination.

Figures 6, 7:
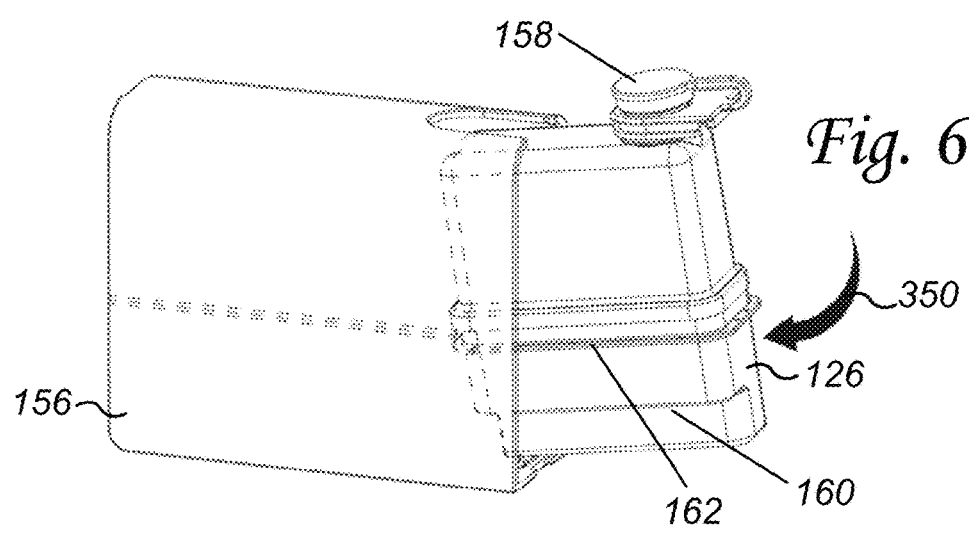
FIG. 6 illustrates one example of a replaceable water cartridge.
FIG. 7 illustrates one example of a control system for a modular ozone-based disinfection system.

Referring to FIG. 6, there is illustrated one example of a replaceable water cartridge 126 designed for use with the modular ozone-based disinfection system 100. In an exemplary embodiment, the replaceable water cartridge 126 comprises a sealable water reservoir that can be pre-filled during manufacturing or service maintenance and enclosed to prevent contamination during shipping, storage, installation, or other situations. This sealable design ensures hygienic handling and eliminates the need for users to interact with or refill the water supply, making it ideal for deployment in sensitive environments or consumer-facing installations.

In other embodiments, the cartridge 126 can be refillable. For example, a technician 302 or other trained personnel can refill the cartridge using an appropriate water source. In such configurations, the cartridge may include a removable seal cap 158 or an access port that allows for clean and secure refilling while maintaining the integrity of the system.

The type of water used in cartridge 126 can vary based on the intended application and operational parameters. In certain embodiments, the cartridge may be filled with vapor-distilled water, de-ionized water, electrolyte-enhanced formulations, or other suitable water types optimized for use with the electrolytic ozone generator 516 and the system's internal components, including the ion exchange material 534. Using purified or specialized water helps ensure consistent ozone generation efficiency, reduces mineral buildup in the system, and enhances the longevity of the electrolytic cell.

In operation, the configuration of the water cartridge 126, its interaction with the tank configuration 172, and the system-level integration with controller 500 form a comprehensive and service-friendly solution that enhances reliability, usability, and sanitation outcomes across a variety of environments.

The replaceable water cartridge 126 can be removably inserted into a corresponding housing 156, which is part of tank configuration 172 of the system. The cartridge 126 may include alignment features such as an alignment ridge 162 and contoured exterior 160, which guide the user during insertion and prevent incorrect orientation. A seal cap 158 can be provided to maintain the internal sterility of the cartridge before installation and to engage a fluid connection port upon proper seating into housing 156.

In operation, cartridge 126 supplies water to the electrolytic ozone generator 516, which uses an ion exchange material 534 to generate either gaseous ozone or ozonated concentrate liquid 114, depending on the selected treatment mode. The generated ozone can be directed into the purification configuration 170 for air disinfection, or routed into a downstream aqueous ozone circuit for water treatment applications.

In one exemplary embodiment, the system is configured to monitor the usage of the replaceable water cartridge 126 via a controller 500, which may track the number of ozone generation cycles or total operational time. Based on this data, controller 500 can determine a cartridge replacement status and disable the ozone generator if the cartridge is depleted or removed, thereby preventing damage or unsafe operation. In some embodiments, this status can be communicated to a remote computing device or data processing resource for compliance monitoring, maintenance scheduling, or alert generation.

This cartridge-based approach offers substantial improvements over prior systems that required manual refilling of reservoirs, which often led to contamination risks, water handling errors, or downtime. With the sealed and disposable nature of the cartridge 126, users and service technicians can simply swap in a new cartridge without special tools or training, enabling rapid, hygienic maintenance.

The use of the replaceable water cartridge 126 excels in at least three exemplary deployment scenarios:

Small-scale and/or portable air purifiers in hospitals, dental clinics, or other suitable locations, where frequent handling of water containers would present an infection control risk;

Hotel or guestroom ozone devices, where staff can easily replace the cartridge during routine housekeeping rounds;

Mobile or portable air and water sanitation units for disaster relief or field healthcare settings, where reliability and quick-change operation are essential; and Numerous other applications.

Referring to FIG. 7, there is illustrated one example of a control system 500 for the modular ozone-based disinfection system 100. This control system provides centralized, programmable, and remotely accessible logic for managing the disinfection system's air, water, and sensor subsystems across modular configurations. It is particularly designed for Internet of Things (IoT) deployment in safety-sensitive or compliance-driven environments such as healthcare, food handling, hospitality, and commercial refrigeration.

At the core of the control system 500 is a microcontroller 502, which governs logic processing and real-time execution of operational profiles. The microcontroller 502 is electrically connected to a memory 504, which can include volatile and non-volatile memory types for storing operational modes, sensor thresholds, diagnostic logs, and firmware.

The microcontroller 502 can be an INTEL, ZILOG, MICROCHIP, AMD, ARM, or other suitable type of microcontroller as may be required for a particular deployment.

The memory 504 can include a combination of storage types such as random access memory (RAM), read-only memory (ROM), flash memory, hard drives, solid-state drives, USB flash drives, and/or other suitable storage media.

A display 506, shown integrated with a general-purpose input/output (GPIO) interface 510, allows local interaction with the system. The display 506 can be a digital dashboard or touchscreen panel and can visually present status indicators such as Operation, Low Water, Warning, $O_3$ Production, and OH Production, as well as permit mode selection or programming.

The communication interfaces 508 enable wired and wireless connection to external systems, including remote data processing resource 702, computing device 732, and cloud-hosted dashboards. These interfaces support real-time telemetry, system alerts, remote override commands, and operational logging over Wi-Fi, Ethernet, 4G/5G, Bluetooth, and other protocols as may be required and/or desired in a particular embodiment.

The communication interface 508 can include LAN, WAN, USB, Ethernet, RS232, RS485, serial, Wi-Fi (802.11abgn or similar), 2G, 3G, 4G, 5G, Bluetooth, Zigbee, TCP, UDP, mesh networks, Pico networks, or other communication protocols as required.

The communication interface 508 is configured to enable the control system 500 to data communicate with remote data processing resources 702, computing devices 732, and other data endpoints over a global network 700 such as the Internet. This connectivity allows the system to transmit and receive operational data, support real-time control, remote monitoring, and diagnostics. For example, operational status, ozone concentration levels, runtime metrics, consumable levels (e.g., electrochemical generator 516 or ion exchange material 534), or GPS location data (from GPS 514) can be reported and monitored remotely. Through this architecture, the microcontroller 502 processes incoming sensor data (e.g., from sensors 512), applies control logic stored in memory 504, and issues commands to various subsystems such as pumps and valves 520, fan controller 528, or the dehumidifier controller 524. This control infrastructure enables real-time, intelligent automation and safe operation of the modular ozone-based disinfection system 100, including purification, aqueous ozone delivery, and disinfection cycle management across its modular configurations.

In an exemplary embodiment, the general-purpose input/output (GPIO) 510 can comprise transistor-to-transistor logic (TTL), complementary metal-oxide-semiconductor (CMOS) circuits, buffers, relays, pushbuttons, switches, and other suitable input/output devices and circuits. The GPIO 510 can be operationally related to the microcontroller 502 and configured to support multiple system control and interface features. For example, the GPIO 510 can be used for receiving manual inputs from users (e.g., button presses) and for driving system indicators (e.g., LEDs) or controlling relays tied to actuators such as valves or fans. In some embodiments, certain GPIO lines can support biometric input devices, touchscreen inputs, or keypad interfaces. The GPIO 510 can also serve as part of the user interface or control panel of the modular ozone-based disinfection system 100, providing direct physical interaction pathways for technicians 302, administrators 304, or other users. These GPIO-based controls may enable field servicing, mode switching, or test activation without the need for wireless or remote access.

One or more sensors 512 provide feedback to the control system 500. These include ozone sensors 522 (for ambient or internal air), temperature sensor 556 (for heater and environmental monitoring), and humidity sensor 518 (critical for dehumidifier configuration 174). Data from sensors 512 is processed by microcontroller 502 to inform safe operation, trigger cycle transitions, or adjust setpoints.

For location-based control, a GPS module 514 is provided. In geofenced embodiments, controller 500 can disable ozone generation if the system is moved outside a pre-authorized zone, thereby preventing unapproved or unsafe operation in regulated spaces.

The electrolytic ozone generator 516, which uses ion exchange material 534, is activated and regulated by controller 500 to produce either gaseous ozone for air treatment or ozonated liquid 114 for aqueous disinfection. Water is delivered to generator 516 from a fixed tank, replaceable cartridge 126, or source water line via pump and valve assemblies 128A and 128B, controlled by pump and valve controller 520.

The humidity sensor 518 is configured to detect ambient humidity levels within the environment or airflow chamber. It provides real-time data to the microcontroller 502, which can adjust the operational behavior of the dehumidifier configuration 174 accordingly. The humidity sensor 518 may also be used to initiate water harvesting cycles and ensure the dehumidifier operates within safe and efficient parameters.

The pump and valve controller 520 manages the activation and sequencing of water pumps 128A and 128B and any inline solenoid or check valves associated with fluid routing. It is responsible for delivering water from the tank configuration 172, dehumidifier configuration 174, or source water configuration 176 to the electrolytic ozone generator 516. The controller ensures precise flow delivery for consistent ozone output.

An ozone sensor 522 is used to track residual ozone concentration. If excessive ozone is detected during or after treatment cycles, the system may halt ozone production, redirect air through titanium dioxide-coated surface 110, or engage fan controller 528 to accelerate dilution via fan/blower assemblies 104A, 104B, or 104C.

The dehumidifier configuration 174, comprising condenser coil 124, is regulated by dehumidifier control 524. This subsystem captures water from air into a collection reservoir 108 and routes it to the tank configuration 172. Fluid flow and heater elements 168 are governed by heater control 554, ensuring consistent ozone generation conditions.

The dehumidifier control 524 is operationally related to the dehumidifier 124, the fan or blower assembly 104A, and the water tank 126 or replaceable cartridge 156. Based on signals from the humidity sensor 518 or controller logic, the dehumidifier control 524 initiates water harvesting from ambient air. It governs the condenser operation and blower cycling and ensures that collected water is directed into the reservoir or tank for use by the ozone generation subsystem.

In an exemplary embodiment, the power supply 526 provides electrical power to the core components of the modular ozone-based disinfection system 100, including the microcontroller 502, ozone generator 516, fan assemblies 104A-C, pumps 128A-B, heater element 168, and sensors 512. Power supply 526 can support multiple configurations: AC mains input (110-240V), DC input (e.g., 12V/24V), rechargeable battery packs (for portable or off-grid applications), solar panel systems (with integrated energy storage), or hybrid modes that switch between AC and battery backup. The power system may include a current sensor 532 for monitoring load, enabling the controller 500 to manage energy consumption and initiate safety or power-saving modes. In IoT-enabled configurations, communication interface 508 may report power status or alerts to a remote resource 702 or device 732, allowing real-time service and performance monitoring.

The fan controller 528 is operationally related to one or more fan/blower assemblies 104A and 104B and is configured to regulate airflow intensity and direction through the purification configuration 170. It receives input from the controller 500 and ozone sensor 522 to manage ozone dispersion, purification airflow cycles, and catalytic oxidation phases. The controller may operate the fans at variable speeds or duty cycles depending on the disinfection mode.

The aqueous ozone generator 530, optionally housed within a removable plumbed housing 178, is configured to generate ozonated concentrate liquid 114 from water received through the fluid path. It includes or is operationally related to the electrolytic ozone generator 516 and the ion exchange material 534. In some embodiments, the generator 530 may be configured to deliver aqueous ozone to internal ice machines or water dispensers for internal disinfection.

A current sensor 532 is optionally included to monitor the performance and power load of key subsystems such as fans, pumps, and heaters. Deviations in current draw can be used to preemptively detect maintenance issues or system failures.

The UV light controller 534 is operationally related to one or more ultraviolet (UV) light bulbs or sources 108A and 108B and is configured to control the timing and intensity of UV light emission. In applicable embodiments, the UV light sources are used to further degrade ozone or organic contaminants. The UV light controller 534 receives operational commands from controller 500 and may interlock with door sensors or timers to prevent unintended UV exposure.

The liquid level sensor 552 is positioned within the water tank 126 or replaceable water cartridge 156 and is configured to detect the current water volume. This sensor may include upper and lower threshold detection to monitor capacity and depletion. The controller 500 uses this feedback to prevent dry-run operation of the electrolytic ozone generator 516 and to trigger cartridge replacement notifications when necessary.

The heater control 554 is operationally related to the positive temperature coefficient (PTC) heater 168 and the temperature sensor 556. It receives commands from the controller 500 to activate or modulate the heater based on the temperature data received. The heater control 554 enables the system to condition airflow or water temperature for enhanced disinfection performance, especially when oxidation is thermally optimized.

In certain embodiments, a UV controller 528 and UV lamp may also be present to enhance disinfection, though this feature can be omitted in configurations where ozone and catalytic oxidation are the primary treatment modes.

In combination, these components form an intelligent, network-aware control framework that enables:

Automated treatment cycles;

Adaptive ozone control based on feedback;

Sensor-triggered safety shutdowns;

Geofenced enforcement;

Remote monitoring and override capabilities, and

Compliance logging for regulatory or quality assurance purposes.

This modular, IoT-integrated design allows the modular ozone-based disinfection system 100 to be deployed across multiple domains—from walk-in refrigeration units and ice machines, air purifiers, bathroom disinfection systems, food service environments, and for numerous other environments and applications—with full traceability, auditability, and serviceability.

Figure 8:
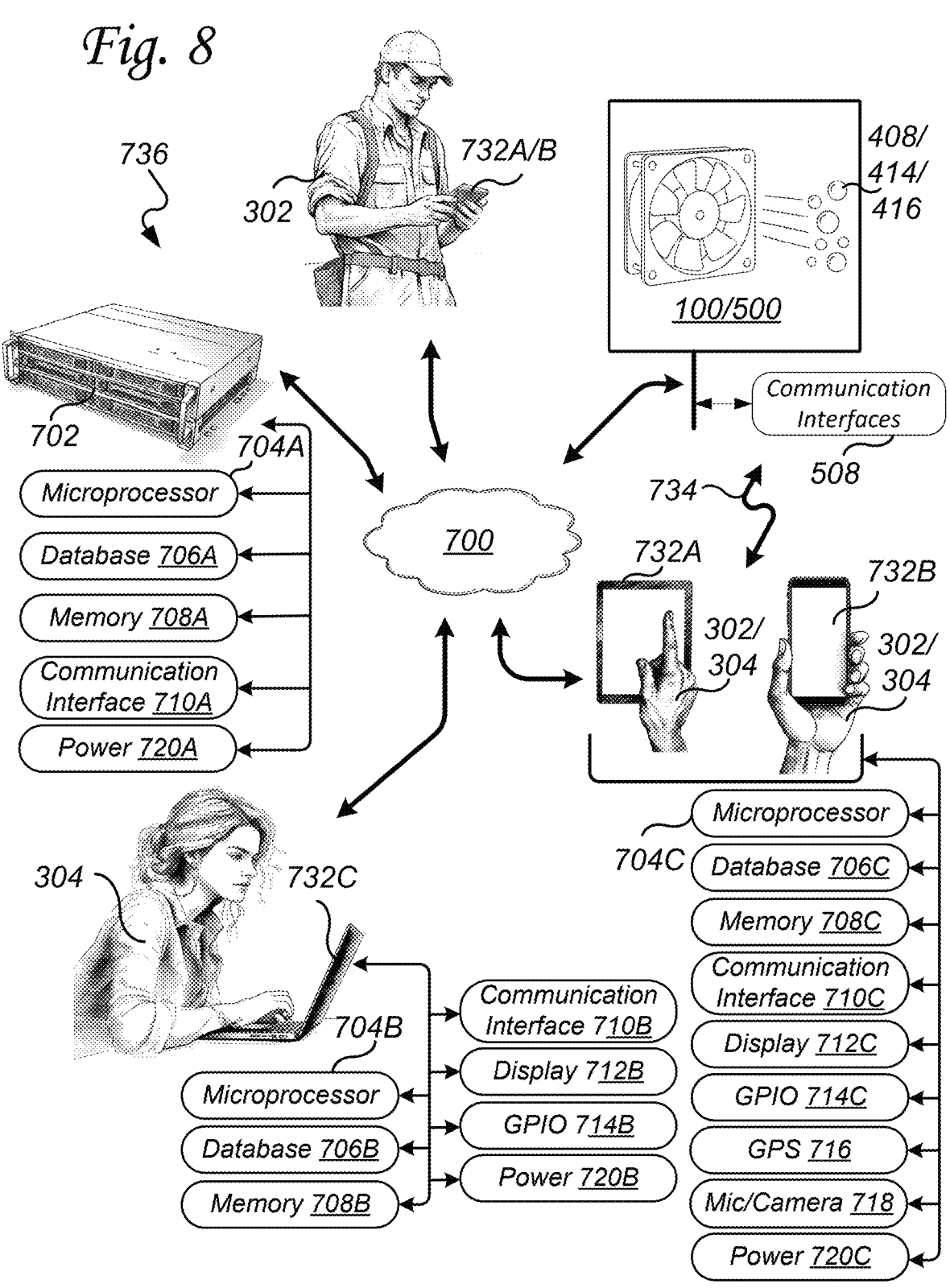
FIG. 8 illustrates one example a information technology system and network diagram.

Referring to FIG. 8, there is illustrated one example of an information technology system and network diagram associated with the modular ozone-based disinfection system 100. In an exemplary embodiment, the system is configured as an Internet-enabled (IoT) platform that allows real-time data communication between one or more deployed disinfection systems and remote computing infrastructure over a global communication network 700, such as the Internet. This networked capability enables the system to support centralized monitoring, distributed fleet management, automated alerts, service history logging, and location-based control, all accessible by both local technicians and remote administrators.

This comprehensive connectivity architecture dramatically enhances the reliability, safety, and maintainability of the modular ozone-based disinfection system 100 and positions it for deployment in highly regulated environments such as healthcare, food service, retail, transportation, and industrial settings, where consistent disinfection outcomes and auditable performance are critical.

The modular ozone-based disinfection system 100 includes a control system 500 equipped with communication interfaces 508 that enable secure data transmission to and from one or more remote data processing resources 702. These remote resources can be implemented as cloud-hosted servers, on-premise enterprise systems, or hybrid infrastructure. Each remote server 702 can include an embedded microprocessor 704A, a memory module 708A, and a communication interface 710A, all operatively connected to a database 706A that stores a disinfection/deodorization database 800. The database 800 maintains critical operational and compliance data such as account records, equipment installation locations, geofencing zones, logged ozone generator performance metrics, self-test results, technician activity logs, and system-generated notifications. These records can be used to generate maintenance schedules, track regulatory compliance, and manage hardware lifecycles for deployed systems.

Remote interaction with the system can also occur through one or more computing devices 732, which may include smartphones 732A, tablets 732B, or laptops and desktop computers 732C. Each of these computing devices is configured with a microprocessor (such as 704B or 704C), memory (708B or 708C), and database storage (706B or 706C), along with a communication interface 710B or 710C that allows network access to the control system 500 and the remote server 702. User interfaces presented on displays 712B or 712C can provide real-time visibility into system operation, maintenance status, and alerts, while GPIO 714B or 714C can support connected peripherals or inputs in technician-facing software. Some devices may also include onboard GPS modules 716, microphones, or cameras 718 for location tagging or remote support diagnostics.

Power for these computing devices may be provided by integrated rechargeable batteries or AC adapters 720B and 720C, depending on device type and intended field use. Field technicians 302 and administrators 304 can use these mobile or desktop interfaces to view installed system records, access troubleshooting logs, initiate diagnostic tests, or issue remote commands such as starting or stopping disinfection cycles, overriding alerts, or updating firmware.

In one exemplary use case, a technician 302 accesses a secure dashboard using a tablet 732B. Through the interface, they can view a visual representation of an installation site, such as a floorplan 844 that shows the location of multiple deployed systems 100. The interface allows the selection of discrete zones labeled as 'A' 846A, 'B' 846B, 'C' 846C, and 'D' 846D, each corresponding to a specific location in a facility such as a restroom, food service area, patient room, or refrigerated equipment zone. Once selected, the interface presents detailed system information, including current system location 838, operational status 840 (e.g., active disinfection or standby), and cartridge or consumable status 842 (e.g., percent of water remaining, ozone cell health, or replacement prompts).

Through this integrated information technology system, the modular ozone-based disinfection system 100 is able to deliver proactive alerts, verify location-based compliance (e.g., geofenced operation using GPS 514), and offer both local and remote access to critical performance metrics. The Internet-connected architecture allows administrators to manage large fleets of systems across multiple sites while enabling technicians in the field to efficiently diagnose, service, or validate proper operation of each unit. Furthermore, firmware updates, new treatment modes, or response profiles can be pushed to the systems from the cloud without requiring manual intervention at the hardware level.

Referring to FIG. 9, there is illustrated one example of a disinfection/deodorization database structure 800 for use in a modular ozone-based disinfection system 100. The database structure 800 is designed to organize, track, and manage various operational, location, and service-related data records for system 100 across its installed base. In an exemplary embodiment, database 800 can be hosted on a remote data processing resource 702, or accessed by computing devices 732A-C operated by a technician 302 or admin user 304. The database 800 can be implemented using various database technologies including SQL, MYSQL, MARIADB, ORACLE, MS ACCESS, flat file structures, network-attached storage, or other suitable formats.

Within database 800, the account records 802 store user credentials, service level information, and customer billing or licensing data. Location records 804 link each deployed system 100 to a geographic or facility location, which can also be integrated with geofence records 806 that establish virtual perimeters for monitoring compliance with disinfection schedules or verifying proximity access control. Equipment records 808 contain metadata about each individual system 100, including serial number, model configuration (e.g., purification configuration 170, tank configuration 172, etc.), operational history, and hardware lifecycle status.

Self-test results 810 are automatically logged by the system controller 500 and include health check data such as ozone sensor readings, liquid level thresholds, error flags, or status of replaceable components like the water cartridge 126 and electrochemical ozone generator 516. These are tagged with timestamps and cross-referenced to the associated equipment record 808.

Technician records 812 track interactions by service personnel 302, including maintenance visits, part replacements, software updates, and remote diagnostics performed via computing devices 732. Notification records 814 capture automated alerts sent to technicians or administrators, such as warnings for low water level, abnormal ozone production, expired cartridge alerts, or maintenance reminders. These records can also include ozone readings, cartridge status, and customizable notification messages.

Importantly, ozonator records 816 house detailed profiles of the ozone-generating components themselves. These include installation date, generator life estimates, past performance trends, and humidity-related performance adjustments that affect efficiency. Records may also include fault logs and anticipated replacement timelines based on usage analytics.

The modular nature of the system architecture allows the database 800 to dynamically accommodate various embodiments, including those incorporating dehumidifier configuration 174, source water configuration 176, or IoT-enabled sensor packages. The integration of this structured data enables scalable service logistics, operational transparency, and optimized lifecycle management of each modular ozone-based disinfection system 100 deployed across public and private environments.

Figure 10:
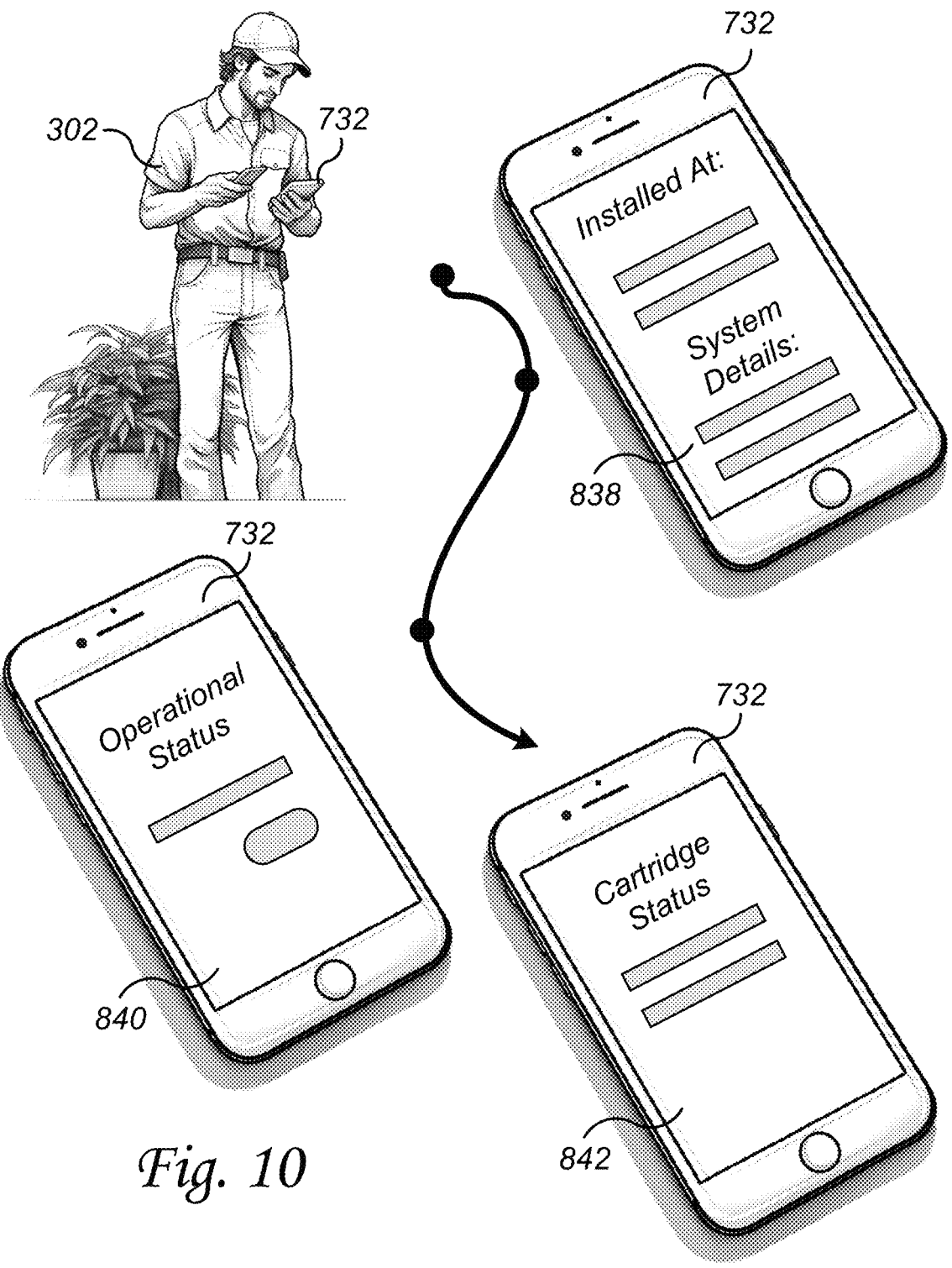
FIG. 10 illustrates one example of a technician's use of a software application.

Referring to FIG. 10, there is illustrated one example of a technician's use of a software application for monitoring and servicing the modular ozone-based disinfection system 100. In an exemplary embodiment, technician 302 uses a computing device 732, which can be a smartphone 732A, tablet 732B, or laptop/desktop 732C, to interact with a user interface of a service or maintenance application configured to manage various features of the system 100. The computing device 732 data communicates with a remote data processing resource 702 over a global network 700, retrieving system-level diagnostics and operational insights, as well as synchronizing service records and usage data in real-time.

A first screenshot 838 illustrates display of the installed location and technical details associated with a specific modular ozone-based disinfection system 100. This can include model number, serial number, system configuration (e.g., purification configuration 170, tank configuration 172, and control system 500), installation date, and current firmware version.

A second screenshot 840 illustrates an operational status display, including system mode (e.g., purification, disinfection, idle), ozone generation activity, OH generation status, aqueous ozone flow, and other sensor readings such as temperature, humidity, or ozone concentration. This interface allows technician 302 to confirm the system 100 is operating within configured parameters and optionally initiate test cycles or diagnostics.

A third screenshot 842 illustrates cartridge status information for the replaceable water cartridge 156 and the electrolytic ozone generator 516. In one embodiment, the service app can show remaining estimated service life, usage history, last replacement date, and alert indicators for replacement or refill. Such operational status helps ensure proactive maintenance and reduces the risk of system downtime.

FIG. 10 also illustrates a floor plan 844 of a geofenced facility or environment, such as a hospital, office building, or restaurant. Within the floor plan 844, multiple monitored zones are represented, including zone 'A' 846A, zone 'B' 846B, zone 'C' 846C, and zone 'D' 846D. Each of these zones is associated with an installed modular ozone-based disinfection system 208. Technician 302, by viewing the map interface, can assess the placement and status of each unit, track their health over time, and validate coverage for disinfection compliance.

This figure highlights the service-layer visibility provided by the Internet of Things (IoT) capabilities embedded in the system 100. Through the computing device 732, technician 302 can manage both localized and distributed installations across multiple geofenced locations, enabling faster diagnostics, easier system configuration, firmware updates, and real-time verification of operational integrity. This modern cloud-connected service platform is a significant advancement over traditional air purification systems, which lacked remote serviceability, integration with digital service logs, or automated cartridge management.

Figure 11:
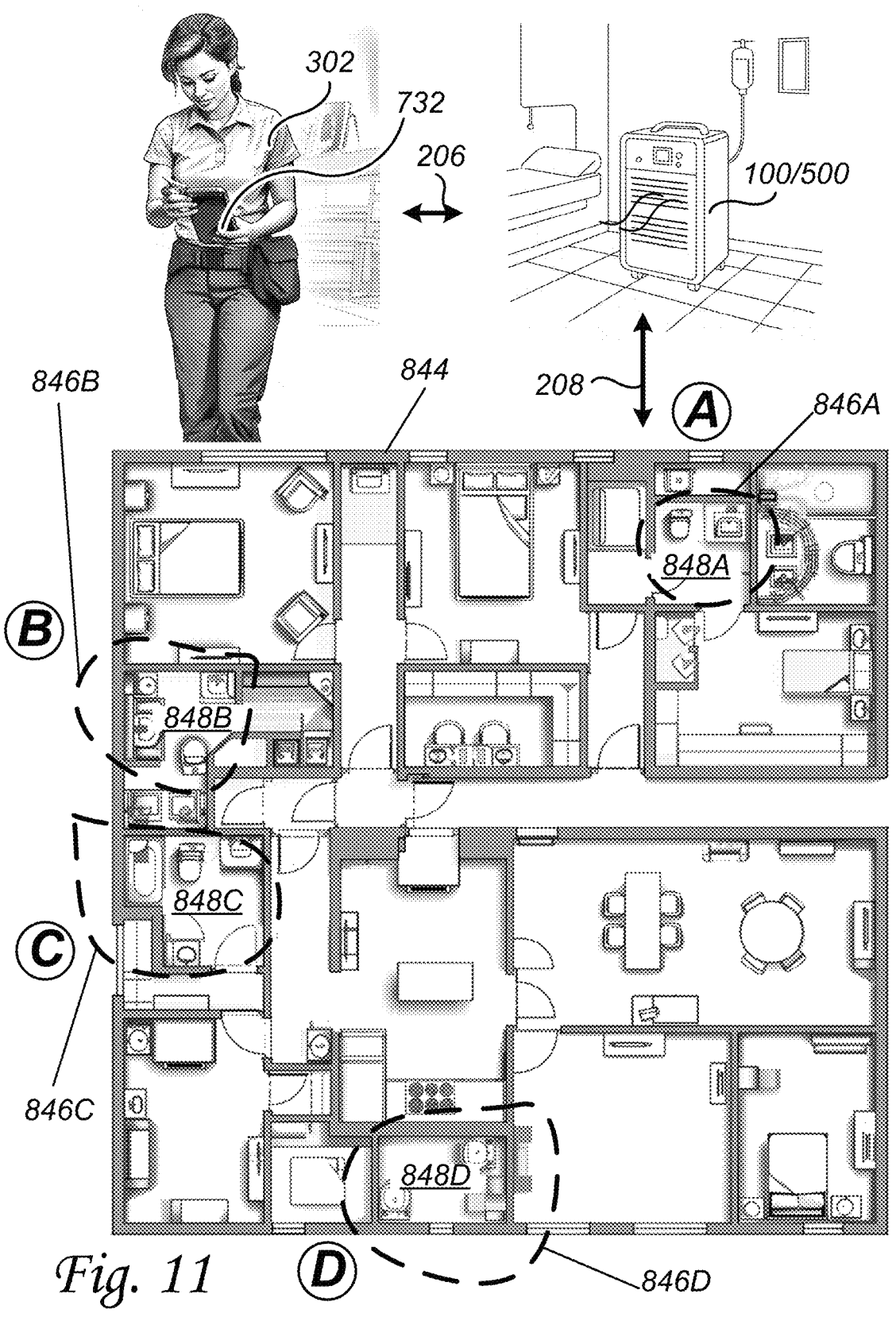
FIG. 11 illustrates one example of a floor plan to monitor geofenced or geolocate room spaces that have installed a modular ozone-based disinfection system.

Referring to FIG. 11, there is illustrated one example of a floor plan 844 configured to enable monitoring of geofenced or geolocated room spaces in which a modular ozone-based disinfection system 100/500 has been installed. In an exemplary embodiment, each room or designated area is assigned a monitored zone 846A-D, which may correspond to spaces such as operating rooms, laboratories, cleanrooms, or other controlled environments.

A room identifier 848A-D can be associated with each monitored zone to facilitate tracking and system association, and an installed system identifier 850 can indicate the specific modular ozone-based disinfection system 100/500 deployed in that room or zone. The identifiers 848A-D can be managed via a backend remote data processing resource 702, which synchronizes with a local computing device 732 operated by a technician 302. In some embodiments, these identifiers and associated metadata are visualized through a software application or dashboard running on the computing device 732, providing real-time insights on device location, operational status, and geofenced boundaries.

The modular ozone-based disinfection system 100/500 installed in each geofenced room space can be configured to operate according to room-specific disinfection schedules or sensor-triggered activation. Integration with GPS 514 or other location-aware technologies enables geofencing logic that supports location-based analytics, automated alerts, and compliance tracking. For example, the system can log when a technician enters a geofenced area, prompt a pre-disinfection verification, and begin cycle initiation. Upon completion, the system can log and transmit cycle metadata such as duration, ozone levels, and surface coverage reports to the database 706A.

Technician 302 can utilize the geolocation map of floor plan 844 to monitor multiple disinfection zones, confirm successful treatment, and respond to exceptions (e.g., missed cycles, system faults). This approach enhances operational visibility and centralizes the management of distributed ozone-based disinfection equipment across a facility or campus. The ability to correlate monitored zone 846, installed modular ozone-based disinfection system 100, and location IDs 848A-D streamlines reporting and audit trails for regulatory and internal review purposes.

Referring to FIG. 12, there is illustrated one example of a method of using a modular ozone-based disinfection system for treating air with ozone. This method highlights a self-contained ozone generation and purification process that utilizes a replaceable water cartridge to generate ozone gas for disinfection and a titanium dioxide-coated surface for safe purification. The method is designed to enable reliable surface and air treatment cycles in enclosed environments while maintaining compliance with human exposure safety limits.

The method begins in step 1002 by inserting a replaceable water cartridge 126 into a tank configuration 172 that is operatively connected to a purification configuration 170. In one embodiment, the replaceable cartridge 126 can be pre-filled and sealed during manufacturing, while in other embodiments, a technician 302 can manually refill the water cartridge using deionized, vapor-distilled, or electrolyte-enhanced water. The cartridge housing 156 ensures compatibility and prevents improper insertion via alignment features such as a contoured exterior 160 and alignment ridge 162.

In step 1004, an electrolytic ozone generator 516—fluidly connected to the tank configuration 172—is activated to generate gaseous ozone from the water. The electrolytic ozone generator 516 utilizes ion exchange material 534 to separate oxygen and hydrogen molecules during electrolysis, forming high-purity ozone suitable for controlled disinfection applications.

In step 1006, the generated ozone is directed into the purification configuration 170, where it is actively mixed with circulating airflow. The resulting mixture forms an oxidizing environment within the housing of the purification configuration, enabling rapid neutralization of airborne contaminants, microbial particles, and other impurities.

In step 1008, the oxidizing airflow is exposed to a titanium dioxide-coated surface 110 positioned within the purification configuration 170. This titanium dioxide-coated surface facilitates a photocatalytic reaction which chemically neutralizes residual ozone and other oxidants in the airflow. This reaction helps reduce ozone concentration while preserving disinfection efficacy. The step is particularly advantageous as it addresses one of the shortcomings of prior approaches that lacked internal ozone scrubbing, often leading to safety concerns related to prolonged ozone retention in treated environments.

In step 1010, the treated airflow is discharged from the modular ozone-based disinfection system 100 once the ozone concentration has been sufficiently reduced. The purification system is configured such that the concentration of ozone in the discharged air is below permissible exposure limits for human occupancy, thereby ensuring safe reintegration into occupied spaces.

Referring to FIG. 13, there is illustrated one example of a method of using a modular ozone-based disinfection system for treating air with ozone. This method is particularly advantageous for applications where an integrated dehumidifier configuration 174 is used to autonomously extract water from ambient air, enabling the system to operate independently from external water supplies. The method enables the generation and controlled use of ozone for air disinfection, while ensuring that residual ozone levels are reduced before being reintroduced into the environment. The method begins in step 1102 by extracting water from ambient air using the dehumidifier configuration 174.

In step 1102, the dehumidifier configuration 174, which can include a fan/blower 104A, condenser coil 124, and collection reservoir 108, operates to draw in ambient air, condense moisture from that air, and collect the water for internal use. This step enables the system to generate ozone without relying on an external or manually filled water source.

In step 1104, the extracted water is delivered from the collection reservoir 108 into the tank configuration 172. This water transfer can occur via gravity, pump, or other suitable delivery methods. The tank configuration 172 can comprise either a fixed internal tank or a housing configured to receive a replaceable water cartridge 126, depending on the embodiment.

In step 1106, gaseous ozone is generated from the water using an electrolytic ozone generator 516, which is fluidly connected to the tank configuration 172. The ozone generator 516 uses ion exchange material 534 to electrolyze the water into ozone gas. This process may also produce a small amount of hydrogen and oxygen as byproducts.

In step 1108, the ozone gas is directed into a purification configuration 170, where it is mixed with airflow drawn in from the surrounding environment. The mixing process forms an oxidizing environment that treats and disinfects the air. The air circulation subsystem, which includes fans 104, ensures continuous movement of air across the internal components.

In step 1110, the ozone-treated air is passed across a titanium dioxide-coated surface 110 positioned within the purification configuration 170. The titanium dioxide-coated surface 110 promotes a photocatalytic reaction that chemically reduces residual ozone and oxidants remaining in the airflow. This step enhances safety and prepares the airflow for recirculation.

In step 1112, the treated airflow is discharged back into the surrounding environment. Because the photocatalytic reaction has lowered the ozone concentration to a level compliant with applicable human exposure safety limits (e.g., OSHA PEL of 0.1 ppm over 8 hours), the discharged air is suitable for reintroduction into occupied spaces.

Referring to FIG. 14, there is illustrated one example of a method of performing disinfection using a modular ozone-based disinfection system that incorporates a source water configuration to enable continuous ozone generation and disinfection operation. This embodiment is particularly advantageous in applications requiring sustained performance without frequent manual water replenishment, such as food service refrigeration, laboratory cold storage, or healthcare-related cleanroom refrigeration environments. The method integrates continuous water supply with automated ozone generation and purification functionality. The method begins in step 1202 by connecting the source water configuration 176 to an external water supply.

In step 1204, water from the source water configuration 176 is supplied to the tank configuration 172. In one embodiment, the water may pass through a collection reservoir 108 that acts as a buffer or intermediary volume. In other embodiments, the tank 126 of the tank configuration 172 receives the water directly. This setup provides operational flexibility based on the plumbing architecture of the installation site.

In step 1206, the electrolytic ozone generator 516 uses the received water—optionally enhanced or filtered—to generate gaseous ozone. The electrolytic ozone generator 516 can include or be operationally associated with an ion exchange material 534, which enhances ozone output by stabilizing water chemistry and promoting optimal electrochemical reactions. The generated ozone is directed toward the purification configuration 170.

In step 1208, the generated ozone is introduced into the airflow within the purification configuration 170, forming a highly oxidative environment. This oxidizing atmosphere is ideal for neutralizing airborne contaminants such as bacteria, viruses, and odor-causing compounds, especially in environments where maintaining hygienic air conditions is critical.

In step 1210, the ozone-treated airflow is exposed to an ozone-neutralizing surface, such as a titanium dioxide-coated structure positioned in the airflow path. This exposure promotes photocatalytic oxidation or a catalytic breakdown of residual ozone, reducing ozone concentration to levels that are compliant with applicable human exposure safety limits.

In step 1212, the now-treated and neutralized airflow is discharged from the modular ozone-based disinfection system 100. At this stage, the airflow is no longer at elevated oxidant levels and is safe for reintroduction into spaces that may become occupied. This ensures user safety while maintaining effective disinfection during idle or unoccupied cycles.

This method exemplifies a robust, autonomous disinfection approach that is ideal for continuous-use environments, offering reduced maintenance burden and increased operational uptime without compromising safety.

Referring to FIG. 15, there is illustrated exemplary embodiments of a method of performing disinfection using a modular ozone-based disinfection system 100 that can be interchangeable with the methods of the present invention. This method emphasizes a modular and scalable implementation, with features that support compact installation, automated cycle control, and environmental sensing. The steps described are designed to be used across different system configurations including those that incorporate a fixed tank, replaceable cartridge, dehumidifier, and continuous water source.

In step 1302, the operation of the purification configuration can be initiated using a controller 500 configured to regulate fan speed and ozone generation.

In operation the controller 500 powers on the purification configuration 170 and initializes the air circulation subsystem. This includes activating one or more fans 104 to begin drawing air through the system. Simultaneously, the controller may perform a startup diagnostic, verify component readiness, and precondition ozone generation parameters based on current environmental inputs or stored profiles. Regulation of fan speed allows the system to tailor treatment intensity and cycle duration to the specific needs of the space being disinfected.

In step 1304, the purification configuration 170 and tank configuration 172 are mounted within a shared enclosure arranged in a vertically stacked orientation. This vertical arrangement allows water to move from the tank (such as a fixed reservoir or cartridge 126) down to the electrolytic ozone generator 516 by gravity, reducing the need for pressurized pumping mechanisms. The compact layout also simplifies modular servicing, enabling easy access to both fluid and air components without disassembling the entire housing, and supports portability or wall-mounted installation in space-constrained environments.

In step 1306, an ozone sensor 522 monitors the ozone concentration in the treated airflow before it is discharged from the system. This step ensures that the residual ozone level falls below regulatory exposure limits (such as OSHA PEL or ACGIH TLV) before the treated air is released back into an occupied environment. The sensor's data can trigger adjustments in fan operation, ozone generator duty cycle, or the activation of internal ozone-neutralizing features, such as a titanium dioxide-coated surface 110 or manganese dioxide surface 112.

In step 1308, the system executes a user-selected disinfection profile stored in memory 504 of the controller 500. These profiles may be preprogrammed or customized, and can define operational parameters such as cycle length, ozone output rate, purification duration, and sensor feedback thresholds. Technicians 302 or administrators 304 may access and select these profiles via local interface (e.g., display 506 or GPIO 510) or remotely using a connected computing device 732.

In step 1310, the system operates a condenser coil 124 to collect moisture from the surrounding air using the dehumidifier configuration 174. A fan 104A draws ambient air across the coil, where it condenses and drips into the collection reservoir 108. This water is then directed into the tank configuration 172 for use by the electrolytic ozone generator 516. This step is especially beneficial for autonomous systems or those deployed in environments where plumbing access is limited.

In step 1312, the controller 500 switches between ozone generation and purification modes. In ozone generation mode, water is electrolyzed to produce gaseous ozone that mixes with circulating air to perform disinfection. In purification mode, the airflow is directed across catalytic surfaces such as titanium dioxide 110 to reduce residual ozone. The controller may transition between these modes based on elapsed time, ozone concentration, or completion of a predefined treatment cycle.

In step 1314, the treated air is discharged through an air outlet positioned in the purification configuration 170. The outlet is configured to emit air that has passed through the system's oxidation and purification stages and meets human exposure safety standards. The direction, pattern, and velocity of discharge can be controlled to maximize room coverage while maintaining low noise and energy consumption.

In step 1316, a fill-level sensor 552 monitors the water level in the tank configuration 172. If the water level falls below a critical threshold, the system may pause ozone generation and notify a user or technician. In some configurations, the sensor may also manage water input from a source water configuration 176 or initiate a refill from the dehumidifier collection reservoir 108.

Referring to FIG. 16, there is illustrated one example of a method of purifying air in a refrigerated space using an ozone-based disinfection system. In an exemplary embodiment, the method is designed to maintain high air quality inside refrigerated environments such as ice makers, walk-in refrigerators, and consumer-grade refrigeration units. A key advantage of the present invention is the internal reduction of ozone concentration using photocatalytic surfaces, enabling disinfection without emitting harmful ozone levels into food storage environments. This makes the method particularly beneficial in applications where air disinfection must occur without affecting food safety or human access. The method begins in step 1402 by operating a controller to initiate a purification mode by activating an electrolytic ozone generator and an air circulation subsystem.

In step 1404, gaseous ozone is generated from water using the electrolytic ozone generator. The generator can include an ion exchange material to improve the purity and efficiency of ozone generation, ensuring consistent oxidizing power for disinfection purposes.

In step 1406, the gaseous ozone is mixed with airflow originating from the refrigerated space within a housing. This forms an oxidizing environment within the housing where microbial, bacterial, and viral contaminants present in the airflow can be neutralized by the oxidizing properties of ozone.

In step 1408, the oxidizing airflow is directed across a titanium dioxide-coated surface. The titanium dioxide coating promotes a photocatalytic reaction that facilitates the breakdown of residual ozone and volatile compounds. This step serves two purposes: (1) to further disinfect the airflow and (2) to reduce ozone concentration to a human-safe level prior to venting.

In step 1410, the treated airflow is returned into the refrigerated space. By this stage, the ozone concentration in the airflow has been reduced to a level compliant with applicable human exposure safety limits, such as those defined by OSHA or international food safety guidelines. This step ensures that the disinfection process can be performed safely without exposing stored goods or users to elevated ozone levels.

Referring to FIG. 17, there is illustrated one example of a method of purifying air in a refrigerated space using an ozone-based disinfection system that operates in a staged treatment cycle. Unlike continuous purification methods, this embodiment includes a distinct disinfection mode followed by a purification mode, allowing the system to temporarily elevate ozone concentration within the refrigerated space to perform surface-level disinfection and then safely restore air quality for reentry or food storage. This two-mode approach provides enhanced microbial reduction while maintaining compliance with human exposure safety limits. The method begins in step 1502 by operating the ozone-based disinfection system in a disinfection mode by activating an electrolytic ozone generator to generate a gaseous ozone from water.

In step 1504, the generated gaseous ozone is directed into the refrigerated space for a fixed disinfection period. During this time, the ambient ozone concentration is raised above normal operational thresholds to provide deep oxidation of interior surfaces, shelving, bins, and other components exposed to the air. The disinfection period is carefully timed or sensor-controlled to ensure efficacy without prolonged overexposure.

In step 1506, the system transitions into a purification mode using a controller 500. The controller may be preprogrammed with disinfection profiles or rely on sensor inputs such as ozone concentration data to automatically determine when to switch modes. The transition marks the end of the elevated ozone exposure period and the beginning of the internal air neutralization process.

In step 1508, air from the refrigerated space is recirculated through a purification configuration that includes a titanium dioxide-coated surface positioned in the airflow path. As the air passes across the surface, the titanium dioxide facilitates photocatalytic oxidation, chemically degrading residual ozone and neutralizing volatile organic compounds and other oxidants that may have accumulated during the disinfection phase.

In step 1510, the ozone concentration in the recirculated airflow is reduced to a level compliant with applicable human exposure safety limits. Once treated, the airflow is discharged back into the refrigerated space. The system ensures that the returned air is safe for human access and food storage, thus supporting cyclic disinfection schedules without compromising safety or regulatory compliance.

Referring to FIG. 18, there is illustrated one example of a method of purifying air in a refrigerated space using an ozone-based disinfection system that leverages a manganese dioxide treatment module to generate hydroxyl radicals for enhanced oxidizing performance. This method is distinct from prior examples in that it shifts the disinfection chemistry from direct ozone exposure to the use of secondary oxidants (OH radicals), which offer potent microbial neutralization while reducing ozone-related regulatory complexity. Additionally, the method enables simultaneous treatment of both air and water within the same refrigerated environment, making it particularly well suited for enclosed food storage systems, combination ice maker-dispenser units, and similar applications. The method begins in step 1602 by generating gaseous ozone from water using an electrolytic ozone generator positioned within a housing.

In step 1602, the system activates the electrolytic ozone generator 516 to produce ozone gas by electrolyzing water received from a tank configuration 172 or source water configuration 176. The generator may include or operate in conjunction with ion exchange material 534 to ensure the water chemistry supports high-purity ozone generation. The generator is enclosed within the modular housing of the system to support compact integration into refrigerated appliances.

In step 1604, the generated gaseous ozone is directed over a manganese dioxide treatment module 112 also positioned within the housing. As ozone molecules pass through the manganese dioxide surface, they undergo a catalytic reaction that produces hydroxyl radicals ($\cdot$OH). These radicals are highly reactive oxidants capable of breaking down microbial cell walls, odors, and biofilm-forming agents with short dwell times and without leaving harmful residue.

In step 1606, the hydroxyl-enriched air is circulated into the confined refrigerated space. A fan or blower within the air circulation subsystem 104 distributes this reactive air throughout the enclosure, enabling uniform treatment of both the internal air volume and exposed surfaces. Because hydroxyl radicals have extremely short lifespans, they react quickly within the space and are unlikely to persist or accumulate, making this approach highly effective while remaining safe for enclosed or intermittently occupied environments.

In step 1608, aqueous ozone generated by the same electrolytic ozone generator is routed into a water pathway used by an ice maker or water dispenser associated with the refrigerated space. This pathway may include an ice tray, reservoir, dispensing tube, or valve manifold 418. Aqueous ozone acts as a secondary disinfectant within the water system, helping to reduce bacterial buildup, scale formation, and taste/odor issues within components that store or deliver water or ice to users.

Referring to FIG. 19A, there is illustrated one example of a method of purifying air in a refrigerated space using a modular ozone-based disinfection system 100. This particular method emphasizes intelligent, adaptive disinfection behavior within ice machines and refrigerator compartments, incorporating automated and sensor-driven control features to manage ozone-based air and water treatment. The method supports enhanced safety, waterline disinfection, and user-programmable disinfection routines that respond dynamically to sensed ozone levels and operational conditions.

In step 1702, aqueous ozone generated by the electrolytic ozone generator 516 is directed into a water line using the aqueous ozone circuit 418. This water line may supply either an ice maker 232 or a refrigerator water dispenser. The introduction of ozonated water 114 into these pathways provides disinfection benefits, reducing microbial buildup within the water system and improving hygiene for the ice cubes 420 and dispensed water.

In step 1704, the modular ozone-based disinfection system 100 maintains continuous purification during the normal operation of the refrigerated appliance 210. The system 100 operates in a low-ozone, continuously circulating air purification mode that ensures ongoing air quality improvement while maintaining ozone levels within regulatory safety thresholds for occupied environments.

In step 1706, the treated and purified air is directed into an interior bin or compartment of an ice machine 232. This airflow 408, having passed through titanium dioxide photocatalytic oxidation and ozone neutralization stages, helps maintain the cleanliness of internal ice-making surfaces by inhibiting microbial accumulation and biofilm formation.

In step 1708, a sensor 512, such as an ozone sensor 522, detects the concentration of ozone within the refrigerated space. This real-time ozone level monitoring allows the system 100 to ensure air safety, manage transitions between disinfection and purification modes, and prevent exposure to elevated ozone concentrations.

In step 1710, in response to detecting an ozone concentration that exceeds a predefined threshold, the operation of the electrolytic ozone generator 516 is reduced or paused. This dynamic control minimizes risk and facilitates compliance with occupational and food safety ozone exposure limits.

In step 1712, the controller 500 logs operational data associated with ozone generation or purification. This data may include timestamps, ozone levels, disinfection cycle duration, or system mode changes. The logged data supports compliance tracking, maintenance auditing, and system performance evaluation over time.

In step 1714, aqueous ozone is generated concurrently with gaseous ozone using the electrolytic ozone generator 516 and directed into the same or different water lines of the ice maker or dispenser. This concurrent generation enables simultaneous disinfection of air and water pathways using a shared electrochemical ozone generation platform.

In step 1716, the controller 500 automatically transitions the system from disinfection mode to purification mode based on a stored timer. This ensures that after a defined disinfection duration, the system shifts to ozone reduction and air polishing using a titanium dioxide-coated surface to restore ozone levels to human-safe thresholds.

In step 1718, the user is enabled to select a stored cleaning or disinfection profile via a control panel or other user interface (e.g., dashboard, touchscreen, or app-based interface). These profiles may define operational parameters such as duration, airflow intensity, water disinfection timing, and ozone generation strength, offering flexible customization to meet the needs of various refrigerated environments and compliance protocols.

Referring to FIG. 19B, there is illustrated exemplary embodiments of a method of purifying air in a refrigerated space using a modular ozone-based disinfection system 100 that can be interchangeable with the methods of the present invention. These embodiments demonstrate enhanced operational safety, precision disinfection control, and versatility in how airflow and water disinfection are managed during ozone-based treatment cycles.

The method begins in step 1720 by directing recirculated air across a titanium dioxide-coated surface 410 within the housing during the purification mode. This surface is configured to promote photocatalytic oxidation, thereby reducing residual ozone in the airflow to a level compliant with applicable human exposure safety limits.

In step 1722, the system emits a visual or audible signal to indicate that the disinfection mode is actively running. This feature ensures users are aware that a high-ozone disinfection cycle is in progress and entry into the refrigerated space should be avoided.

In step 1724, the system records disinfection cycle parameters such as start time, ozone concentration profiles, and duration, which are stored locally or remotely for traceability, compliance monitoring, or quality assurance purposes.

In step 1726, a door locking mechanism is automatically activated to secure the refrigerated space during the disinfection cycle, thereby preventing accidental human exposure to ozone levels above safety thresholds.

In step 1728, the system automatically unlocks the door of the refrigerated space only after sensors confirm that the gaseous ozone concentration has been reduced to a safe level for human reentry, as determined by preset or regulatory exposure thresholds.

In step 1730, the aqueous ozone 114 generated during the cycle is directed to a water line, ice tray, or water reservoir associated with the ice maker 232 or refrigerator water dispenser. This allows for effective water-based disinfection of components that contact consumables like ice or water.

In step 1732, the housing is mounted to an interior wall of the refrigerator or ice machine enclosure. This embedded installation enables efficient internal recirculation of ozone-treated or purified air and facilitates integrated disinfection without occupying valuable exterior space.

These method steps collectively contribute to the safe, automated, and comprehensive disinfection of both air and water pathways in refrigerated equipment 210, especially in applications such as hospital cold storage, commercial walk-ins, and ice makers in food service environments.

Referring to FIG. 20, there is illustrated one example of a method of performing disinfection using a modular ozone-based disinfection system 100 having a replaceable water cartridge 126. This method provides a compact, low-maintenance solution for ozone-based air purification, particularly in environments where water supply infrastructure is limited. The use of a pre-filled, sealed water reservoir in the replaceable water cartridge 126 enables plug-and-play operation, and the electrochemical generation of ozone allows for precise, on-demand disinfection cycles. The integration of ultraviolet (UV) light and a titanium dioxide (TiO$_2$)-coated surface 110 promotes photocatalytic oxidation, ensuring that any residual ozone in the treated airflow 408 is neutralized before being vented to the surrounding environment. The method begins in step 1802 by inserting a replaceable water cartridge 126 comprising a sealed water reservoir into a housing of the modular ozone-based disinfection system 100.

In step 1804, water from the inserted replaceable water cartridge 126 is supplied to an electrochemical ozone generator 516, which in an exemplary embodiment utilizes ion exchange material 534 to support the generation of high-purity ozone gas from the input water. The fluidic pathway between the cartridge 126 and the ozone generator 516 is established via internal tubing 136 and a fluid connection port configured for alignment during cartridge insertion.

In step 1806, the electrochemical ozone generator 516 produces gaseous ozone from the supplied water. The system is capable of generating controlled concentrations of ozone suitable for use in confined indoor environments. The ozone gas output is then directed into the airflow within the housing.

In step 1808, an internal air circulation subsystem, which can include one or more fans 104A/B, is used to direct airflow through the housing, mixing the airflow with the generated ozone gas to create an oxidizing atmosphere. This ozone-air mixture is distributed across internal treatment surfaces to provide microbial and odor reduction.

In step 1810, the oxidizing atmosphere is exposed to a titanium dioxide-coated surface 110. The surface is irradiated with ultraviolet (UV) light sources 108A and/or 108B, promoting a photocatalytic oxidation reaction that chemically reduces residual ozone to oxygen, while also breaking down volatile organic compounds and microbial contaminants present in the airflow.

In step 1812, the now-treated and chemically neutralized airflow is vented from the housing through an outlet pathway. This ensures that the ozone concentration in the discharged air is reduced to a level compliant with applicable human exposure safety limits, allowing for safe use of the system in occupied spaces.

In step 1814, a controller 500, which includes a microcontroller 502, memory 504, display 506, and communication interfaces 508, operates the electrochemical ozone generator 516 and the air circulation subsystem. The controller manages system functions according to one or more stored operational modes, which can include user-selected settings, time-based disinfection cycles, or remote-initiated commands via IoT connectivity. The controller can also log system operation data and trigger maintenance alerts if cartridge depletion or other conditions are detected.

Figure 21:
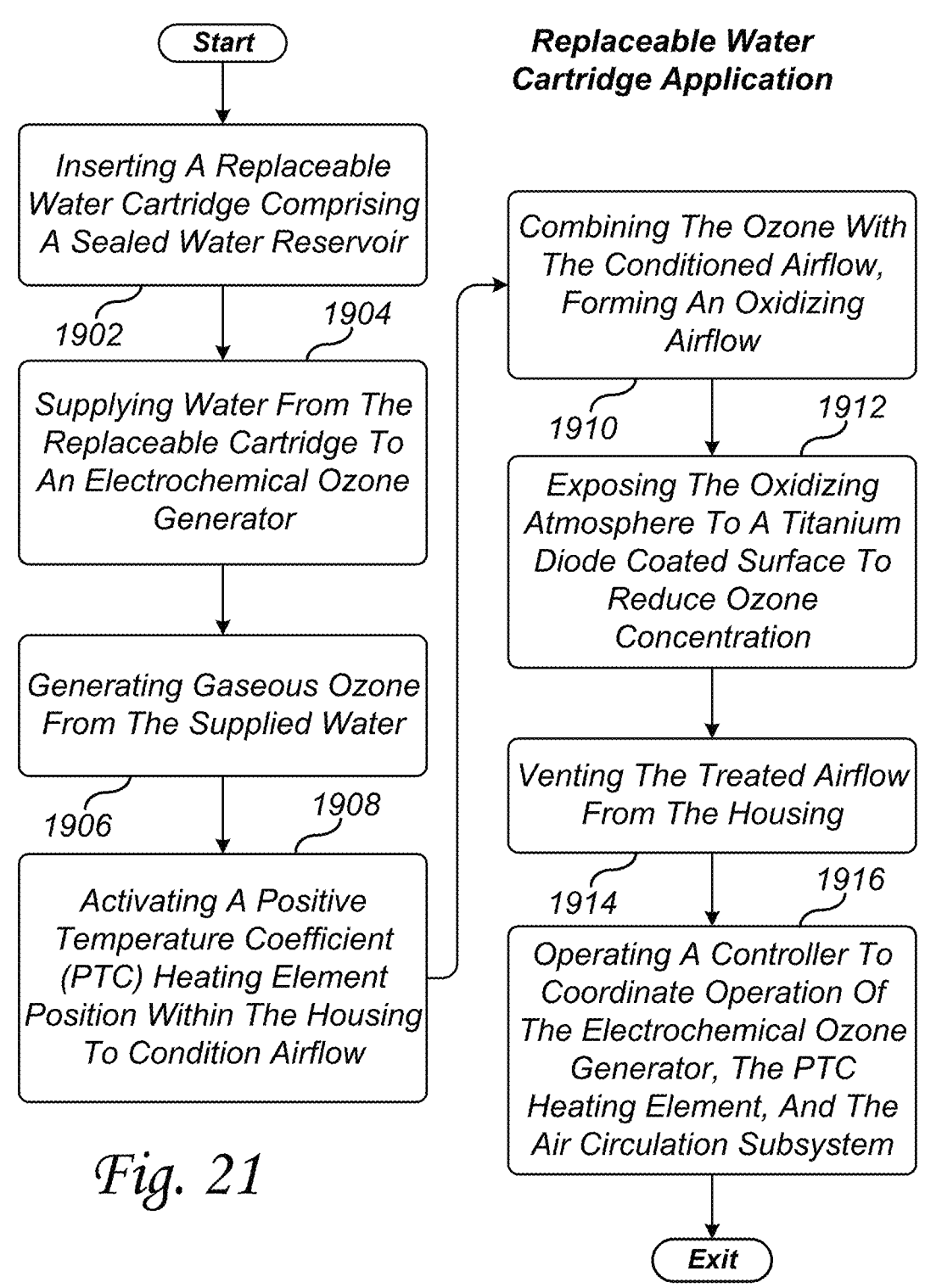

Referring to FIG. 21, there is illustrated one example of a method of performing disinfection using a modular ozone-based disinfection system having a replaceable water cartridge. In contrast to traditional fixed-reservoir systems, this embodiment integrates a positive temperature coefficient (PTC) heating element to condition airflow before ozone mixing, allowing for enhanced oxidation performance. The modularity, combined with thermal conditioning, provides a versatile and compact solution well-suited for disinfection applications in enclosed environments where airflow dynamics and temperature can influence efficacy. The method begins in step 1902 by inserting a replaceable water cartridge comprising a sealed water reservoir into a housing of the disinfection system.

In step 1904, water is supplied from the replaceable cartridge to an electrochemical ozone generator positioned within the housing. This fluid transfer can occur via integrated fluid connectors configured to engage automatically upon insertion of the cartridge.

In step 1906, the electrochemical ozone generator generates gaseous ozone from the supplied water. The electrochemical generator can comprise ion exchange material 534 and electrodes, producing ozone gas via electrolytic reaction, without requiring chemical additives.

In step 1908, a positive temperature coefficient (PTC) heating element 168 is activated. Positioned within the housing, the PTC element warms the incoming airflow, which can increase ozone gas dispersion and improve downstream photocatalytic and oxidation reactions.

In step 1910, the conditioned airflow is combined with the ozone gas to form an oxidizing atmosphere. This oxidizing mixture is circulated within the housing in preparation for treatment by internal catalytic surfaces.

In step 1912, the oxidizing atmosphere is exposed to a titanium dioxide-coated surface 110 positioned within the housing. This exposure promotes a photocatalytic reaction that breaks down ozone and other volatile organic compounds, thereby reducing the ozone concentration to levels compliant with applicable human exposure safety limits.

In step 1914, the treated airflow is vented from the housing, now rendered safe for return to the surrounding environment. The venting process may be assisted by one or more fans (104A, 104B) controlled by the system.

In step 1916, a controller 500 operates to coordinate the electrochemical ozone generator 516, the PTC heating element 168, and the air circulation subsystem. This coordination allows the system to maintain optimized temperature and ozone generation parameters, execute stored disinfection modes, and ensure safety thresholds are respected at all times.

Referring to FIG. 22, there is illustrated one example of a method of performing disinfection using a modular ozone-based disinfection system 100 having a replaceable water cartridge 126. This embodiment highlights enhanced monitoring and safety interlocks that intelligently track cartridge status and system operation to support automated disablement and remote communication features. These features are particularly valuable for environments requiring strict compliance with air quality safety limits and equipment servicing protocols.

The method begins in step 2002 by inserting the replaceable water cartridge 126, which comprises a sealed water reservoir, into a housing 156 of the modular ozone-based disinfection system 100. The housing 156 includes keyed alignment features such as an alignment ridge 162 and a seal cap 158 to ensure proper orientation and to prevent contamination.

In step 2004, water is supplied from the replaceable water cartridge 126 to the electrochemical ozone generator 516, which can comprise ion exchange material 534 and is positioned within the housing 156.

In step 2006, the electrochemical ozone generator 516 uses the water to generate gaseous ozone for use in air disinfection.

In step 2008, an air circulation subsystem—which includes one or more fans 104A—directs an airflow 402 within the housing 156 to combine with the generated gaseous ozone, forming an oxidizing atmosphere 404.

In step 2010, the oxidizing atmosphere is exposed to a titanium dioxide-coated surface 110 positioned within the housing 156. The surface 110 is configured to promote a photocatalytic oxidation reaction, reducing the ozone concentration to a level compliant with applicable human exposure safety limits.

In step 2012, the resulting treated airflow 408 is vented from the housing 156 to the surrounding environment.

In step 2014, the controller 500, which comprises a microcontroller 502, memory 504, and communication interfaces 508, monitors the usage of the replaceable water cartridge 126 based on activity of the electrochemical ozone generator 516.

In step 2016, the system determines a cartridge replacement status based on the monitored generator activity and tracked water consumption. When the cartridge is determined to be depleted or removed, the system proceeds to step 2018, where it automatically disables the electrochemical ozone generator 516 to prevent further operation, ensuring user safety and preserving system performance.

Finally, in step 2020, operational status data is transmitted from the controller 500 to a remote data processing resource 702 or computing device 732 via the communication interface 508. The transmitted data may include alerts about cartridge status, remaining operational time, or any fault conditions detected during operation.

This intelligent cartridge tracking method enhances field serviceability and compliance monitoring, particularly in mission-critical environments such as hospitals, laboratories, and commercial food preparation facilities.

Referring to FIG. 23A, there is illustrated exemplary embodiments of a method of performing disinfection using a modular ozone-based disinfection system 100 having a replaceable water cartridge 126 that can be interchangeable with the methods of the present invention. This method highlights advanced cartridge validation, intelligent environmental conditioning, and enhanced photocatalytic oxidation techniques using synchronized subsystems. The method leverages integrated sensors and controllers to tailor operational responses based on user input and environmental feedback, offering safety, precision, and modularity. The method begins in step 2102 by activating an ultraviolet (UV) lamp 108A/108B positioned within the housing to irradiate an internal airflow containing ozone. This UV irradiation enhances air disinfection and promotes photocatalytic oxidation on internal treatment surfaces, such as those coated with titanium dioxide 110, further reducing ozone levels and neutralizing pathogens.

In step 2104, the method includes that the one or more stored operational modes comprise at least one of: a timed disinfection cycle, a sensor-triggered activation cycle, or a remotely initiated command. These modes, selectable via the controller 500, enable tailored operation for various environments and usage schedules.

In step 2106, proper alignment of the replaceable water cartridge 126 is verified using one or more keyed engagement features 162 between the cartridge and the housing 156. These features prevent improper installation and ensure fluidic and electrical interfaces are properly established, which is essential for consistent disinfection output.

In step 2108, airflow is recirculated within the housing using the air circulation subsystem 104A/B after completion of a disinfection cycle. This promotes internal ozone reduction, ensuring that no residual ozone is released into the surrounding environment and that discharge complies with human exposure safety limits.

In step 2110, the operational status data is logged at a remote data processing resource 702, which can include information such as run cycles, ozone generation history, and maintenance alerts. This data can be used for compliance monitoring, fleet maintenance tracking, or remote diagnostics.

In step 2112, the system regulates activation of the positive temperature coefficient (PTC) heating element 168 based on ambient temperature or humidity conditions detected by sensors 512, thereby enhancing disinfection efficacy by pre-conditioning the air.

In step 2114, the method preheats airflow passing through the housing using the PTC heating element 168, ensuring optimal conditions for ozone mixing and photocatalytic reactions at the titanium dioxide-coated surfaces 110.

In step 2116, the PTC heating element 168 and UV lamp 108A/108B are operated in a synchronized manner to jointly enhance air treatment effectiveness by combining thermal conditioning and photonic oxidation processes.

In step 2118, the controller 500 generates an alert when the cartridge replacement status indicates depletion or misalignment of the replaceable water cartridge 126. The alert can be presented via the display 506, transmitted to a remote computing device 732, or recorded in memory 504 for later review.

Referring to FIG. 23B, there is illustrated exemplary embodiments of a method of performing disinfection using a modular ozone-based disinfection system 100 having a replaceable water cartridge 126 that can be interchangeable with the methods of the present invention. This method extends the system's utility by integrating advanced geolocation, wireless data communication, and dynamic control functionality, ensuring that the disinfection process is secure, compliant, and responsive to changing environmental and operational conditions. The method begins in step 2120 by wirelessly transmitting the operational status data using a communication interface 508 integrated with the disinfection system 100. The communication interface 508 is operationally related to the controller 500, enabling real-time updates to be sent to a remote data processing resource 702 or a computing device 732.

In step 2122, the method includes determining a geographic location of the modular ozone-based disinfection system 100 using a global positioning system (GPS) module 514. The GPS module 514 is operationally related to the controller 500 and allows the system to track its current position.

In step 2124, the controller 500 disables the electrochemical ozone generator 516 when the geographic location of the disinfection system 100 is determined to be outside a predefined geographic zone stored within the controller's memory 504. This ensures that ozone disinfection operations are only permitted in authorized or environmentally appropriate locations.

In step 2126, the method includes re-enabling the electrochemical ozone generator 516 when the GPS module 514 detects that the system has returned to within the predefined geographic zone. This geo-fencing functionality ensures safe and compliant use of the ozone generator.

In step 2128, the system 100 records timestamped operational data including ozone generation cycles, cartridge status, and other performance metrics. These logs can be used for audit verification, compliance checks, and operational analytics.

In step 2130, the controller 500 receives a remote override command from either the remote data processing resource 702 or the computing device 732. This command can be used to remotely initiate, modify, or suspend a stored operational mode, allowing for offsite control and monitoring by a technician 302 or admin user 304.

In step 2132, the method includes comparing an ozone concentration in the outgoing airflow (e.g., ozone gas flow 414 or purified airflow 408) to a predetermined safety threshold using a sensor 512, and generating a safety signal when the ozone concentration exceeds the safety limit. This automatic safety protocol ensures that only ozone levels compliant with human exposure safety limits are discharged into occupied environments.

The capabilities of the present invention can be implemented in software, firmware, hardware, or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A system comprising:

a controller;

an electrolytic ozone generator positioned within or adjacent to a refrigerated space and configured to generate gaseous ozone from water;

an air circulation system comprising one or more fans configured to direct airflow from the refrigerated space and to mix the airflow with the gaseous ozone; a gaseous ozone neutralization surface configured to reduce residual ozone in the mixed airflow; and a manganese dioxide treatment module positioned to receive the gaseous ozone and configured to chemically react with the ozone to produce hydroxyl radicals for disinfection.

2. The system of claim 1, further comprising:

an aqueous ozone circuit configured to route ozonated water into a water line used by an ice maker or refrigerator water dispenser.

3. The system of claim 1, wherein the controller is further configured to maintain continuous purification during normal operation of the refrigerated space.

4. The system of claim 1, wherein the system is configured to deliver treated air into an interior bin of an ice machine.

5. The system of claim 1, further comprising a sensor configured to detect the concentration of the gaseous ozone in the refrigerated space, wherein the controller is configured to reduce the operation of the electrolytic ozone generator in response to the detected concentration of the gaseous ozone.

6. The system of claim 1, wherein the controller is configured to operate a disinfection mode for a fixed period of time and then automatically transition to a purification mode.

7. A method of using the system of claim 1, the method comprising the steps of:

generating gaseous ozone and aqueous ozone from water using the electrolytic ozone generator;

directing gaseous ozone to mix with an airflow from the refrigerated space;

exposing the airflow to the gaseous ozone neutralization surface to reduce the ozone concentration in the airflow;

delivering the airflow into the refrigerated space; and directing the aqueous ozone into a water pathway used by an ice-making unit or a water dispensing system associated with the refrigerated space.

8. A system comprising:

an electrolytic ozone generator positioned within or adjacent to a refrigerated space and configured to generate gaseous ozone from water;

an air circulation system comprising one or more fans configured to direct the gaseous ozone into the refrigerated space;

a controller configured to:

operate the electrolytic ozone generator and the air circulation system in a disinfection mode in which the gaseous ozone is directed into the refrigerated space to raise an ambient ozone level; and operate the air circulation system in a purification mode in which the gaseous ozone containing air is passed across a gaseous ozone neutralization surface to reduce the ozone concentration in the airflow.

9. The system of claim 8, wherein the controller is configured to operate the disinfection mode for a fixed period of time and then automatically transition to the purification mode.

10. The modular ozone-based disinfection system of claim 8, wherein the controller comprises a timer, a memory storing operational profiles, and one or more user-selectable cleaning modes.

11. The system of claim 8, wherein the controller is further configured to log ozone cycle data for safety or compliance tracking.

12. The system of claim 8, wherein the refrigerated space is an ice machine enclosure or refrigerator storage compartment.

13. The system of claim 8, further comprising:

an aqueous ozone circuit configured to route ozonated water into a water line used by an ice maker or refrigerator water dispenser.

14. The system of claim 8, further comprising:

a manganese dioxide treatment module positioned to receive the gaseous ozone and configured to chemically react with the ozone to produce hydroxyl radicals for disinfection.

15. The system of claim 8, further comprising:

an electronically controlled door locking mechanism configured to automatically secure a door of the refrigerated space when the system operates in the disinfection mode.

16. The system of claim 8, wherein the controller is further configured to unlock the door of the refrigerated space only after the ozone concentration has been reduced to a level suitable for return to an occupied environment.

17. A method of using the system of claim 8, the method comprising the steps of:

using the electrolytic ozone generator to generate gaseous ozone and aqueous ozone from water;

directing gaseous ozone into the refrigerated space to raise its ambient ozone level;

directing air from the refrigerated space across the gaseous ozone neutralization surface to reduce the gaseous ozone concentration; and directing the aqueous ozone into a water pathway for use by an ice maker or water dispenser associated with the refrigerated space.

18. A system comprising:

a controller;

an electrolytic ozone generator configured to generate a gaseous ozone and an aqueous ozone from water;

a manganese dioxide treatment module positioned to receive the gaseous ozone and configured to chemically react with the ozone to produce hydroxyl radicals for disinfection; and a water line that routes the aqueous ozone for use by an ice machine or a water dispenser associated with a refrigerator.

19. The system of claim 18, wherein the manganese dioxide treatment module is positioned within an airflow path downstream of the ozone generator.

20. The system of claim 18, wherein the aqueous ozone circuit comprises one or more valves and fluid lines configured to direct ozonated water to an ice tray or water dispensing line.

21. The system of claim 18, further comprising a fan configured to emit hydroxyl-enriched air into the refrigerated space during operation of the manganese dioxide treatment module.

22. The system of claim 18, wherein the controller is configured to operate a hydroxyl-enriched air treatment mode during idle periods of the ice machine or the refrigerator.

23. The system of claim 18, wherein the system is mounted to a rear or top wall of the refrigerator or the ice machine and is configured for internal airflow capture and treatment.

24. A method of using the system of claim 18, the method comprising the steps of:

generating gaseous ozone from water;

directing the gaseous ozone over the manganese dioxide treatment module to produce a hydroxyl-enriched air; and circulating the hydroxyl-enriched air into a confined refrigerated space, of the ice machine or the refrigerator, for odor or microbial control.

* * * * *